(12) United States Patent
Lu et al.

(10) Patent No.: US 11,041,192 B2
(45) Date of Patent: Jun. 22, 2021

(54) METHOD FOR AMPLIFYING DNA

(71) Applicant: SHANGHAI XUKANG MEDICAL SCIENCE & TECHNOLOGY CO., LTD, Shanghai (CN)

(72) Inventors: Sijia Lu, Beijing (CN); Guangjun Yin, Beijing (CN)

(73) Assignee: SHANGHAI XUKANG MEDICAL SCIENCE & TECHNOLOGY CO., LTD, Shanghai (CN)

(*) Notice: Subject to any disclaimer, the term of this patent is extended or adjusted under 35 U.S.C. 154(b) by 422 days.

(21) Appl. No.: 15/756,987

(22) PCT Filed: Aug. 29, 2016

(86) PCT No.: PCT/CN2016/097208
§ 371 (c)(1),
(2) Date: Mar. 2, 2018

(87) PCT Pub. No.: WO2017/036374
PCT Pub. Date: Mar. 9, 2017

(65) Prior Publication Data
US 2018/0251826 A1     Sep. 6, 2018

(30) Foreign Application Priority Data

Sep. 2, 2015 (CN) .......................... 201510556237.2

(51) Int. Cl.
| C12Q 1/68 | (2018.01) |
| C12Q 1/6848 | (2018.01) |
| C12N 15/10 | (2006.01) |
| C12Q 1/686 | (2018.01) |
| C12Q 1/6876 | (2018.01) |

(52) U.S. Cl.
CPC ........... *C12Q 1/6848* (2013.01); *C12N 15/10* (2013.01); *C12Q 1/686* (2013.01); *C12Q 1/6876* (2013.01); *C12Q 2600/16* (2013.01)

(58) Field of Classification Search
CPC .... C12Q 1/6848; C12Q 1/686; C12Q 1/6876; C12Q 2600/16; C12N 15/10
See application file for complete search history.

(56) References Cited

U.S. PATENT DOCUMENTS

| 7,718,403 B2 | 5/2010 | Kamberov et al. | |
| 10,208,339 B2* | 2/2019 | Mir | C12Q 1/6874 |
| 2017/0183721 A1* | 6/2017 | Zong | C12Q 1/6846 |

FOREIGN PATENT DOCUMENTS

| CN | 103890191 A | 6/2014 |
| CN | 105602939 A | 5/2016 |
| WO | 2004/081225 A2 | 9/2004 |
| WO | 2012/166425 A2 | 12/2012 |

OTHER PUBLICATIONS

The International Search Report for PCT/CN2016/097208.
Minfeng Chen et al: "Comparison of Multiple Displacement Amplification (MDA) and Multiple Annealing and Looping-Based Amplification Cycles (MALBAC) in Single-Cell Sequencing", PLOS ONE, vol. 9, No. 12, Dec. 8, 2014(Dec. 8, 2014), p. e114520, XP055441867, DOI:10.371/journal.pone.0114520 *table 1*.
The extended European Search Report of European Patent Application No. 16840803.7, dated Jul. 1, 2019.

* cited by examiner

*Primary Examiner* — David C Thomas
(74) *Attorney, Agent, or Firm* — Jun He Law Offices P.C.; James J. Zhu

(57) ABSTRACT

The present application relates to a method of amplifying genomic DNA of a cell, comprising: (a) providing a reaction mixture, wherein the reaction mixture comprises the genomic DNA, a first type of primer, a second type of primer, a mixture of nucleotide monomers, and a nucleic acid polymerase, wherein the first type of primer comprises, in a 5' to 3' orientation, a common sequence and a variable sequence, wherein the common sequence consists of three or two types of bases selected from the group consisting of four types of bases: G, A, C and T, providing that the common sequence does not comprise G and C at the same time, and wherein the second type of primer comprises the common sequence but not the variable sequence; (b) placing the reaction mixture in a first thermal cycle program such that the variable sequence of the first type of primer can pair with the genomic DNA and amplify the genomic DNA to obtain a genomic amplification product, wherein the genomic amplification product comprises the common sequence at its 5' end and comprises complementary sequence of the common sequence at its 3' end; (c) placing the reaction mixture obtained from step (b) in a second thermal cycle program, such that the common sequence of the second type of primer can pair with 3' end of the genomic amplification product and amplify the genomic amplification product to obtain an expanded genomic amplification product, wherein the reaction mixture is provided prior to the step (b) and the step (c). The present application also relates to a kit for amplifying genomic DNA.

36 Claims, 16 Drawing Sheets
Specification includes a Sequence Listing.

| sample | raw reads | GC% | high quality reads | high quality of raw | mapped reads | mapping rate | mapped of raw | unique mapped reads | unique mapped of raw | average depth |
|---|---|---|---|---|---|---|---|---|---|---|
| 2_1 | 5,359,926 | 50 | 5,294,229 | 98.77% | 5,273,114 | 99.60% | 98.38% | 5,272,576 | 98.37% | 10344.7 |
| 3_1 | 5,955,406 | 51 | 5,879,987 | 98.73% | 5,852,831 | 99.54% | 98.28% | 5,852,227 | 98.27% | 11305.6 |
| 3_2 | 5,473,878 | 50 | 5,401,002 | 98.67% | 5,380,490 | 99.62% | 98.29% | 5,379,921 | 98.28% | 10228.5 |
| gDNA | 5,116,437 | 51 | 5,041,704 | 98.54% | 4,996,489 | 99.10% | 97.66% | 4,995,953 | 97.64% | 8978.32 |

FIG. 10

| sample | raw_reads | GC% | high_quality_reads | high_quality_of_raw | mapped reads | mapping_rate | mapped_of_raw | unique_mapped_reads | unique_mapped_of_raw |
|---|---|---|---|---|---|---|---|---|---|
| o_4_1 | 1,458,410 | 45 | 1,265,761 | 86.79% | 1,192,089 | 94.18% | 81.74% | 1,140,356 | 78.19% |
| o_4_2 | 1,451,015 | 45 | 1,267,234 | 87.33% | 1,182,780 | 93.34% | 81.51% | 1,130,957 | 77.94% |
| o_4_3 | 1,476,933 | 46 | 1,309,265 | 88.65% | 1,236,799 | 94.47% | 83.74% | 1,183,620 | 80.14% |
| o_4_4 | 1,575,651 | 45 | 1,421,209 | 90.20% | 1,334,005 | 93.86% | 84.66% | 1,273,473 | 80.82% |
| o_4_5 | 1,362,532 | 45 | 1,190,115 | 87.35% | 1,118,441 | 93.98% | 82.09% | 1,068,168 | 78.40% |
| o_4_6 | 1,359,674 | 45 | 1,181,547 | 86.90% | 1,115,963 | 94.45% | 82.08% | 1,066,218 | 78.42% |
| o_4_7 | 1,559,226 | 45 | 1,379,803 | 88.49% | 1,305,985 | 94.65% | 83.76% | 1,248,589 | 80.08% |
| o_4_8 | 1,585,008 | 45 | 1,385,882 | 87.44% | 1,304,549 | 94.13% | 82.31% | 1,244,975 | 78.55% |
| o_4_9 | 1,484,339 | 46 | 1,332,354 | 89.76% | 1,258,848 | 94.48% | 84.81% | 1,202,310 | 81.00% |
| o_4_10 | 1,598,205 | 46 | 1,379,286 | 86.30% | 1,300,280 | 94.27% | 81.36% | 1,242,068 | 77.72% |
| 3_10 | 1,119,382 | 44 | 816,349 | 72.93% | 757,517 | 92.79% | 67.67% | 724,631 | 64.73% |
| 3_1 | 1,250,532 | 44 | 1,136,730 | 90.90% | 1,081,520 | 95.14% | 86.48% | 1,033,433 | 82.64% |
| 3_2 | 1,468,902 | 44 | 1,206,126 | 82.11% | 1,136,495 | 94.23% | 77.37% | 1,084,198 | 73.81% |
| 3_3 | 1,377,000 | 44 | 1,081,378 | 78.53% | 1,011,457 | 93.53% | 73.45% | 962,801 | 69.92% |
| 3_4 | 1,472,813 | 45 | 1,194,106 | 81.08% | 1,122,637 | 94.01% | 76.22% | 1,069,749 | 72.63% |
| 3_5 | 1,375,899 | 45 | 1,124,754 | 81.75% | 1,053,849 | 93.70% | 76.59% | 1,002,593 | 72.87% |
| 3_6 | 1,430,603 | 44 | 1,184,156 | 82.77% | 1,113,865 | 94.06% | 77.86% | 1,061,871 | 74.23% |
| 3_7 | 1,493,585 | 45 | 1,344,445 | 90.01% | 1,271,132 | 94.55% | 85.11% | 1,212,146 | 81.16% |
| 3_8 | 1,417,384 | 45 | 1,207,205 | 85.17% | 1,134,371 | 93.97% | 80.03% | 1,080,928 | 76.26% |

FIG. 15

METHOD FOR AMPLIFYING DNA

FIELD OF THE INVENTION

The present disclosure relates to a method for amplifying DNA, in particular, a method for amplifying whole genome of a single cell.

BACKGROUND

Single-cell whole genome sequencing is a new technique for amplifying and sequencing whole-genome at single-cell level. Its principle is to amplify minute amount whole-genome DNA isolated from a single cell, and perform high-throughput sequencing after obtaining a high coverage of the complete genome. Two prerequisites are needed for establishment of this technique: 1. high-quality whole-genome amplification technique; and 2. a low-cost, high-throughput, sequencing technique.

Currently, there are four major types of whole-genome amplification techniques: Primer Extension Preamplification-Polymerase Chain Reaction (referred to as PEP-PCR, for detailed method see Zhang L, Cui X, Schmitt K, Hubert R, Navidi W, Arnheim N. 1992. Whole genome amplification from a single cell: implications for genetic analysis. Proc Natl Acad Sci USA. 89 (13):5847-51.), Degenerate Oligonucleotide-Primed Polymerase Chain Reaction (referred to as DOP-PCR, for detailed method see Telenius H, Carter N P, Bebb C E, Nordenskjo M, Ponder B A, Tunnacliffe A. 1992. Degenerate oligonucleotide-primed PCR: general amplification of target DNA by a single degenerate primer. Genomics 13:718-25), Multiple Displacement Amplification (referred to as MDA, for detailed method see Dean F B, Nelson J R, Giesler T L, LaskenRS. 2001. Rapid amplification of plasmid and phageDNA using phi29 DNA polymerase and multiply-primed rolling circle amplification. Genome Res. 11:1095-99), and Multiple Annealing and Looping Based Amplification Cycles (referred to as MALBAC, for detailed method see PCT patent application No. WO2012166425). However, some of the currently-available conventional amplification methods are easy to operate but ultimately lead to undesirable amplification results, while others have good amplification effect but the operation process of which are rather complicated. Taking MALBAC as an example, it mainly has the following defects: 1. Generally, amplification products can only be obtained after going through several steps like cell lysing, lysing termination (by increasing temperature/adding of a neutralizing reagent), pre-amplification, and amplification, etc. The entire process involves preparation of multiple reagents and addition of liquids with lid being opened, which increase the risk of introducing environmental contamination. 2. The entire experimental process lasts more than 4 hours, with a low efficiency concerning personnel and instrument, and thus cannot provide satisfactory results within a short period of time for samples that are clinically in urgent need of verification. 3. The entire experimental process requires a high degree of proficiency of the operators, and first-time users cannot obtain satisfactory amplification results in a short time.

Therefore, at present there is an urgent need for an improved amplification method that overcomes one, more, or all defects of the conventional amplification methods.

BRIEF SUMMARY OF THE INVENTION

The present disclosure provides a method of amplifying genomic DNA of a cell and a kit for amplifying genomic DNA.

In one aspect of the present application, a method of amplifying genomic DNA of a cell is provided, said method comprises: (a) providing a reaction mixture, wherein the reaction mixture comprises the genomic DNA, a first type of primer, a second type of primer, a mixture of nucleotide monomers, and a nucleic acid polymerase, wherein the first type of primer comprises, in a 5' to 3' orientation, a common sequence and a variable sequence, wherein the common sequence consists of three or two types of bases selected from the group consisting of four types of bases: G, A, C and T, providing that the common sequence does not comprise G and C at the same time, and wherein the second type of primer comprises the common sequence but not the variable sequence; (b) placing the reaction mixture in a first thermal cycle program such that the variable sequence of the first type of primer can pair with the genomic DNA and amplify the genomic DNA to obtain a genomic amplification product, wherein the genomic amplification product comprises the common sequence at its 5' end and comprises complementary sequence of the common sequence at its 3' end; (c) placing the reaction mixture obtained from step (b) in a second thermal cycle program, such that the common sequence of the second type of primer can pair with 3' end of the genomic amplification product and amplify the genomic amplification product to obtain an expanded genomic amplification product, wherein the reaction mixture is provided prior to the step (b) and the step (c).

In some embodiments, the method further comprises analyzing the amplification product to identify disease- or phenotype-associated sequence features. In some embodiments, the disease- or phenotype-associated sequence features include chromosomal abnormalities, chromosomal translocation, aneuploidy, partial or complete chromosomal deletion or duplication, fetal HLA haplotypes and paternal mutations. In some embodiments, the disease or phenotype is selected from the group consisting of: beta-thalassemia, Down's syndrome, cystic fibrosis, sickle cell disease, Tay-Sachs disease, Fragile X syndrome, spinal muscular atrophy, hemoglobinopathy, Alpha-thalassemia, X-linked diseases (diseases dominated by genes on the X chromosome), spina bifida, anencephaly, congenital heart disease, obesity, diabetes, cancer, fetal sex, and fetal RHD.

In some embodiments, the genomic DNA is contained within a cell, and the reaction mixture further comprises a surfactant and/or a lyase capable of lysing the cell.

In some embodiments, the method further comprises placing the reaction mixture in a lysing thermal cycle program prior to said steps (b) and (c), such that the cell is lysed and the genomic DNA is released.

In some embodiments, the common sequence is selected such that the common sequence does not substantially bind to genomic DNA to cause amplification. In some embodiments, the common sequence is selected from the group consisting of SEQ ID NO: 1, SEQ ID NO: 2, SEQ ID NO: 3, SEQ ID NO: 4, SEQ ID NO: 5, and SEQ ID NO: 6.

In some embodiments, the variable sequence comprises a random sequence. In some embodiments, the variable sequence has a length of 2-20 bases, 3-10 bases, 4-9 bases, or 5-8 bases. In some embodiments, three or more base positions in the variable sequence consist of one or more types of bases selected from G, A and T, or consist of one or more types of bases selected from C, A and T. In some embodiments, the three or more base positions are located at 3' end or in the middle of the variable sequence. In some embodiments, the variable sequence is selected from the group consisting of (N)nGGG, (N)nTTT, (N)mTNTNG, (N)xGTGG(N)y, wherein N refers to any nucleotide that can pair with a naturally occurring nucleic acid, n is a positive integer selected from 3-17, m is a positive integer selected from 3-15, x and y are positive integers selected from 3-13, respectively. In some embodiments, the variable sequence is selected such that the variable sequence is homogeneously distributed in genome and with a high coverage.

In some embodiments, the first type of primer includes a sequence of SEQ ID NO: 11 [GTGAGTGATGGTT-GAGGTAGTGTGGAG], SEQ ID NO: 12 [GTGAGT-GATGGTTGAGGTAGTGTGGAG GGG], SEQ ID NO: 13 [GTGAGTGATGGTTGAGGTAGTGTGGAG TTT], SEQ ID NO: 14 [GTGAGTGATGGTTGAGGTAGTGTGGAG-NNNTNTNG] or SEQ ID NO: 15 [GTGAGTGATGGTT-GAGGTAGTGTGGAGNNNGTGGNN], and the second type of primer, in a 5' to 3' orientation, has a sequence of SEQ ID NO: 1 [GTGAGTGATGGTTGAGGTAGTGTG-GAG], wherein N is any nucleotide that can pair with a naturally occurring nucleic acid.

In some embodiments, the nucleic acid polymerase has thermostability and/or strand displacement activity. In some embodiments, the nucleic acid polymerase is selected from the group consisting of Phi29 DNA polymerase, Bst DNA polymerase, Pyrophage 3137, Vent polymerase (e.g., *Thermococcus litoralis* Vent polymerase, Deep Vent polymerase, Vent(-exo) polymerase, Deep Vent(-exo) polymerase), TOPOTaq DNA polymerase, 9° Nm polymerase, Klenow Fragment DNA polymerase I, MMLV reverse transcriptase, AMV reverse transcriptase, HIV reverse transcriptase, T7 phase DNA polymerase variant (lacking 3'-5' exonuclease activity), Phusion® High-Fidelity DNA polymerase, Taq polymerase, Bst DNApolymerase (full-length), *E. coli* DNA polymerase, LongAmp Taq DNA polymerase, OneTaq DNA polymerase, and any combination thereof.

In some embodiments, the reaction mixture further comprises a pH regulator, such that the pH value of the reaction mixture is maintained between 7.0-9.0.

In some embodiments, the reaction mixture further comprises one or more components selected from the group consisting of: $Mg^{2+}$, dTT, bovine serum albumin, DNase inhibitor, RNase, $SO_4^{2-}$, $Cl^-$, $K^+$, $Ca^{2+}$, $Na^+$, and $(NH_4)^+$.

In some embodiments, the first thermal cycle program included: (b1) placing the reaction mixture in a thermal program capable of opening double strands of the genomic DNA; (b2) placing the reaction mixture in a thermal program that enables binding of the first type of primer to single-strand DNA template; (b3) placing the reaction mixture in a thermal program that enables extension of the length of the first type of primer that binds a single-strand DNA template under the action of the nucleic acid polymerase, to produce an amplification product; (b4) placing the reaction mixture in a thermal program capable of denaturing the amplification product into single strands; (b5) repeating steps (b2) to (b4) to a designated first cycle number. In some embodiments, the designated first cycle number is more than 2. In some embodiments, after proceeding to the second cycle, the amplification product comprises genomic amplification product comprising the common sequence at the 5' end and a complementary sequence of the common sequence at the 3' end. In some embodiments, the method further comprises a step (b4') after step (b4) and prior to step (b5), wherein the reaction mixture is placed in a suitable thermal program enabling hybridization of the 3' end and 5' end of the genome amplification product to form a loop structure, or enabling binding of the 3' end of the genomic amplification product to a primer. In some embodiments, the method directly proceeds to step (b5) after step (b4). In some embodiments, the first cycle number of the step (b5) is more than 3, more than 4, more than 5, or more than 6, and no more than 10.

In some embodiments, the step (c) comprises: (c1) placing the reaction mixture obtained from step (b) in a thermal program capable of opening DNA double strands; (c2) placing the reaction mixture in a thermal program that enables binding of the second type of primer to single strands of the genomic amplification product obtained from step (b); (c3) placing the reaction mixture in a thermal program that enables extension of the length of the second type of primer that binds to single strands of the amplification products, under the action of the nucleic acid polymerase; (c4) repeating steps (c1) to (c3) to a designated second cycle number. In some embodiments, the second cycle number in the step (c4) is greater than the first cycle number in the step (b5). In some embodiments, the thermal program in the step (b1) comprises allowing reacting for 1-10 minutes at a temperature between 90-95° C. In some embodiments, the step (b2) comprises placing the reaction mixture in more than one thermal program to promote sufficient and efficient binding of the first type of primer to the DNA template; in some embodiments, the more than one thermal program comprises: a first temperature between 5-10° C., a second temperature between 25-30° C., and a third temperature between 45-50° C.

In some embodiments, the step (b2) comprise allowing reacting at a first temperature for 3-50 s, allowing reacting at a second temperature for 3-50 s, and allowing reacting at a third temperature for 3-50 s. In some embodiments, the thermal program in the step (b3) comprises allowing reacting at a temperature of 60-90° C. for 1-15 minutes. In some embodiments, the thermal program in the step (b4) comprises allowing reacting at a temperature of 90-95° C. for 10-50 s. In some embodiments, the thermal program in the step (c1) comprises allowing reacting at a temperature of 90-95° C. for 10-30 s. In some embodiments, the thermal program in the step (c2) comprises allowing reacting at a temperature of 45-65° C. for 10-30 s. In some embodiments, the thermal program in the step (c3) comprises allowing reacting at a temperature of 60-80° C. for 1-15 minutes. In some embodiments, the genomic DNA in the step (a) is released from a lysed cell, the lysing includes thermal lysing, base lysing, enzymatic lysing or mechanical lysing.

In some embodiments, the thermal lysing comprises lysing at a temperature between 20-100° C. for 10-100 minutes. In some embodiments, the thermal lysing is carried out in presence of a lysing reagent. In some embodiments, the lysing reagent includes one or more surfactants selected from the group consisting of: NP-40, Tween, SDS, Triton X-100, EDTA, and guanidinium isothiocyanate, and/or lyase.

In another aspect of the present application, a method of amplifying genome of a cell is provided, said method comprises: (a) providing a reaction mixture, wherein the reaction mixture comprises DNA of said genome, a first type of primer, a second type of primer, a mixture of nucleotide monomers, and a nucleic acid polymerase, wherein the first type of primer comprises, in a 5' to 3' orientation, a common sequence and a variable sequence, wherein the common sequence consists of three or two types of bases selected from the group consisting of four types of bases: G, A, C and T, providing that the common sequence does not comprise G and C at the same time, and wherein the second type of primer comprises the common sequence but not the variable sequence; (b) placing the reaction mixture in a first thermal cycle program such that the variable sequence of the first type of primer can pair with the DNA of the genome and amplify the DNA of the genome to obtain a genomic amplification product, wherein the genomic amplification product comprises the common sequence at its 5' end and comprises complementary sequence of the common sequence at its 3' end; wherein the first thermal cycle program comprises: (b1) allowing reacting at a first denaturing temperature between 90-95° C. for 1-10 minutes; (b2) allowing reacting at a first annealing temperature between 5-10° C. for 3-50 s, at a second annealing temperature between 25-30° C. for 3-50 s, and at a third annealing temperature between 45-50° C. for 3-50 s; (b3) allowing reacting at a first elongation temperature between 60-90° C. for 1-15 minutes; (b4) allowing reacting at a first melting temperature between 90-95° C. for 10-50 s; (b5) repeating steps (b2) to (b4) for 6-9 cycles; (c) placing the reaction mixture obtained from step (b) in a second thermal cycle program, such that the common sequence of the second type of primer can pair with 3' end of the genomic amplification product and amplify the genomic amplification product to obtain an expanded genomic amplification product; wherein the second thermal cycle program comprises: (c1) allowing reacting at a second denaturation temperature between 90-95° C. for 1-10 minutes; (c2) allowing reacting at a second melting temperature between 90-95° C. for 10-30 s; (c3) allowing reacting at a fourth annealing temperature between 45-65° C. for 10-30 s; (c4) allowing reacting at a second elongation temperature between 60-80° C. for 1-15 minutes; (c5) repeating steps (c2) to (c4) for 5-30 cycles; (d) obtaining amplification product from the step (c); wherein the reaction mixture is provided prior to the step (b) and the step (c).

In some embodiments, the common sequence comprises or consists of SEQ ID NO: 1; the variable sequence comprises or consists of NNNNNTTT or NNNNNGGG and N is any nucleotide that can pair with a naturally-occurring nucleic acid.

In some embodiments, a kit for amplifying genomic DNA is provided, said kit comprises a mixture containing a first type of primer and a second type of primer, wherein the first type of primer comprises, in a 5' to 3' orientation, a common sequence and a variable sequence, wherein the common sequence consists of three or two types of bases selected from the group consisting of four types of bases: G, A, C and T, providing that the common sequence does not comprise G and C at the same time, and wherein the second type of primer comprises the common sequence but not the variable sequence.

In some embodiments, the mixture further comprises a mixture of nucleotide monomers and Mg2+.

In some embodiments, the mixture further comprises one or more components of the following: dTT, bovine serum albumin (BSA), pH regulator (e.g. Tris HCl), DNase inhibitor, RNase, $SO_4^{2-}$, $Cl^-$, $K^+$, $Ca^{2+}$, $Na^+$, and/or $(NH_4)^+$.

In some embodiments, the mixture further comprises a nucleic acid polymerase.

In some embodiments, the kit further comprises a surfactant and/or a lyase capable of lysing a cell. In some embodiments, the surfactant is selected from one or more of NP-40, Tween, SDS, TritonX-100, EDTA, and guanidine isothiocyanate. In some embodiments, the lyase is selected from one or more of protease K, pepsin, and papain.

In some embodiments, the mixture further comprises a surfactant and/or a lyase capable of lysing a cell.

In another aspect of the present application, a kit for amplifying genomic DNA is provided, said kit comprises a first type of primer and a second type of primer, and further comprises an instruction for users, said instruction records the following steps: mixing the first type of primer and the second type of primer in the same container before said amplifying, wherein the first type of primer comprises, in a 5' to 3' orientation, a common sequence and a variable sequence, wherein the common sequence consists of three or two types of bases selected from the group consisting of four types of bases: G, A, C and T, providing that the common sequence does not comprise G and C at the same time, and wherein the second type of primer comprises the common sequence but not the variable sequence.

BRIEF DESCRIPTION OF FIGURES

The above and other features of the present disclosure will be more comprehensively described through the following specification and claims appended, in combination with the drawings. It is understood that these drawings only depict several embodiments of the present disclosure and therefore should not be considered as limiting the scope of the disclosure. By applying the drawings, the present disclosure will be described more clearly and in more details.

FIG. 5 shows qPCR amplification results of the following: genomic DNA of normal human epidermal fibroblasts (AFP) was amplified using the three-step method of Example 2 and the two-step method of Example 3, respectively, and 4 samples were randomly selected from the amplification products obtained from the two methods (i.e., a total of 8 samples) as templates, respectively, and qPCR amplification was performed using the 6 pairs of quality inspection primers shown in Table 14 a-f therein represent data of q-PCR detection on template DNA using the quality inspection primers for chromosomes CH1, CH2, CH3, CH4, CH5, CH6 and CH7, respectively, wherein $C_T$ represents the threshold cycle number, and DNA1 and DNA2 represent positive controls.

FIG. 8 shows statistics of sequencing results obtained through second-generation sequencing of genomic libraries constructed respectively using the amplification products obtained from amplification of genomic DNA of normal human epidermal fibroblasts (AFP) using the three-step method of Example 2 (i.e. samples 3_1, 3_3, 3_4, 3_5, 3_6, 3_7, 3_8, 3_9 and 3_10) and using the two-step method of Example 3 (i.e. samples 2_1, 2_2, 2_3, 2_4, 2_5, 2_6, 2_7, 2_8, 2_9 and 2_10), respectively.

FIG. 10 shows results obtained by high-throughput sequencing of the following: genomic DNA of normal human epidermal fibroblasts (AFP) was amplified using the three-step method of Example 2 and the two-step method of Example 3, respectively, and amplification products from the two methods (wherein amplification products from the three-step method were shown as 3-1 and 3-2, and those from the two-step method were shown as 2-1) and genomic DNA extracted from human epidermal fibroblasts (AFP) (shown as Gdna), were subject to multiplex PCR respectively, and the multiplex PCR amplification products were subject to high-throughput sequencing.

FIG. 15 shows statistics of sequencing results obtained through second-generation sequencing of genomic libraries constructed with the amplification products obtained by amplifying genomic DNA of normal human epidermal fibroblasts (AFP) using the three-step method of Example 2 and using the one-step method of Example 5, respectively.

DETAILED DESCRIPTION

The present disclosure provides a method of amplifying genomic DNA, in particular a method of amplifying whole genome of a single cell.

The present disclosure is based, at least in part, on the discovery that prior to amplification reaction of genomic DNA, all reagents required for amplification can be added into a single reaction mixture, and then this reaction mixture is placed under a condition for amplification reaction, until completion of amplification. This method eliminates the need of adding reagents to a reaction mixture after initiation of amplification reaction, and thereby greatly reduces additional operations caused by, and contamination which might be resulted from addition of reagents, and greatly shortens the reaction time required.

Before the present disclosure, when two or more primers are used for genomic DNA, the amplification reaction needs to be separated into at least two steps, where different primers are used in each step, and thereby different amplification purposes are achieved. It was previously believed that, in order to avoid interferences between primers which in turns impact the amplification effect, primers required for the second step can only be added to the reaction mixture after the first step is completed, or the first step may only employ a very low cycle number (e.g., 1 cycle). Therefore, in the methods prior to the present disclosure, one can either add only the primers needed for the first step before an amplification reaction and after the first-step amplification reaction ends, add primers required for the second step to the reaction system, and perform the second-step amplification reaction (see, e.g., WO2012/166425); or only employ a very low cycle number in the first step, by which a desirable amplification efficiency can hardly be achieved. Surprisingly, the inventors of the present application found that when placing all primers originally believed to interfere with each other at once into a single reaction mixture and performing amplification under the reaction conditions of the present disclosure, an amplification effect which is comparable to that where primers are separately added can be unexpectedly obtained. Therefore, the present disclosure greatly improves reaction efficiency, shortens reaction time, and reduces the risk of sample contamination, and improves reliability of results.

Figure 1:
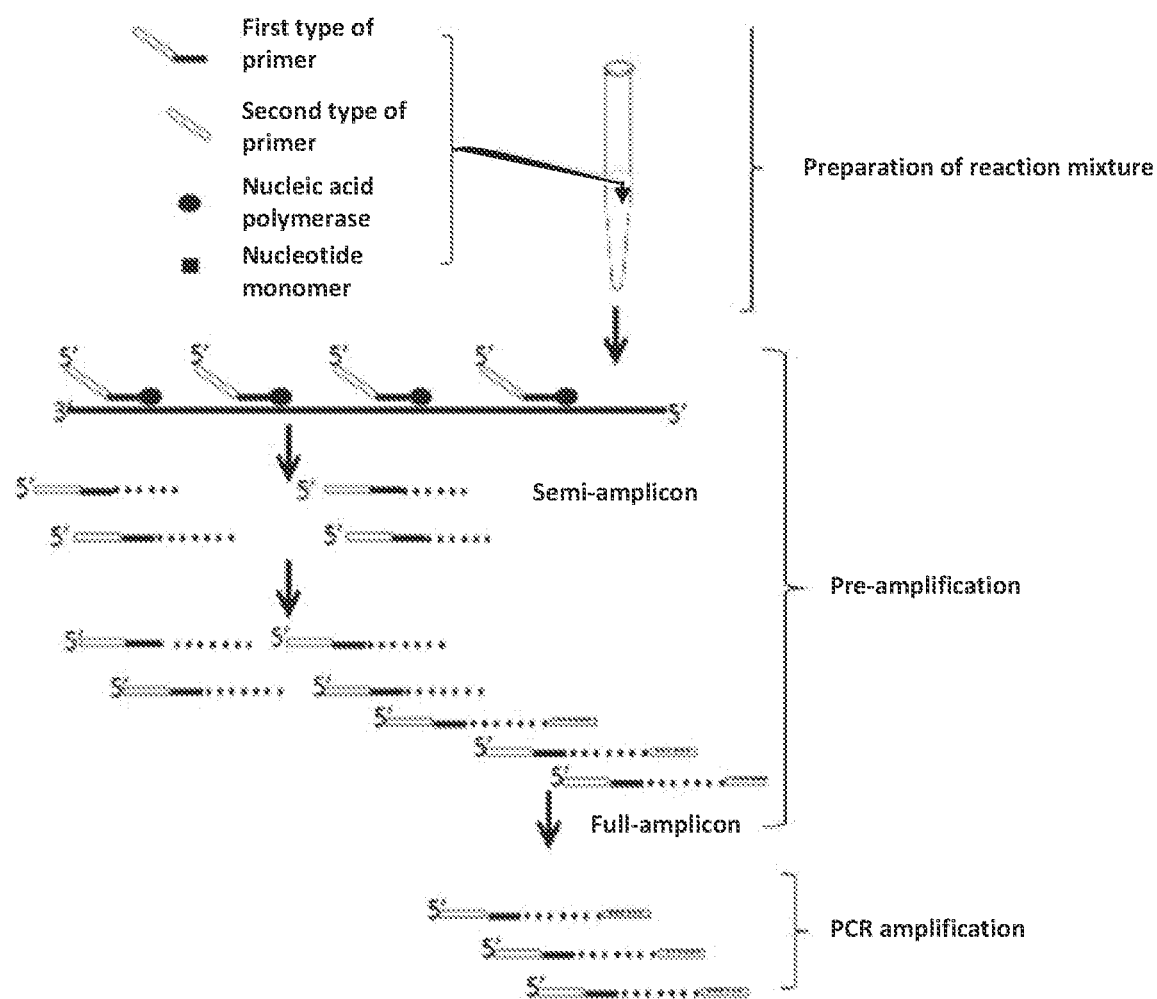
FIG. 1 shows the basic principle of the amplification method of the present application.

In one aspect, the present application provides a method of amplifying genomic DNA of a cell, comprising: (a) providing a reaction mixture, wherein the reaction mixture comprises the genomic DNA, a first type of primer, a second type of primer, a mixture of nucleotide monomers, and nucleic acid polymerase, wherein the first type of primer comprises, in a 5' to 3' orientation, a common sequence and a variable sequence, wherein the common sequence consists of three or two types of bases selected from the group consisting of four types of bases: G, A, C and T, providing that the common sequence does not comprise G and C at the same time, and wherein the second type of primer comprises the common sequence but not the variable sequence; (b) placing the reaction mixture in a first thermal cycle program such that the variable sequence of the first type of primer can pair with the genomic DNA and amplify the genomic DNA to obtain a genomic amplification product, wherein the genomic amplification product comprises the common sequence at its 5' end and comprises complementary sequence of the common sequence at its 3' end; (c) placing the reaction mixture obtained from step (b) in a second thermal cycle program, such that the common sequence of the second type of primer can pair with 3' end of the genomic amplification product and amplify the genomic amplification product to obtain an expanded genomic amplification product. See FIG. 1 for illustration of one embodiment of the method provided in the present application.

Step (a): Providing a Reaction Mixture

The method of the present application is broadly applicable for amplification of genomic DNA, particularly for rapid and accurate amplification of minute amount genomic DNA.

i. Genomic DNA

The method of the present application is preferably useful for genomic DNA. In certain embodiments, the initial amount of genomic DNA contained in a reaction mixture is no more than 10 ng, no more than 5 ng, no more than 1 ng, no more than 500 pg, no more than 200 pg, no more than 100 pg, no more than 50 pg, no more than 20 pg, or no more than 10 pg.

A genomic DNA may be from a biological sample, e.g., biological tissue, or body fluid that contains cells or free DNA. Samples containing genomic DNA can be obtained through known methods, e.g. obtained through oral mucosal samples, nasal samples, hair, mouthwash, cord blood, plasma, amniotic fluid, embryonic tissue, endothelial cells, nail samples, hoof samples, etc. A biological sample can be provided in any suitable form, for example, in paraffin embedded form, in freshly isolated form, etc. Genomic DNA may be from any species or biological species, including, but not limited to, humans, mammals, cattle, pigs, sheep, horses, rodents, birds, fish, zebrafish, shrimp, plants, yeasts, viruses or bacteria.

In certain embodiments, genomic DNA is that from a single cell, or that from two or more cells of the same type. Single cells or cells of the same type may be from, e.g., pre-implantation embryos, embryonic cells in peripheral blood of pregnant women, single sperms, egg cells, fertilized eggs, cancer cells, bacterial cells, tumor circulating cells, tumor tissue cells, or single cells or multiple cells of the same type obtained from any tissue. The method of the present application can be used to amplify DNA in some valuable samples or samples with low initial amount, e.g., human egg cells, germ cells, tumor circulating cells, tumor tissue cells, etc.

Methods for obtaining single cells are also known in the art, e.g., by the method of flow cytometry sorting (Herzenberg et al., Proc Natl Acad Sci USA 76:1453-55, 1979; Iverson et al., Prenatal Diagnosis 1:61-73, 1981; Bianchi et al., Prenatal Diagnosis 11:523-28, 1991), fluorescence-activated cell sorting, the method of separation using magnetic beads (MACS, Ganshirt-Ahlert et al., Am J Obstet Gynecol 166:1350, 1992), by using a semi-automatic cell picker (e.g., the Quixell™ cell transfer system by Stoelting Co.) or a combination thereof. In some embodiments, gradient centrifugation and flow cytometry techniques can be used to increase the efficiency of separation and sorting. In some embodiments, cells of particular types, such as cells expressing particular biomarkers, can be selected according to different properties of single cells.

Methods for obtaining genomic DNA are also well known in the art. In certain embodiments, genomic DNA can be released and obtained by lysing cells from biological samples or single cells. Lysing may be performed using any suitable method known in the art, for example, lysing can be performed by means of thermal lysing, base lysing, enzymatic lysing, mechanical lysing, or any combination thereof (see, specifically, e.g., U.S. Pat. No. 7,521,246, Thermo Scientific Pierce Cell Lysis Technical Handbook v2 and Current Protocols in Molecular Biology (1995). John Wiley and Sons, Inc. (supplement 29) pp. 9.7.1-9.7.2.).

Mechanical lysing includes methods that break cells using mechanical forces such as using ultrasonication, high speed stirring, homogenization, pressurization (e.g., French press), decompression and grinding. The most commonly used mechanical lysing method is the liquid homogenization method, which compels cell suspension to pass through a very narrow space, and thus shear force is applied on cell membrane (WO2013153176 A1).

In certain embodiments, mild lysing methods may be used. For example, cells can be lysed by being heated in a Tween-20-containing solution at 72° C. for 2 min, heated in water at 65° C. for 10 min (Esumi et al., Neurosci Res 60(4):439-51 (2008)), heated in PCR buffer II (Applied Biosystems) containing 0.5% NP-40 at 70° C. for 90 s (Kurimoto et al., Nucleic Acids Res 34(5):e42 (2006)), or using Protease (e.g. Protease K) or a chaotropic salt solution (e.g. guanidine isothiocyanate) (U.S. Patent Application No. US 20070281313).

Thermal lysing includes heating and repeated freeze-thaw methods. In some embodiments, the thermal lysing comprises lysing for 10-100 minutes at a temperature between 20-100 centigrade. In some embodiments, temperature for thermal lysing can be any temperature between 20-90, 30-90, 40-90, 50-90, 60-90, 70-90, 80-90, 30-80, 40-80, 50-80, 60-80 or 70-80° C. In some embodiments, temperature for thermal lysing is no less than 20, 30, 40 or 50° C. In some embodiments, temperature for thermal lysing is no more than 100, 90 or 80° C. In some embodiments, time for thermal lysing can be any period between 20-100, 20-90, 20-80, 20-70, 20-60, 20-50, 20-40, 20-30, 30-100, 30-90, 30-80, 30-70, 30-60, 30-50, or 30-40 minutes. In some embodiments, time for thermal lysing is no less than 20, 30, 40, 50, 60, 70, 80, or 90 minutes. In some embodiments, time for thermal lysing is no more than 90, 80, 70, 60, 50, 40, 30, or 20 minutes. In some embodiments, temperature for thermal lysing varies over time. In some embodiments, the thermal lysing is maintained under a temperature at 30-60° C. for 10-30 minutes, followed by a temperature at 70-90° C. for 5-20 minutes.

In some embodiments, the thermal lysing is carried out in the presence of a lysing reagent. In the presence of a lysing reagent, time or temperature required for lysing can be reduced. A lysing reagent can break protein-protein, lipid-lipid and/or protein-lipid interactions, thereby promoting release of genomic DNA from a cell.

In some embodiments, the lysing reagent comprises a surfactant and/or a lyase. Surfactants can be categorized into ionic, amphoteric and non-ionic surfactants. Generally, lysing efficacies of amphoteric and nonionic surfactants are weaker than that of ionic surfactants. Exemplary surfactants include, but are not limited to, one or more of NP-40, Tween, SDS, GHAPS, TritonX-100, TritonX-114, EDTA, sodium deoxycholate, sodium cholate, and guanidine isothiocyanate. Those skilled in the art can select type and concentration of a surfactant based on practical need. In some embodiments, working concentration of a surfactant is 0.01%-5%, 0.1%-3%, 0.3%-2% or 0.5-1%.

Exemplary lyases can be proteinase K, pepsin, papain, etc., or any combination thereof. In some embodiments, working concentration of a lyase is 0.01%-1%, 0.02%-0.5%, 0.03%-0.2%, or 0.4-0.1%.

In the method provided herein, a lysate containing genomic DNA can be used directly in a reaction mixture. For example, a biological sample may be pre-treated by lysing to obtain a lysate, which is then mixed with other components of the reaction mixture. If needed, the lysate can be further processed so that the genomic DNA therein is isolated, and then the isolated genomic DNA is further mixed with other components of reaction mixture to provide a reaction mixture.

In some embodiments, a nucleic acid sample obtained through lysing can be amplified without being purified.

The present application further provides a simpler method, i.e., directly mixing a genomic DNA-containing cell with other components required for amplification to obtain a reaction mixture, in other words, genomic DNA in the reaction mixture is present within a cell. In such circumstances, the reaction mixture may further contain surfactants (such as, but not limited to, one or more of NP-40, Tween, SDS, TritonX-100, EDTA, and guanidine isothiocyanate) and/or lyase (e.g., one or more of Protease K, pepsin, and papain) capable of lysing the cell. In this way, cell lysing and genomic DNA amplification both occur in the same reaction mixture, which not only improves reaction efficiency, shortens reaction time, but also retains a fairly good amplification effect.

In certain embodiments, the method provided herein may further comprise placing the reaction mixture in a lysing thermal cycle program after completion of step (a) and prior to step (b), such that the cell is lysed and the genomic DNA is released. Those skilled in the art can select a suitable lysing thermal cycle program according to the lysate components contained in the reaction mixture, type of the cell, etc. Exemplary lysing thermal cycle program includes placing the reaction mixture at 50° C. for 3 minutes to 8 hours (e.g., any time period between 3 minutes to 7 hours, 3 minutes to 6 hours, 3 minutes to 5 hours, 3 minutes to 4 hours, 3 minutes to 3 hours, 3 minutes to 2 hours, 3 minutes to 1 hour, 3 minutes to 40 minutes, 3 minutes to 20 minutes; such as 10 minutes, 20 minutes, 30 minutes, etc.), then at 80° C. for 2 minutes to 8 hours (e.g., any time period between 2 minutes to 7 hours, 2 minutes to 6 hours, 2 minutes to 5 hours, 2 minutes to 4 hours, 2 minutes to 3 hours, 2 minutes to 2 hours, 2 minutes to 1 hour, 2 minutes to 40 minutes, 2 minutes and 20 minutes; such as 10 minutes, 20 minutes, 30 minutes, etc.). The lysing thermal program can be run for 1 cycle, or 2 or more cycles as needed, depending on specific lysing conditions.

ii. Primers

The reaction mixture further contains two different types of primer, of which the first type of primer comprises, in a 5' to 3' orientation, a common sequence and a variable sequence, and the second type of primer comprises the common sequence but not the variable sequence. The variable sequence in the first type of primer can bind to genomic DNA template and a certain length of genomic template can be replicated under the action of a nucleic acid polymerase, to obtain an amplification product with a common sequence at its 5' end and a genomic sequence at its 3' end, which is also referred to as a semi-amplicon herein. The variable sequence in the first type of primer can also pair with and bind to a semi-amplicon and replicate using the semi-amplicon as a template, generating an amplification product with a common sequence at its 5' end and a complementary sequence of the common sequence at its 3' end, which is also referred to as full-amplicon herein. The second type of primer can bind to the complementary sequence of the common sequence at 3' end of a full-amplicon, and thereby further replicates the full-amplicon, and greatly increases its number.

The common sequence in the present application refers to a specific sequence located at 5' end of the first type of primer. Length of a common sequence can be, e.g., 10-30, 12-29, 15-28, 18-26, or 20-24 bases. In the present application, a suitable common sequence is selected, such that it substantially does not bind to genomic DNA, which results in amplification, and avoids polymerization between first type of primer and first type of primer or between first type of primer and second type of primer.

In certain embodiments, a common sequence only comprises three or two types of bases with poor ability of self-complementary pairing, and does not comprise the other one or two types of bases. In certain embodiments, the common sequence consists of three types of bases, G, A and T, i.e., the common sequence does not contain the C base. In certain embodiments, the common sequence consists of three types of bases, C, A and T, i.e., the common sequence does not contain the G base. In certain embodiments, the common sequence consists of two types of bases, A and T, A and C, A and G, T and C, or, T and G, i.e., the common sequence does not contain G and C at the same time. Without wishing to be bound by theory, it is believed that if a common sequence contains C or G base, primer-primer polymerization may happen, which generates polymers and thereby impairs the ability to amplify genomic DNA. Preferably, a common sequence does not have any self-pairing sequence, or any sequence that would cause primer-primer pairing, or multiple bases of the same type in succession.

In certain embodiments, a suitable base sequence of common sequence and proportion of each base thereof can be selected, to ensure that the common sequence itself does not undergo base pairing with genomic DNA template sequence or resulted in amplification.

In certain embodiments, the common sequence is selected from the group consisting of: SEQ ID NO: 1 (GTG AGT GAT GGT TGA GGT AGT GTG GAG), SEQ ID NO: 2 (GTGGAGTTAGTGAGTGTAATGGAT), SEQ ID NO: 3 (GGTTTGGTGTGGTGTGTGGTGGTG), SEQ ID NO: 4 (ACAACACTATCAATCCCTATCCTAC), SEQ ID NO: 5 (ATGGTAGTGGGTAGATGATTAGGT), SEQ ID NO: 6 (CATATCCCTATACCTAATACCATTAC).

The 5' end of the first type of primer is a common sequence, and the 3' end is a variable sequence. A common sequence and a variable sequence may be directly adjacent, or may have a spacer sequence of one or more bases. The variable sequence in the present application refers to a base sequence with an unfixed sequence, for example, it may comprise a random sequence. A random sequence may comprise any nucleotide that can undergo base pairing with a naturally-occurring nucleic acid, such as four types of naturally-occurring bases of A, T, G, and C, as well as other nucleotide analogs and modified nucleotides known to those skilled in the art, as long as it can pair with genomic DNA and achieve amplification. Nucleotide sequence in a variable sequence may be in multiple possibilities of variation. Therefore, the first type of primer may comprise a set of primers with different sequences, wherein each primer has a common sequence at its 5' end, and a variable sequence at its 3' end. The common sequences in these primers are identical, but the variable sequences may vary.

A variable sequence can have a suitable length, e.g., 2-20 bases, 2-19 bases, 2-18 bases, 2-17 bases, 2-16 bases, 2-15 bases 2-14 bases, 2-13 bases, 2-12 bases, 2-11 bases, 2-12 bases, 2-11 bases, 2-10 bases, 2-9 bases, 2-8 bases, 3-18 bases, 3-16 bases, 3-14 bases, 3-12 bases, 3-10 bases, 4-16 bases, 4-12 bases, 4-9 bases, or 5-8 bases. In certain embodiments, the variable sequence is 5 bases in length. In certain embodiments, the variable sequence is 8 bases in length. Theoretically, if base at each position is randomly selected from the four types of bases, A, T, G, and C, a variable sequence with a length of 4 bases can generate 256 possible random sequences by combination, and a variable sequence with a length of 5 bases can generate 1024 possible random sequences by combination, and so forth. These variable sequences can complementarily pair with corresponding sequences at different positions in genomic DNA, and thereby replication is initiated at different positions in genomic DNA.

The variable sequences can be selected by a random approach, certain limiting conditions can also be further applied on the basis of the random approach, in order to eliminate some unwanted situations or to enhance matching degree with target genomic DNA. In certain embodiments, three or more base positions in the variable sequence consist of one or more types of bases selected from G, A, and T (i.e., not being C), or consist of one or more types of bases from C, A, and T (i.e., not being G), to avoid complementary pairing between variable sequence and common sequence. In some embodiments, when the common sequence does not contain G but contains C, three or more base positions in the variable sequence consist of one or more types of bases of C, A and T (i.e., not being G). In some embodiments, when the common sequence does not contain C but contains G, three or more base positions in the variable sequence consist of one or more types of bases of G, A and T (i.e., not being C). In some embodiments, when a common sequence contains neither C nor G, three or more base positions in a variable sequence consist of one or more types of bases selected from G, A and T (i.e., not being C) or consists of one or more types of bases of C, A and T (i.e., not being G). The three or more bases can be located at 3' end of the variable sequence, or can be located in middle part of the variable sequence. The three or more bases may be successive or unsuccessive. For example, none of three adjacent bases at 3' end of the variable sequence is C, or three bases at 3' end of a variable sequence which are spaced from each other are not C, or certain two successive bases as well as another base spaced therefrom at 3'end of a variable sequence are not C. When the three base positions are successive, they can be in the following exemplary sequences: TTT, GGG, TTG, GAA or ATG.

In certain embodiments, the variable sequence is selected from the group consisting of: $(N)_nGGG$, $(N)_nTTT$, $(N)_mTNTNG$, and $(N)_xGTGG(N)_y$, wherein N is any random nucleotide that can undergo base pairing with a naturally-occurring nucleic acid, n is a positive integer selected from 3-17, m is a positive integer selected from 3-15, and x and y are positive integers selected from 3-13, respectively. In certain embodiments, the variable sequence in the first type of primer may have one or more sequences of $(N)_nGGG$, $(N)_nTTT$, $(N)_mTNTNG$, $(N)_xGTGG(N)_y$. In certain embodiments, a variable sequence is selected from the group consisting of SEQ ID NO: 7 (GGG), SEQ ID NO: 8 TTT), SEQ ID NO: 9 (NNNTNTNG), SEQ ID NO: 10 (NNNGTGGNN).

In certain embodiments, variable sequences that are more evenly distributed in genome and with a higher coverage can also be selected through statistical calculations, thereby increasing opportunity of recognition between the variable sequence and genomic DNA.

In certain embodiments, the first type of primer can comprise SEQ ID NO: 11 [GTGAGTGATGGTTGAGGTAGTGTGGAG], SEQ ID NO: 12 [GTGAGTGATGGTTGAGGTAGTGTGGAG GGG], SEQ ID NO: 13 [GTGAGTGATGGTTGAGGTAGTGTGGAG TTT], SEQ ID NO: 14 [GTGAGTGATGGTTGAGGTAGTGTGGAG-NNNTNTNG] or SEQ ID NO: 15 [GTGAGTGATGGTTGAGGTAGTGTGGAGNNNGTGGNN], wherein N is any nucleotide (e.g., A, T, G, C) that can undergo base pairing with a naturally-occurring nucleic acid.

The second type of primer in the reaction mixture comprises the common sequence but not the variable sequence. The 5' and 3' ends of the second type of primer may or may not contain other additional sequences. In certain embodiments, the sequence of the second type of primer consists of the common sequence of the first type of primer. In certain embodiments, the second type of primer, in a 5' to 3' orientation, comprises or consists of the sequence of SEQ ID NO: 1 [GTGAGTGATGGTTGAGGTAGTGTGGAG].

In some embodiments, concentration of the primer in the reaction mixture is 300 ng-1500 ng/µL. In some embodiments, concentration of the primer in the reaction mixture is 300 ng-1400 ng/µL, 300 ng-1200 ng/µL, 300 ng-1000 ng/µL, 300 ng-800 ng/µL, 300 ng-600 ng/µL, or 300 ng-400 ng/µL. In some embodiments, concentration of the primer in the reaction mixture is 500 ng-1400 ng/µL, 600 ng-1400 ng/µL, 800 ng-1400 ng/µL, 900 ng-1400 ng/µL, 1000 ng-1400 ng/µL or 1200 ng-1400 ng/µL. In some embodiments, concentration of the primer in the reaction mixture is 400 ng-1400 ng/µL, 500 ng-1200 ng/µL, 600 ng-1000 ng/µL, or 700 ng-800 ng/µL.

iii. Other Components

The reaction mixture further comprises other components required for DNA amplification, such as nucleic acid polymerase, a mixture of nucleotide monomers, and suitable metal ions and buffer components required for enzymatic activity, and the like. For at least one or more types of these components, reagents known in the art can be used.

Nucleic acid polymerase in the present application refers to an enzyme capable of synthesizing a new nucleic acid strand. Any nucleic acid polymerase suitable for the method of the present application can be used. Preferably, DNA polymerase is used. In certain embodiments, the method of the present application uses a thermostable nucleic acid polymerase, such as those whose polymerase activity does not decrease or decrease by less than 1%, 3%, 5%, 7%, 10%, 20%, 30%, 40% or 50% at a temperature for PCR amplification (e.g., 95° C.). In certain embodiments, the nucleic acid polymerase used in the method of the present application has strand displacement activity. The "strand displacement activity" of the present application refers to an activity of nucleic acid polymerase that enables separation of a nucleic acid template from the complementary strand with which it pairs and binds, and where such separation performs in a 5' to 3' direction, and is accompanied with generation of a new nucleic acid strand that is complementary to the template. Nucleic acid polymerases with strand displacement ability and applications thereof are known in the art, see e.g., U.S. Pat. No. 5,824,517, which is incorporated herein by reference in its entirety. Suitable nucleic acid polymerases include, but are not limited to: one or more of Phi29 DNA polymerase, Bst DNA polymerase, Bst 2.0 DNA polymerase, Pyrophage 3137, Vent polymerase (e.g. *Thermococcus litoralis* Vent polymerase, Deep Vent polymerase, Vent(-exo) polymerase, Deep Vent(-exo) polymerase), TOPOTaq DNA Polymerase, 9° Nm polymerase, Klenow Fragment DNA polymerase I, MMLV reverse transcriptase, AMV reverse transcriptase, HIV reverse transcriptase, T7 phase DNA polymerase variant (lacking 3'-5' exonuclease activity), Phusion® High-Fidelity DNA polymerase, Taq polymerase, Psp GBD (exo-) DNA polymerase, Bst DNA polymerase (full-length), *E. coli* DNA polymerase, LongAmp Taq DNA polymerase, OneTaq DNA polymerase.

In certain embodiments, the reaction mixture contains one or more of *Thermococcus litoralis* Vent polymerase, Deep Vent polymerase, Vent(-exo) polymerase, or Deep Vent(-exo) polymerase. In certain embodiments, the reaction mixture contains *Thermococcus litoralis* Vent polymerase. *Thermococcus litoralis* Vent polymerase refers to a natural polymerase isolated from *Thermococcus litoralis*. In certain embodiments, the reaction mixture contains Deep Vent polymerase. The Deep Vent polymerase refers to a natural polymerase isolated from *Pyrococcus* species GB-D. In certain embodiments, the reaction mixture contains Vent(-exo) polymerase. Vent(-exo) polymerase refers to an enzyme resulted from D141A/E143A gene engineering of *Thermococcus litoralis* Vent polymerase. In certain embodiments, the reaction mixture contains Deep Vent(-exo) polymerase. Deep Vent (-exo) polymerase refers to an enzyme resulted from D141A/E143A gene engineering of Deep Vent polymerase. The various Vent polymerases in the present application are commercially available, e.g., from New England Biolabs Company.

A reaction mixture can also comprise suitable metal ions required for exerting enzymatic activity of nucleic acid polymerase (e.g., $Mg^{2+}$ ions in suitable concentration (e.g., at a final concentration of about 1.5 mM to about 8 mM), a mixture of nucleotide monomers (e.g., dATP, dGTP, dTTP, and dCTP), bovine serum albumin (BSA), dTT (e.g., at a final concentration of about 2 mM to about 7 mM), purified water, and the like.

In certain embodiments, the reaction mixture can also further comprise a pH regulator, such that pH value of the reaction mixture is maintained between 7.0-9.0. Suitable pH regulators may include, e.g, Tris HCl and Tris $SO_4$. In certain embodiments, a reaction mixture can also further comprise one or more types of other components, e.g., DNase inhibitor, RNase, $SO_4^{2-}$, $Cl^-$, $K^+$, $Ca^{2+}$, Na+, and/or $(NH_4)^+$, and the like.

One of the features of the method provided herein is that the reaction mixture is provided prior to the step (b) and the step (c). As the preparation of the reaction mixture is fully completed before the thermal cycle program is performed, the reaction mixture can react according to predetermined settings upon entrance of the thermal cycle program, with no need to further open the lid or add any component, and thereby avoids contamination and improves reaction efficiency. In some embodiments, after the step (a) is completed, there is no need to further add reactants such as enzymes, primers and dNTPs to the reaction mixture. In some embodiments, providing of the reaction mixture is completed before the step (b). In some embodiments, no reactants (e.g., enzymes, primers, and dNTPs) are further added to the reaction mixture after initiation of the step (b). In some embodiments, the step (a) precedes the step (b) and the step (c).

Step (b): Placing in the First Thermal Cycle Program

The method provided herein comprises step (b): placing the reaction mixture in the first thermal cycle program, such that the variable sequence of the first type of primer can pair with the genomic DNA and amplify the genomic DNA to obtain a genomic amplification product, wherein the genomic amplification product comprises the common sequence at its 5' end and comprises complementary sequence of the common sequence at its 3' end.

"Amplification" in the present application means addition of nucleotides complementary to a nucleic acid template at the 3' end of a primer under the action of a nucleic acid polymerase, whereby to synthesize a new nucleic acid strand that is base-complementary to the nucleic acid template. Suitable methods for amplifying nucleic acids may be used, such as polymerase chain reaction (PCR), ligase chain reaction (LCR), or other suitable amplification methods. These methods are all known in the art, see e.g., U.S. Pat. Nos. 4,683,195 and 4,683,202, as well as Innis et al., "PCR protocols: a guide to method and applications" Academic Press, Incorporated (1990) and Wu et al. (1989) Genomics 4:560-569, all of these literatures and patents are incorporated herein by reference in their entirety.

During the process of amplification, the reaction mixture is placed in a suitable thermal cycle program, such that DNA template double strands are unwound into single strands, primers hybridize with template single strands, and primers elongate. Thus, a thermal cycle program typically comprises: a denaturing or melting temperature at which DNA template double strands are unwound into single strands; an annealing temperature at which a primer specifically hybridizes with a single-strand DNA template; and an elongation temperature at which DNA polymerase adds nucleotides complementary to DNA template bases at the 3' end of a primer, so that the primer elongates, and a new DNA strand that is complementary to the DNA template is obtained. The newly synthesized DNA strand can serve as a new DNA template in the next reaction cycle, for a new cycle of DNA synthesis.

In step (b) of the method of the present application, the reaction mixture is placed in a first thermal cycle program such that the variable sequence of the first type of primer in the reaction mixture can bind to the genomic DNA through base pairing, and that genomic DNA is replicated under the action of a nucleic acid polymerase.

In the first thermal cycle program, first the reaction mixture is placed in a thermal program capable of opening the double strands of the genomic DNA (step (b1)). To ensure that genomic DNA double strands are completely unwound into single strands (i.e., denaturing/melting), high reaction temperatures such as 90° C.-95° C. can be used and a long reaction time can be maintained. In certain embodiments, the thermal program in step (b1) comprises reacting at a temperature between 90° C.-95° C. for 1-10 minutes.

Next, the reaction mixture is placed in a thermal program that enables binding of the first type of primer to the single-strand DNA template (step (b2)). In this thermal program, the variable sequence in the first type of primer binds to complementary sequences at different positions in genomic DNA through base complementarity (i.e., annealing), and thereby replications are initiated at different positions in genomic DNA. Due to the diversity of variable sequences in the first type of primer, wherein differences exist with regard to both base ratio and sequence, the optimal binding temperature for each variable sequence to genomic DNA also varies greatly. Thus, at a given annealing temperature, it is possible that only some of the primers can bind to genomic DNA well, while the binding of the others to genomic DNA may not be ideal. In certain embodiments, the step (b2) comprises a program of placing the reaction mixture in more than one temperature, to facilitate sufficient binding of the first type of primer to the DNA template. For example, DNA denatured reaction mixture can be rapidly cooled to a low temperature, such as about 5° C.-10° C., followed by allowing the reaction mixture to react for a suitable period at different annealing temperatures respectively, by means of gradient heating, whereby to ensure that as many primers as possible pair with genomic DNA. In certain embodiments, step (b2) comprises allowing reacting for a suitable period (e.g., 3-50 s) at a first annealing temperature between 5-10° C. (e.g., 10° C.), allowing reacting for a suitable period (e.g., 3-50 s) at a second annealing temperature between 25-30° C. (e.g., 30° C.), and allowing reacting for a suitable period (e.g., 3-50 s) at a third annealing temperature between 45-50° C. (e.g., 50° C.).

It is well known in the art that annealing temperature of a primer is generally no more than 5° C. lower than Tm value of a primer, and an excessively low annealing temperature will lead to primer-primer non-specific binding, whereby resulting in primer aggregation and nonspecific amplification products. Therefore, low temperatures such as 5° C.-10° C. will not usually be used as primer annealing temperature. However, it is unexpectedly found by the inventors, that even if gradient heating starts from a low temperature (e.g., 5° C.-10° C.), pairing between primers and genomic DNA can still maintain good specificity, and amplification results still retain very low variability, indicating accurate and reliable amplification results. Meanwhile, since annealing temperatures for primers cover circumstance of low temperature, binding of wider range of primer sequences to genomic DNA is ensured, whereby better genomic coverage and amplification depth are provided.

After primer annealing thermal program, the reaction mixture is placed in a thermal program that enables elongation of the first type of primer that binds to a single-strand DNA template under the action of the nucleic acid polymerase, to produce an amplification product (step (b3)). The elongation temperature is usually related to the optimum temperature for DNA polymerase, for which those skilled in the art can make specific selection according to specific reaction mixture. In certain embodiments, the DNA polymerase in the reaction mixture may have strand-displacement activity, such that if during elongation, the primer encounters a primer or amplicon that binds to the downstream template, the strand-displacement activity of the DNA polymerase can enable separation of the downstream-binding primer from the template strand, thereby ensuring that the elongating primer continues to elongate, so that longer amplification sequences are obtained. DNA polymerases with strand-displacement activity include, but are not limited to, e.g., phi29 DNA polymerase, T5 DNA polymerase, SEQUENASE 1.0 and SEQUENASE 2.0. In certain embodiments, the DNA polymerase in the reaction mixture is a thermostable DNA polymerase. Thermostable DNA polymerases include, but are not limited to, e.g., Taq DNA polymerase, OmniBase™ Sequence enzyme, Pfu DNA polymerase, TaqBead™ Hot Start polymerase, Vent DNA polymerase (e.g., *Thermococcus litoralis* Vent polymerase, Deep Vent polymerase, Vent (-exo) polymerase and Deep Vent (-exo) polymerase), Tub DNA polymerase, TaqPlus DNA polymerase, Tfl DNA polymerase, Tli DNA polymerase, and Tth DNA polymerase. In certain embodiments, the DNA polymerase in the reaction mixture may be a DNA polymerase that is thermostable and has strand-displacement activity. In certain embodiments, the DNA polymerase in the reaction mixture is selected from the group consisting of: one or more of Phi29 DNA polymerase, Bst DNA polymerase, Pyrophage 3137, Vent polymerase (e.g., *Thermococcus litoralis* Therm polymerase, Deep Vent polymerase, Vent(-exo) polymerase, Deep Vent(-exo) polymerase), TOPOTaq DNA polymerase, 9° Nm polymerase, Klenow Fragment DNA polymerase I, MMLV reverse transcriptase, AMV reverse transcriptase, HIV reverse transcriptase, T7 phase DNA polymerase variant (lacking 3'-5' exonuclease activity), Phusion® High-Fidelity DNA polymerase, Taq polymerase, Bst DNA polymerase (full length), *E. coli* DNA polymerase, LongAmp Taq DNA polymerase, OneTaq DNA polymerase. In certain embodiments, step (b3) comprises allowing reacting at an elongation temperature between 60-90° C. (e.g., 65-90° C., 70-90° C., 75-90° C., 80-90° C., 60-85° C., 60-80° C., 60-75° C., or 60-70° C.) for 1-15 minutes (e.g., 1-14, 1-13, 1-12, 1-11, 1-10, 1-9, 1-8, 1-7, 1-6, 1-5, 1-4, 1-3, 1-2, 2-14, 3-14, 5-14, 6-14, 7-14, 8-14, 9-14, 10-14, 11-14, 12-14, or 13-14 minutes). In certain embodiments, step (b3) comprises allowing reacting at 70° C. for 2 minutes.

After the primer extension program, the reaction mixture is placed in a thermal program capable of denaturing the amplification product into single strands (step (b4)). The temperature in this step may be similar to that in step (b1), but the reaction time is shorter. In certain embodiments, step (b4) comprises allowing reacting at a temperature of 90-95° C. for 10-50 s. At this point, DNA single strands in the reaction mixture contain not only the original genomic DNA single strands, but also newly synthesized DNA single strands resulted from amplification, both of which can serve as DNA templates in the next cycle, bind to primers and initiate the next cycle of replication.

Steps (b2) to (b4) are then repeated to a designated first cycle number to obtain genomic amplification product. The first cycle number should be at least 2. In the first cycle, the sequence at 3' end of the variable sequence of the first type of primer is elongated, and the obtained amplification product has a common sequence at its 5' end and a complementary sequence of the genomic template single-strand sequence at its 3' end; such amplification products are also known as semi-amplicon. In the second cycle, the previous amplification products themselves can also serve as DNA templates to bind to the variable sequences in the first type of primers. The primer extends toward 5' end of the amplification product under the action of nucleic acid polymerase until replication of the common sequence at 5' end of the amplification product is completed, thereby obtaining a genomic amplification product having a common sequence at its 5' end and a complementary sequence of the common sequence at its 3'end; such amplification product is also referred to as full-amplicon.

In certain embodiments, the first cycle number is controlled within a suitable range to ensure sufficient amplification products for use in subsequent reactions without compromising the accuracy of amplification products due to excessive number of cycles. For example, the first cycle number is at least 3, at least 4, at least 5, or at least 6, and preferably no more than 8, no more than 9, no more than 10, no more than 11, or no more than 12. If the cycle number is too low, few amplification products are obtained, and thus, to obtain sufficient amplification products, it is necessary to increase cycle number in the next step of amplification (i.e., step (c)), which will reduce the accuracy of amplification results. While, if cycle number is too high, sequence variation may occur during genomic DNA amplification, resulting in a templates bias in the next step of amplification (i.e., step (c)), leading to an inaccurate final amplification result.

In certain embodiments, in step (b), a step (b4') is further comprised after step (b4), wherein the reaction mixture is placed in a suitable thermal program enabling hybridization of the 3' end and the 5' end of the genomic amplification product to form a loop structure, or enabling binding of the 3' end of the genomic amplification product to a primer. It was previously considered that step (b4') is capable of protecting 3' end of a full amplicon, and thereby avoids head-to-tail polymerization between full amplicons, and consequently avoids conjunction of two sequences which are originally not adjacent in a genome. This will help improve the accuracy of amplification result.

In certain embodiments, the method directly proceeds to step (b5) after step (b4), without undergoing other steps (e.g., step (b4')). In this way, full amplicons have not been subject to particular steps to avoid head-to-tail polymerization, and thus, theoretically, such amplification result should be somewhat defective with regard to accuracy. However, unexpectedly, in the method of the present application, even without a particular step after step (b4), which enables full amplicons to loop or enables binding of 3' end to a primer, the final amplification result still has considerably high accuracy, which is comparable to the effect of the method which employs step (b4'). This simplifies reaction steps while still retaining specificity of reactions.

In step (b), not only the first type of primer but also the second type of primer exists in the reaction system. The second type of primer contains the common sequence in the first type of primer. Since the common sequence is substantially not complementary to genomic sequences, if specificity of amplification reaction is high enough, the second type of primer will not directly pair with genomic DNA and initiate replication of genomic DNA in step (b). However, when step (b) has undergone two cycles, full amplicons with a complementary sequence of the common sequence at its 3' end begin to emerge in the reaction mixture, and 3' end of such full amplicons can pair with the second type of primer through base-pairing, and thus might cause replication of the full amplicons by the second type of primer starting in step (b) (e.g., starting from the third cycle). This might interfere replication of genomic DNA by the first type of primer, causing insufficient amplification of genomic DNA by the first type of primer, by which desired coverage of genomic DNA is not reached. In addition, when the first type of primer and the second type of primer exist in the reaction system at the same time, the first type of primer and the second type of primer might undergo a template-independent primer-primer amplification reaction, resulting in generation of primer polymer. However, surprisingly, despite the presence of these uncertainties described above, the inventors of the present disclosure unexpectedly found that when both the first type of primer and the second type of primer exist in the reaction mixture at the same time and both are capable of amplification reaction, the first type of primer seems not being interfered by the second type of primer, and still retains high specificity and broad coverage for genomic DNA amplification, and when comparing to the method where the first type of primer alone is used in step (b) and then the second type of primer is further added in step (c), the results obtained are overall comparable.

Step (c): Placing in a Second Thermal Cycle Program

The method provided herein further comprises step (c): placing the reaction mixture obtained from step (b) in a second thermal cycle program such that the common sequence of the second type of primer can pair with 3' end of the genomic amplification product and amplify the genomic amplification product to obtain an expanded genomic amplification product.

Since the genomic amplification product obtained from step (b), i.e. the full amplicon, has a complementary sequence to the common sequence at 3' end, it can be complementary to the common sequence of the second type of primer; under the action of nucleic acid polymerase, the second type of primer extends and full length of the full amplicon is replicated.

In the second thermal cycle program, the reaction mixture is first placed in a thermal program capable of opening DNA double strands (step (c1)). The DNA double strands herein mainly refers to the double strands of genomic amplification product (i.e., full amplicon) obtained from step (b). Although original genomic DNA still exists in the reaction mixture at this point, the original genomic DNA is not DNA template to be amplified in step (c), since the second type of primer substantially does not bind to the genomic DNA. A higher reaction temperature such as 90° C.-95° C. can be used for reaction for a suitable period as long as the full-amplicon double strands to be amplified can be denatured into single strands. In certain embodiments, the thermal program in step (c1) comprises allowing reacting for 10-30 s (e.g., 20 s) at a melting temperature between 90-95° C. (e.g., 94° C.). In certain embodiments, a step to placing the reaction mixture in a thermal program capable of opening DNA double strands and allowing reacting for sufficient time, is further comprised after the first thermal cycle program ends but before the second thermal cycle program starts. This will help ensure complete denature of template DNA double-strands into single strands.

After step (c1), the reaction mixture is placed in a thermal program that enables binding of the second type of primer to single-strands of the genomic amplification product obtained from step (b). On the basis of base composition in the second type of primer, Tm value of the second type of primer can be calculated and a suitable annealing temperature for the second type of primer can be determined based on this Tm value. In certain embodiments, thermal program in step (c2) comprises allowing reacting for 10-30 s (e.g., 15 s) at an annealing temperature between 45-65° C. (e.g., 58° C.). In certain embodiments, the second type of primer is SEQ ID NO: 1 and the thermal program in step (c2) comprises allowing reacting for 10-30 s at 58° C. In certain embodiments, the annealing temperature in step (c2) is higher than that in step (b2). In step (c2), the reaction mixture may still contain the first type of primer that did not undergo reaction in step (b), and variable sequences of these first type of primers may pair with the DNA single-strand templates obtained from step (c1), resulting in incomplete amplification sequences. When annealing temperature in step (c2) is higher than that suitable for the first type of primer, binding of the first type of primer with single-strand DNA template can be reduced or avoided, thereby selectively allowing amplification of the second type of primer.

After completion of primer annealing, the reaction mixture is placed in a thermal program that enables elongation of the second type of primer that binds to single strands of the amplification product, under the action of the nucleic acid polymerase. In certain embodiments, the thermal program in step (c3) comprises allowing reacting for 1-15 minutes (e.g., 2 minutes) at an elongation temperature between 60-80° C. (e.g., 72° C.).

Steps (c1) to (c3) can be repeated to a second cycle number to obtain the desired expanded genomic amplification product. During this process, the genomic amplification product obtained in step (b) is further replicated and amplified, the number of which is greatly increased, in order to provide sufficient genomic DNA sequences for subsequent studies or operations. In certain embodiments, the second cycle number in the step (c4) is greater than the first cycle number in the step (b5). In certain embodiments, the second cycle number is controlled within a suitable range such that it can provide sufficient amount of DNA without compromising the accuracy of amplification due to excessive number of cycles. In certain embodiments, the second cycle number is 15-30 cycles (e.g., 15-30, 15-28, 15-26, 15-24, 15-22, 15-20, 15-18, 15-17, 16-30, 17-30, 18-30, 20-30, 22-30, 24-30, 26-30, 28-30 cycles).

In certain embodiments, step (c) further comprises placing the reaction mixture in the same thermal program as that in step (c3) (e.g. 72° C.) and allowing reaction for a suitable period (e.g., 5 minutes) after the second thermal cycle program. The reaction mixture is then placed at a temperature of 4° C. to terminate reaction. In certain embodiments, the reaction mixture is placed at a temperature of 4° C. to terminate reaction directly after completion of the reaction of step (c).

In certain specific embodiments, the present application also provides a method for amplifying genome of a cell comprising:

(a) providing a reaction mixture, wherein the reaction mixture comprises DNA of said genome DNA, a first type of primer, a second type of primer, a mixture of nucleotide monomers, and a nucleic acid polymerase, wherein the first type of primer comprises, in a 5' to 3' orientation, a common sequence and a variable sequence, wherein the common sequence consists of three or two types of bases selected from the group consisting of four types of bases: G, A, C and T, providing that the common sequence does not comprise G and C at the same time, and wherein the second type of primer comprises the common sequence but not the variable sequence;

(b) placing the reaction mixture in a first thermal cycle program such that the variable sequence of the first type of primer can pair with the DNA of the genome and amplify the DNA of the genome to obtain a genomic amplification product, wherein the genomic amplification product comprises the common sequence at its 5' end and comprises complementary sequence of the common sequence at its 3' end; wherein the first thermal cycle program comprises:

(b1) allowing reacting at a first denaturation temperature between 90-95° C. for 1-10 minutes;

(b2) allowing reacting at a first annealing temperature between 5-10° C. for 3-50 s, at a second annealing temperature between 25-30° C. for 3-50 s, and at a third annealing temperature between 45-50° C. for 3-50 s;

(b3) allowing reacting at a first elongation temperature between 60-90° C. for 1-15 minutes;

(b4) allowing reacting at a first melting temperature between 90-95° C. for 10-50 s;

(b5) repeating steps (b2) to (b4) to 6-9 cycles;

(c) placing the reaction mixture obtained from step (b) in a second thermal cycle program, such that the common sequence of the second type of primer can pair with 3' end of the genomic amplification product and amplify the genomic amplification product to obtain an expanded genomic amplification product, wherein the second thermal cycle program comprises:

(c1) allowing reacting at a second denaturation temperature between 90-95° C. for 1-10 minutes;

(c2) allowing reacting at a second melting temperature between 90-95° C. for 10-30 s;

(c3) allowing reacting at a fourth annealing temperature between 45-65° C. for 10-30 s;

(c4) allowing reacting at a second elongation temperature between 60-80° C. for 1-15 minutes;

(c5) repeating steps (c2) to (c4) for 5-30 cycles;

(d) obtaining amplification product from the step (c);

wherein the reaction mixture is provided prior to the step (b) and the step (c).

In certain embodiments, genomic DNA in the reaction mixture in step (a) is present within a cell, i.e., the reaction mixture contain cells in which the genomic DNA to be amplified is contained. In certain embodiments, the reaction mixture in step (a) contains cells and further comprises components capable of lysing cells, such as surfactant and/or lyase, etc. Suitable surfactants, such as one or more of NP-40, Tween, SDS, TritonX-100, EDTA, and guanidine isothiocyanate, can be used. Suitable lyases, such as one or more of Protease K, pepsin and papain, can also be selected. In such embodiments, the method of amplifying cell genome as described above further comprises placing a reaction mixture in a lysing thermal cycle program after step (a) and prior to step (b) (e.g., placing a reaction mixture at 50° C. for 20 minutes, then at 80° C. for 10 minutes), to allow lysing of the cell and release of the genomic DNA. In this way, the entire amplification reaction actually involves allowing cell lysing and genome amplification to occur in the same reaction mixture, and is achieved by placing a reaction mixture in different thermal cycle programs. This greatly simplifies the procedure, avoids the risk of contamination brought by multiple sample manipulations, and also achieves good amplification specificity and low variability concerning amplification result.

In certain embodiments, the first type of primer comprises or consists of SEQ ID NO: 11, 12, 13, 14, and/or 15, wherein the common sequence comprises or consists of SEQ ID NO: 1.

Advantages

The method provided by the present application has several advantages over the methods in prior art.

In one aspect, the present disclosure combines steps of nucleic acid pre-amplification, amplification, etc. into one reaction, under thermal cycle condition. This reaction reduces manual operation, and whole genome amplification of nucleic acid can be accomplished simply by placing nucleic acid into a PCR tube and performing specific program, the amplification products of which have a high degree of genome coverage and low amplification bias. Operations of reagent preparation, and liquid addition with open lid are eliminated, and risks of contamination resulted from experimental environment and operators are reduced, and meanwhile, the overall experimental time period is shortened, with the overall amplification time being only 2.5 hours.

In another aspect, the present disclosure can also combine steps of cell lysing, nucleic acid pre-amplification and amplification etc. into one reaction, under thermal cycle condition, which further reduces manual operations and eliminates the step in which cells are separately lysed, and further shortens experimental time and reduces risks of contamination.

The method of the present application also retains high accuracy and broad coverage of amplification, in addition to simplified operations. The method of the present application uses quasi-linear amplification technique to reduce sequence-dependent amplification bias. In pre-amplification, a focus is on amplification from original sample DNA template, and with a high genome coverage and a small amplification bias. Full amplicons generated during pre-amplification phase are amplified in large number during amplification phase. Amplification process by such technique has high yield, with a minimum initial template of a few picograms, and the results are reliable and reproducible.

Application

In certain embodiments, the product obtained by amplification using the method of the present application can be further used for sequencing, such as for whole genome sequencing. Due to the high requirement on initial amount of samples to be analyzed (more than 100 ng) by various sequencing analysis platforms such as Next Generation Sequencing (NGS), Microarray, and fluorescent quantitative PCR, etc., whole genome amplification is needed if sufficient nucleic acid material for analysis need to be obtained from a single human cell (about 6 pg) or a sample in a small initial amount. Genomic DNA in a biological sample (e.g., a single cell) can be amplified by the method of the present application, and the product obtained from amplification can be sequenced by a suitable sequencing method in the art. Exemplary sequencing methods include, sequencing by hybridization (SBH), sequencing by ligase (SBL), quantitative incremental fluorescent nucleotide addition sequencing (QIFNAS), stepwise ligation and cleavage, molecular beacons, pyrosequencing, fluorescent in situ sequencing (FISSEQ), fluorescence resonance energy transfer (FRET), multiplex sequencing (U.S. patent application Ser. No. 12/027, 039; porreca et al. (2007) NAT. Methods 4:931), polymerized colony (POLONY) sequencing (U.S. Pat. No. 6,432,360, U.S. Pat. No. 6,485,944 and PCT/US05/06425); swing sequencing (PCT US05/27695), TaqMan reporter probe digestion, nanogrid rolling circle sequencing (ROLONY) (U.S. patent application Ser. No. 12/120,541), FISSEQ beads (U.S. Pat. No. 7,425,431), and allele-specific oligonucleotide ligation assay, etc.

In certain embodiments, sequencing of amplification products of the method herein can be accomplished by high-throughput method. High-throughput methods typically fragmentize nucleic acid molecules to be sequenced (e.g., by means of enzymatic cleavage or mechanical shearing, etc.), to form large amount of short fragments ranging from tens to hundreds of bp in length. By sequencing tens of thousands, hundreds of thousands, millions, tens of millions, or even hundreds of millions of such short fragments in parallel in one sequencing reaction, throughput of sequencing can be greatly increased and time required for sequencing can be shortened. The measured sequences of short fragments can be joined into a complete sequence after data processing via software. A variety of high-throughput sequencing platforms are known in the art, such as Roche 454, Illumina Solexa, AB-SOLiD, Helicos, and Polonator platform technology, and the like. A variety of light-based sequencing techniques are also known in the art, see, e.g., those described in Landegren et al. (1998) Genome Res. 8: 769-76, Kwok (2000) Pharmacogenomics 1: 95-100, and Shi (2001) Clin. Chem. 47: 164-172.

In certain embodiments, products obtained from amplification using the method of the present application can also be used to analyze genotypes or genetic polymorphisms in genomic DNA, such as single nucleotide polymorphism (SNP) analysis, short tandem repeat (STR) analysis, restriction fragment length polymorphism (RFLP) analysis, variable number of tandem repeats (VNTRs) analysis, complex tandem repeat (CTR) analysis, or microsatellite analysis and the like, see, e.g., Krebs, J. E., Goldstein, E. S. and Kilpatrick, S. T. (2009). Lewin's Genes X (Jones & Bartlett Publishers) for reference, which is incorporated herein by reference in its entirety.

In certain embodiments, amplification products obtained by the method of the present application can also be used for medical and/or diagnostic analysis. For example, a biological sample from an individual may be amplified using the method of the present application, and whether abnormalities such as mutations, deletions, insertions or fusion between chromosomes are present in gene or DNA sequence of interest in the amplification product can be analyzed, whereby to evaluate the risk of developing certain disease for the individual, the progression stage, genotyping and severity of the disease, or the likelihood that the individual respond to certain therapy. The gene or DNA sequence of interest can be analyzed using suitable methods known in the art, such as, but not limited to, nucleic acid probe hybridization, primer-specific amplification, sequencing a sequence of interest, single-stranded conformational polymorphism (SSCP), etc.

In certain embodiments, the methods of the present application can be used to compare genomes derived from different single cells, in particular different single cells from the same individual. For example, when differences exist between genomes of different single cells of the same individual, such as between tumor cells and normal cells, genomic DNA of different single cells can be amplified separately using the method herein, and the amplification product can be further analyzed, for example, analyzed and compared by sequencing, or subject to comparative genomic hybridization (CGH) analysis. See, Fan, H. C., Wang, J., Potanina, A., and Quake, S. R. (2011). Whole-genome molecular haplotyping of single cells. Nature Biotechnology 29, 51-57., and Navin, N., Kendall, J., Troge, J., Andrews, P., Rodgers, L., Mclndoo, J., Cook, K., Stepansky, A., Levy, D., Esposito, D., et al. (2011). Tumour evolution inferred by single-cell sequencing. Nature 472, 90-94, for reference, all of which are incorporated herein by reference in their entirety.

In certain embodiments, the methods of the present application can be used to identify haploid structures or haploid genotypes in homologous chromosomes. Haploid genotype refers to the combination of alleles at multiple loci that are co-inherited on chromosome of the same haplotype. A biological sample (e.g., a single cell from an individual's diploid) can be divided into enough portions so that DNA sequences on two homologous haplotypes are statistically separated into different portions. Each section is assigned as one reaction mixture, and each reaction mixture is subjected to DNA amplification by the method of the present application, and then the amplification product is subjected to sequence analysis and is aligned with a reference genomic sequence (e.g., publically available standard genomic sequence of humans, see, International Human Genome Sequencing Consortium, Nature 431, 931-945 (2004)), to identify single nucleotide mutations therein. If no reference genome sequence is readily available, a region of suitable length assembled from multiple fragment sequences of genome by means of de-novo genome assembly can also be used for comparison.

In certain embodiments, products obtained from amplification using the method of the present application can be further used for analysis such as gene cloning, fluorescence quantitative PCR and the like.

In certain embodiments, the method of the present application can also further comprise analyzing the amplification product to identify disease- or phenotype-associated sequence features. In some embodiments, analyzing the amplification product comprises genotyping of DNA amplicon. In some other embodiments, analyzing the amplification product includes identifying polymorphism of DNA amplicons, such as single nucleotide polymorphism (SNP) analysis. SNP can be detected by some well-known methods such as oligonucleotide ligation assay (OLA), single base extension, allele-specific primer extension, mismatch hybridization and the like. A disease can be diagnosed by comparison of SNP to those of known disease phenotypes.

In some embodiments, the disease- or phenotype-associated sequence features include chromosomal abnormalities, chromosomal translocation, aneuploidy, deletion or duplication of a part of or all chromosomes, fetal HLA haplotypes and paternal mutations.

In some embodiments, the disease or phenotype may be beta-thalassemia, Down's syndrome, cystic fibrosis, sickle cell disease, Tay-Sachs disease, Fragile X syndrome, spinal muscular atrophy, hemoglobinopathy, Alpha-thalassemia, X-linked diseases (diseases dominated by genes on the X chromosome), spinal bifida, anencephaly, congenital heart disease, obesity, diabetes, cancer, fetal sex, and fetal RHD.

Kit

Another aspect of the application also provides a kit for genomic DNA amplification, wherein the kit comprises a mixture containing a first type of primer and a second type of primer, wherein the first type of primer comprises, in a 5' to 3' orientation, a common sequence and a variable sequence, wherein the common sequence consists of three or two types of bases selected from the group consisting of four types of bases: G, A, C and T, providing that the common sequence does not comprise G and C at the same time, and the second type of primer comprises the common sequence but not the variable sequence.

In certain embodiments, wherein the mixture further comprises a mixture of nucleotide monomers (e.g., dATP, dGTP, dTTP, and dCTP), dTT and $Mg^{2+}$. In certain embodiments, Mg2+ concentration in the mixture is between 2 mmol-8 mmol/μL, dNTP concentration is between 1 mmol-8 mmol/μL and dTT concentration is between 2 mmol-7 mmol/μL. In certain embodiments, the mixture further comprises one or more components selected from the group consisting of: bovine serum albumin (BSA), a pH-regulator (e.g., Tris HCl), DNase inhibitor, RNase, $SO_4^{2-}$, $Cl^-$, $K^+$, $Ca^{2+}$, Na+, and/or $(NH_4)^+$ and the like. In certain embodiments, pH value range of the mixture is between 7.0-9.0.

In certain embodiments, the kit further comprises a nucleic acid polymerase, and the nucleic acid polymerase is not contained in the mixture of the first type of primer and the second type of primer. In such embodiments, the nucleic acid polymerase can be stored in a separate container, optionally forming a mixture with other components, or being present in a substantially pure form.

In certain embodiments, the mixture of first type of primer and second type of primer further comprises a nucleic acid polymerase. In certain embodiments, the mixture comprises: a first type of primer, a second type of primer, a mixture of nucleotide monomers, $Mg^{2+}$, dTT, Tris HCl and a nucleic acid polymerase, and one or more components selected from the group consisting of: BSA, DNase inhibitor, RNase, $SO_4^{2-}$, $Cl^-$, $K^+$, $Ca^{2+}$, Na+, and $(NH_4)^+$, etc. In such embodiment, the mixture may contain all reactants required for amplification reaction except genomic DNA. When such mixture is used in the amplification reaction of the present application, reagents containing genomic DNA may be directly mixed with the mixture in the kit, and optionally, a proper amount of pure water may be added to obtain required reaction volume, then the reaction mixture in step (a) of the method of the present application can be obtained.

In certain embodiments, a kit further comprises a component capable of lysing a cell, such as one or more surfactants, and/or one or more lyases. Exemplary surfactants include, but are not limited to, one or more of NP-40, Tween, SDS, TritonX-100, EDTA, and guanidinium isothiocyanate. Exemplary lyases can be one or more of Protease K, pepsin, and papain. The component that lyses a cell can be stored separately in a separate container, or mixed with other components. In certain embodiments, a kit comprises a surfactant and a lyase, placed separately in different containers, or placed in the same container.

In certain embodiments, the mixture of first type of primer, second type of primer, and nucleic acid polymerase further comprises a surfactant and/or a lyase.

In certain embodiments, the kit comprises one container, wherein all of the reagents are contained. In certain embodiments, the kit comprises two containers, wherein one container stores components required in amplification reaction including nucleic acid polymerase, and the other container stores components required in cell lysing including lyase. In certain embodiments, the kit comprises four containers, wherein a first container stores nucleic acid polymerase, a second container stores components required in amplification reaction other than nucleic acid polymerase, a third container stores lyase, and a fourth container stores components required in cell lysing other than lyase.

Another aspect of the application also provides a kit for genomic DNA amplification, comprising a first type of primer and a second type of primer, and further comprises an instruction for users, said instruction records the following steps: mixing the first type of primer and the second type of primer in the same container before said amplifying, wherein the first type of primer comprises, in a 5' to 3' orientation, a common sequence and a variable sequence, wherein the common sequence consists of three or two types of bases selected from the group consisting of four types of bases: G, A, C and T, providing that the common sequence does not comprise G and C at the same time, and wherein the second type of primer comprises the common sequence but not the variable sequence. The first type of primer and the second type of primer in the kit may be placed separately in different containers, but the instruction may include the step of mixing the two in the same container before amplification.

EXAMPLES

Example 1: Obtaining Single-Cell Genome, Positive Control and Negative Control

Single-cell genomic DNA: Cultured human epidermal fibroblasts (AFP) in a good state were digested with trypsin and the digested cells were collected into a 1.5 ml EP tube. The collected cells were centrifuged and rinsed with 1×PBS solution. After rinsing, 1×PBS was added to suspend the cells. A portion of the cell-containing suspension was aspirated using a pipette, and single cells were picked using a mouth pipette under a 10× microscope, the volume of aspirated PBS solution not exceeding 1 microliter, and the picked single cells were transferred into a PCR tube containing 4 microliters of lysis buffer (containing Tris-Cl, KCl, EDTA, Triton X-100 and Qiagen Protease). After brief centrifugation, the PCR tube was placed on a PCR instrument where a lysing program was performed, and the specific program is shown in Table 1.

TABLE 1

| Lysing program | | |
|---|---|---|
| Cycle number | Temperature (centigrade) | Time |
| 1 | 50 | 20 min |
| | 80 | 10 min |
| | 4 | Maintained |

Positive control: standard genomic DNA was diluted to 30 pg/μl DNA solution with nuclease-free water, and 1 μl of the solution above was added to a PCR tube containing 4 μl cell lysis buffer. The standard genomic DNA was genomic DNA of human cells extracted previously.

Negative control: 5 μl of cell lysis buffer was added to a PCR tube.

Example 2: Genome Amplification Using Multiple Annealing and Looping-Based Amplification Cycles (MALBAC) (Referred to as Three-Step Method)

The method of the present example is also referred to as three-step method herein, since it basically comprises three steps, namely, lysing cells, pre-amplification, and exponential amplification.

Human epidermal fibroblasts were isolated and lysed according to the method described in Example 1, to obtain single-cell genomic DNA. Single cell whole genome amplification kit of Jiangsu Yikon Genomics Co., Ltd. (Cat. No. YK001A/B) was used, and amplification was performed pursuant to its manufacturer's instructions. Specifically, a pre-amplification buffer and a pre-amplification enzyme mixture were mixed in a ratio of 30:1 to generate a pre-amplification mixture. 30 μl of pre-amplification mixture was added respectively to PCR tubes each containing samples to be amplified (genomic DNA, positive control and negative control obtained according to Example 1). The PCR tubes were placed into a PCR instrument for pre-amplification, and the pre-amplification program is shown in Table 2.

TABLE 2

| pre-amplification program for MALBAC three-step method | | |
|---|---|---|
| Cycle number | Temperature (centigrade) | Time |
| 1 | 94 | 3 min |
| 8 | 20 | 40 s |
| | 30 | 40 s |
| | 40 | 30 s |
| | 50 | 30 s |
| | 60 | 30 s |
| | 70 | 4 min |

TABLE 2-continued pre-amplification program for MALBAC three-step method

| Cycle number | Temperature (centigrade) | Time |
|---|---|---|
|  | 95 | 20 s |
|  | 58 | 10 s |
| 1 | 4 | Maintained |

An amplification buffer and an amplification enzyme mixture were mixed in a ratio of 30:0.8 to generate an amplification mixture. 30 µl of the amplification mixture was added to a PCR tube where pre-amplification has completed, followed by exponential amplification, the program for which is shown in Table 3.

TABLE 3 exponential amplification program for MALBAC three-step method

| Cycle number | Temperature (centigrade) | Time |
|---|---|---|
| 1 | 94 | 30 s |
| 17 | 94 | 20 s |
|  | 58 | 30 s |
|  | 72 | 3 min |
| 1 | 4 | Maintained |

Example 3: Genomic Amplification Using Mixed Primers (Referred to as Two-Step Method)

The method of the present example is also referred to as two-step method herein, basically comprising two steps, namely, lysing cells and amplification reaction.

Human epidermal fibroblasts were isolated and lysed according to the method described in Example 1, to obtain single-cell genomic DNA.

An amplification mixture was prepared, containing $Na^+$, $Mg^{2+}$, $Cl^-$, Tris-Cl, TritonX-100, dNTP, Vent polymerase, primer of SEQ ID NO: 1, primer of SEQ ID NO: 12, and primer of SEQ ID NO: 13.

Primers used in this example were designed according to the following principles:

1. Common sequence of a primer only contains three types of bases with weak self-complementary pairing ability, such as G, A and T.

2. One or more of the three types of bases mentioned in 1 are used at 3' end of primer variable base sequence (three or more bases that are successive or unsuccessive), to ensure that phenomenon of self-complementary pairing or complementary pairing with 5' end of a different primer will not occur to the 3' end of the primer.

3. By statistical calculation of recognition sites of primer variable base sequences on genome, sequences that meet the above conditions above, are more evenly distributed on genome and with higher coverage, are selected, to increase opportunity of recognition between variable base sequence and genomic DNA.

4. The use ratio and composition of the three types of bases in primer common sequence are specially designed to ensure that the common sequence will not bind to genomic DNA and generate amplification. 60 µl of amplification mixture is added to PCR tubes of each sample to be amplified (genomic DNA, positive control and negative control obtained according to Example 1), respectively. The PCR tubes were placed into a PCR instrument for amplification, and the amplification program is shown in Table 4.

TABLE 4 amplification program for the two-step method of the present application

| Cycle number | Temperature (centigrade) | Time |
|---|---|---|
| 1 | 94 | 3 min |
| 8 | 10 | 20 s |
|  | 30 | 30 s |
|  | 50 | 40 s |
|  | 70 | 2 min |
|  | 95 | 20 s |
| 1 | 94 | 30 s |
| 17 | 94 | 20 s |
|  | 58 | 15 s |
|  | 72 | 2 min |
| 1 | 72 | 5 min |
|  | 4 | maintained |

Example 4: Comparison of Amplification Product from the Two-Step Method and Amplification Product from the MALBAC Three-Step Method of the Present Application Gel Electrophoresis 5 microliters of unpurified amplification product from the three-step method of Example 2 and unpurified amplification product from the two-step method of Example 3 were taken, respectively, and were respectively added with 1 microliter of 6×DNA loading buffer (purchased from Beijing ComWin Biotech Co., Ltd., Cat. No. CW0610A) for sample loading. 1% agarose gel was used as the gel, and DM2000 (purchased from Beijing ComWin Biotech Co., Ltd., Cat. No. CW0632C) was used as the marker.

Figure 2:
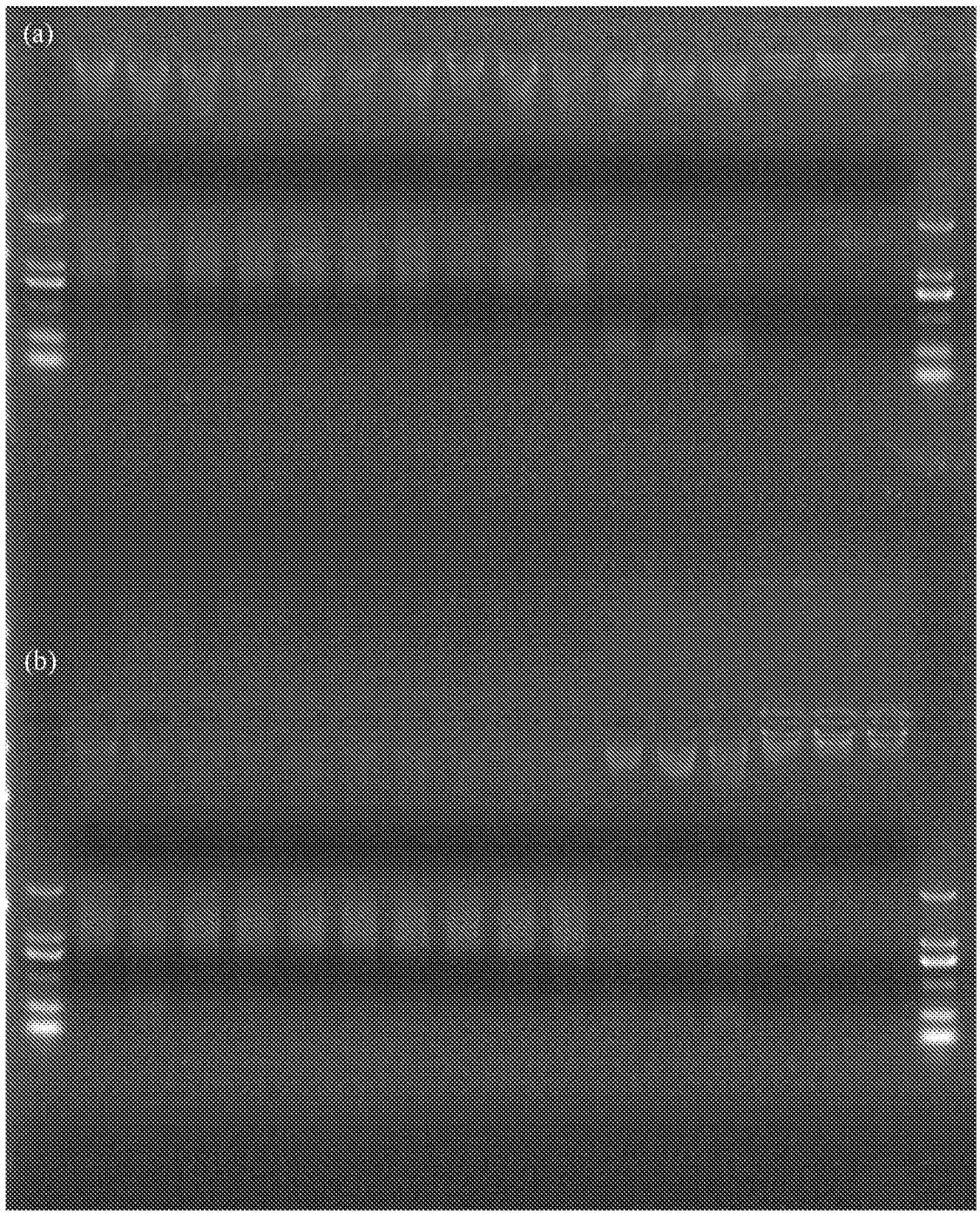
FIG. 2 shows gel electrophoresis results of amplification products obtained by amplifying genomic DNA of normal human epidermal fibroblasts (AFP) using the three-step method of Example 2 and the two-step method of Example 3, respectively, wherein (a) shows amplification results of the two-step method of Example 3 (from left to right, lane 1, molecular-weight marker; lanes 2-11, single-cell amplification samples; lanes 12-14, positive control (40 pg gDNA); Lanes 15-17, negative control; lane 18, molecular-weight marker); (b) shows amplification results of the three-step method of Example 2 (from left to right, lane 1, molecular-weight marker; lanes 2-11, single-cell amplification samples; lanes 12-14, positive control (40 pg gDNA); lanes 15-17, negative control; lane 18, molecular-weight marker).

See FIG. 2 for electrophoresis results, wherein (a) is the amplification results of the two-step method of Example 3 (from left to right, lane 1, molecular-weight marker; lanes 2-11, single-cell amplification samples; lanes 12-14, positive control (40 pg gDNA); Lanes 15-17, negative control (free of genomic DNA); lane 18, molecular-weight marker); (b) is the amplification results of the three-step method of Example 2 (from left to right, lane 1, molecular-weight marker; lanes 2-11, single-cell amplification samples; lanes 12-14, positive control (40 pg gDNA); Lanes 15-17, negative control (free of genomic DNA); lane 18, molecular-weight marker). The electrophoresis shows that: the band position and brightness of the two-step amplification product of Example 3 were comparable to those of the three-step amplification product of Example 2, with no significant difference, indicating that the accuracy and yield of product of the two-step amplification are comparable to the results of the three-step method.

Purification Product 50 microliters of unpurified amplification products from the three-step method of Example 2 and from the two-step method of Example 3 were taken, and the amplification products were purified with a universal column purification kit (purchased from Beijing ComWin Biotech Co., Ltd., Cat. No. CW2301), the purification steps of which were performed in accordance with the kit instructions. 50 microliters of EB was used for elution. After purification was completed, 2 µl of the purified product was subject to concentration measurement using Nanodrop (AOSHENG, NANO-100). Results of concentration measurement are shown in Table 5.

TABLE 5

Concentration of amplification products after purification

| Two-step method | Concentration (ng/μl) | Three-step method | Concentration (ng/μl) |
|---|---|---|---|
| 2-1 | 69.668 | 3-1 | 60.146 |
| 2-2 | 57.332 | 3-2 | 67.512 |
| 2-3 | 44.119 | 3-3 | 71.704 |
| 2-4 | 57.859 | 3-4 | 75.275 |
| 2-5 | 73.391 | 3-5 | 67.615 |
| 2-6 | 70.341 | 3-6 | 79.219 |
| 2-7 | 71.845 | 3-7 | 86.552 |
| 2-8 | 44.211 | 3-8 | 79.712 |
| 2-9 | 60.947 | 3-9 | 65.838 |
| 2-10 | 90.09 | 3-10 | 64.263 |
| Mean | 63.98 | Mean | 71.78 |

Concentration measurement results show that: post-purification concentration of amplification products obtained by the two amplification methods were comparable, with no significant difference.

Detection of Disease-Causing Sites 20 pathogenic sites were randomly selected (see the table below for selected sites) and primers were designed. Selected pathogenic sites and their corresponding primers are shown in Table 6 and Table 7, respectively.

TABLE 6

First batch of pathogenic sites

| No. | Name of pathogenic sites | Chromosome location |
|---|---|---|
| 1 | PKHD1-3681 | chr6 |
| 2 | PKHD1-1713 | chr6 |
| 3 | WASP-C21 | chrX |
| 4 | WASP-C12 | chrX |
| 5 | DMD-13exe | chrX |
| 6 | DMD-19exe | chrX |
| 7 | ATP7B-8 | chr13 |
| 8 | ATP7B-13 | chr13 |
| 9 | ERCC6-C643 | chr10 |
| 10 | ERCC6-C3776 | chr10 |
| 11 | GJB2 | chr13 |
| 12 | GJB2-c79 | chr13 |
| 13 | PDS-7 + 8 | chr7 |
| 14 | PDS-10 | chr7 |
| 15 | CFTR-PL88 | chr17 |
| 16 | CFTR-IVS13 | chr17 |
| 17 | IL2RG | chrX |
| 18 | IL2RGIVS4 | chrX |
| 19 | FLG-c3319 | chr1 |
| 20 | IDS | chrX |

TABLE 7

Corresponding primers of the first batch of pathogenic sites

| Name of pathogenic sites | Primer sequences |
|---|---|
| PKHD1-3681+ | AGTGATTGTCATTGAAATTGGTGATTC |
| PKHD1-3681− | AGCCAATGACTCCCTTTGAC |
| PKHD1-1713+ | CAGAGCGATGACATCTTAACCT |
| PKHD1-1713− | GTGAACACCAGGGCAGATGAG |
| WASP-C21+ | TGTCCCTTGTGGTTTTTTGCATTTC |
| WASP-C21− | TTTCGTCCAAGCATCTCAAAGAGTC |
| WASP-C12+ | CTCTTCTTACCCTGCACCCAGAG |
| WASP-C12− | GCATTTTCGTCCAAGCATCTCAAAGAG |
| DMD-13exe+ | AAGAACAAGTCAGGGTCAAT |
| DMD-13exe− | TTAAAATACTTTTCAAGTTATAGTTCTTTT |
| DMD-19exe+ | GTGAAACATCTTAAGGCTTGAAAG |
| DMD-19exe− | TAACAAGTGCTTGTCTGATATAAT |
| ATP7B-8+ | AAAAGCTGAGAAGTTCAGAAAAC |
| ATP7B-8− | AAATTTGTATTTAACAAGTGCTTGTC |
| ATP7B-13+ | GTTTATTCTCTGGTCATCCTGGT |
| ATP7B-13− | GGTGTTCAGAGGAAGTGAGATT |
| ERCC6-C643+ | GAACTCTCAACCTGCCTCTG |
| ERCC6-C643− | CTTGATGAGGATGCCGTTCT |
| ERCC6-C3776+ | CCATTCAAGGAACAACAGCTAAA |
| ERCC6-C3776− | ACCCAGGCAAAGACTAAAGAG |
| GJB2+ | GACGCCAAGTTTGAAGGAAC |
| GJB2− | CTACTGCTAGAAACAGCCTACTC |
| GJB2-c79+ | TCGCATTATGATCCTCGTTG |
| GJB2-c79− | GGACACAAAGCAGTCCACAG |
| PDS-7+8+ | AAGTCTCCCTGTTCTGTCCTA |
| PDS-7+8− | AGGGTGTTGCAGACAAAGT |
| PDS-10+ | TTCACTGCTGGATTGCTCAC |
| PDS-10− | CCCCTTGGGATGGATTTAAC |
| CFTR-PL88+ | AAATCCCAGTCCCTATTCCTAT |
| CFTR-PL88− | CTAAGAGGAACACCACACTCAC |
| CFTR-IVS13+ | TTTGCAGAGAATGGGATAGAGAG |
| CFTR-IVS13− | CACCTATTCACCAGATTTCGTAGT |
| IL2RG+ | TGACCAGGAAATAGAGAGGAAATG |
| IL2RG− | CATTCTGCCATACCAACAATGG |
| IL2RG IVS4+ | ATTGGAAGCCGTGGTTATCTC |
| IL2RG IVS4− | CTTCCATCACCAAACCCTCTT |
| FLG-c3319+ | CTGAGTGAATCCCAGCTAGAAC |
| FLG-c3319− | GCAGAGAACAGGAGCTTGAT |
| IDS+ | CTCCAGACACTCAGGCATTC |
| IDS− | GTGCTCACCTGGTAGATGAAA |

7 amplification products amplified according to Example 2 and 7 amplification products amplified according to Example 3 were randomly selected as template DNA, respectivey. The 20 pathogenic sites above were respectively amplified by PCR using dye-containing 2×Taq MasterMix (purchased from Beijing ComWin Biotech Co., Ltd., Cat. No. CW0682). Composition of amplification system is shown in Table 8, and amplification program is shown in Table 9.

TABLE 8

PCR reaction system for detecting pathogenic sites

| | |
|---|---|
| 2 × Taq MaterMix | 25 μl |
| Forward primer, 10 μM | 2 μl |
| Reverse primer, 10 μM | 2 μl |
| Template DNA | 40 ng |
| RNase-free water | Add to a final volume of 50 μl |

TABLE 9

PCR amplification program for detecting pathogenic sites

| Cycle number | Temperature (centigrade) | Step | Time |
|---|---|---|---|
| 1 | 95 | Pre-denaturation | 10 min |
| 40 | 95 | Denaturation | 30 s |
|  | 55/50* | Anneal | 30 s |
|  | 72 | Extension | 60 s |
| 1 | 72 | Final extension | 5 min |

*Annealing temperature for PKDH1-3681, PKDH1-1713, DMD-13exe, and DMD-19exe was 50° C., and that for the remaining 16 primers was 55° C.

Figure 3:
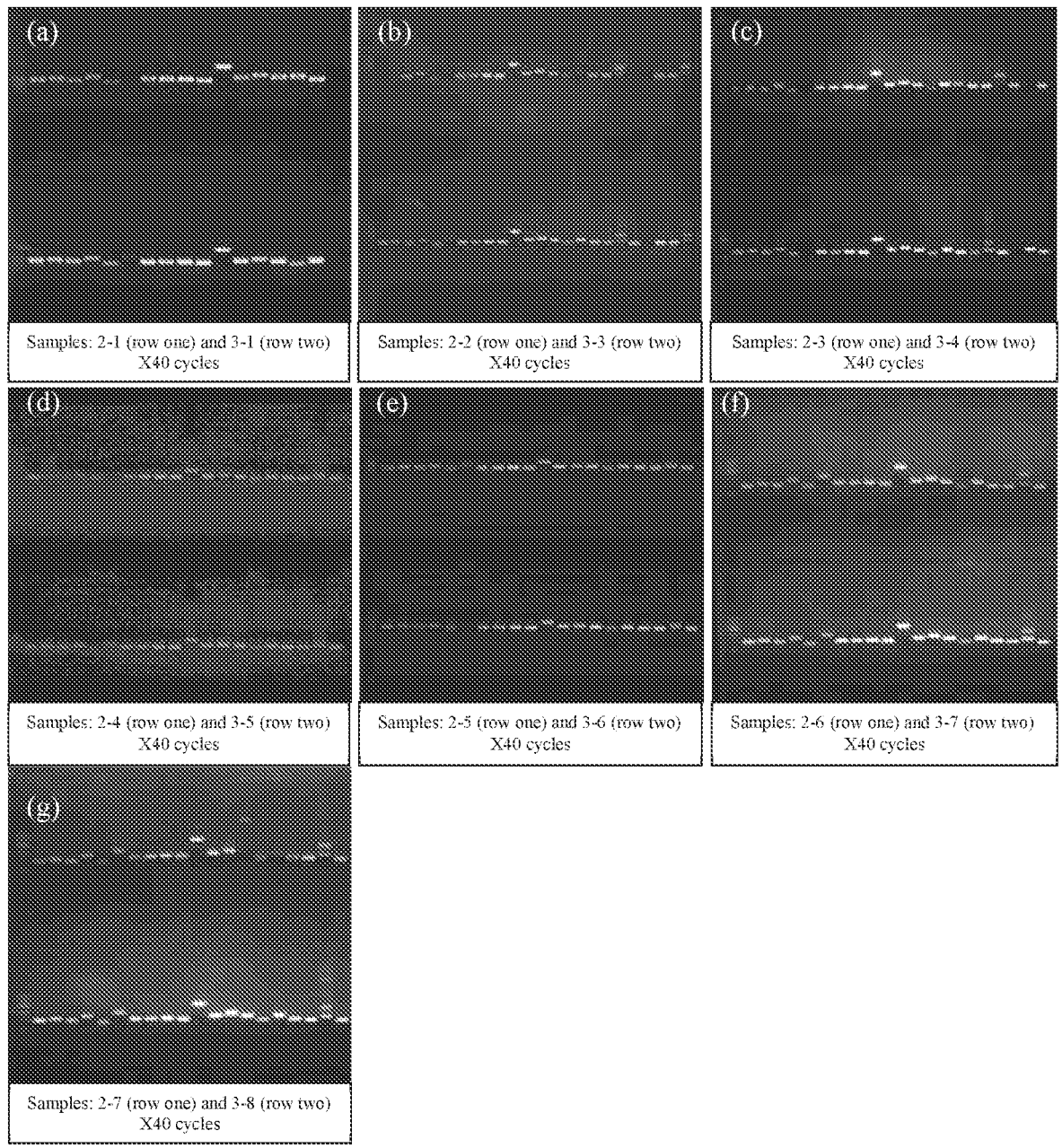
FIG. 3 shows gel electrophoresis results of the following: genomic DNA of normal human epidermal fibroblasts (AFP) was amplified using the three-step method of Example 2 and the two-step method of Example 3, respectively, and 7 samples were randomly selected from the amplification products obtained from the two methods (i.e., a total of 14 samples) as template, respectively, and the 20 pathogenic sites shown in Table 6 were amplified using primers shown in Table 7, and the amplification products were subject to gel electrophoresis. a-g therein represent gel electrophoresis images of re-amplified products of the single-cell genomic DNA amplification products, respectively, wherein the upper-row bands indicate results of amplification using the two-step method and the lower-row bands indicate results of amplification using the three-step method (a: Upper-row corresponds to sample 2_1 and lower-row corresponds to sample 3_1; b: Upper-row corresponds to sample 2_2 and lower-row corresponds to sample 3_3; c: Upper-row corresponds to sample 2_3 and lower-row corresponds to sample 3_4; d: Upper-row corresponds to sample 2_4 and lower-row corresponds to sample 3_5; e: Upper-row corresponds to sample 2_5 and lower-row corresponds to sample 3_6; f: Upper-row corresponds to sample 2_6 and lower-row corresponds to sample 3_7; g: Upper-row corresponds to sample 2_7 and lower-row corresponds to sample 3_8). In each electrophoresis image, from left to right, lanes sequentially indicate molecular-weight marker, and results of amplification of pathogenic sites 1-20 shown in Table 6 (amplification of pathogenic sites 1-16 in Figure (a)).

Amplification results are shown in FIG. 3. The amplification results shows that: there was no significant difference in amplification accuracy and amount of amplification products between the two methods.

Another 20 pathogenic sites were further randomly selected (see the table below for the selected sites) and primers were designed. The selected pathogenic sites and their corresponding primers are shown in Table 10 and Table 11, respectively.

TABLE 10

The second batch of pathogenic sites

| No. | Name of pathogenic sites | Chromosome location |
|---|---|---|
| 1 | SMN1-1 | chr5 |
| 2 | SMN1-2 | chr5 |
| 3 | SMN1-3 | chr5 |
| 4 | SMN1-4 | chr5 |
| 5 | SMN1-1R | chr5 |
| 6 | SMN1-2R | chr5 |
| 7 | SMN1-3R | chr5 |
| 8 | SMN1-4R | chr5 |
| 9 | PDS-IV15 | chr7 |
| 10 | PDS-EXON5 | chr7 |
| 11 | PDS-EXON7 + 8 | chr7 |
| 12 | PDS-EXON10 | chr7 |
| 13 | PDS-EXON17 | chr7 |
| 14 | PDS-EXON19 | chr7 |
| 15 | HBB | chr11 |
| 16 | HBB3 | chr11 |
| 17 | MMA CHC | chr1 |
| 18 | HBA2 | chr16 |
| 19 | GJB2 | chr13 |
| 20 | GJB2-C796 | chr13 |

TABLE 11

Corresponding primers to the second batch of pathogenic sites

| Name of pathogenic site | Primer sequences |
|---|---|
| SMN1-1+ | AAAATGTCTTGTGAAACAAAATGC |
| SMN1-1- | TTTTACAAAAGTAAGATTCACTTTCATAAT |
| SMN1-2+ | AGGGTTTCAGACAAAATCAAAAGAAG |
| SMN1-2- | CTAATAGTTTTGGCATCAAAATTCTTTAAT |
| SMN1-3+ | CTTTATGGTTTGTGGAAAACAAATG |
| SMN1-3- | GTCTGCCTACTAGTGATATAAAATGG |
| SMN1-4+ | CTGGAATGTGAAGCGTTATAG |
| SMN1-4- | CAAAATCTAATCCACATTCAAATTTT |
| SMN1-1R+ | TGTGGGATTGTAGGCATGAG |
| SMN1-1R- | GCTGGCAGACTTACTCCTTAAT |
| SMN1-2R+ | AAGTCTGCCAGCATTATGAAAG |
| SMN1-2R- | CCACATAACCAACCAGTTAAG |
| SMN1-3R+ | GTTCAGATGTTAAAAAGTTGAAAG |
| SMN1-3R- | TGGTCTGCCTACTAGTGATATAAA |
| SMN1-4R+ | GGAAGTGGAATGGGTAACTCTT |
| SMN1-4R- | CCACATACGCCTCACATACAT |
| PDS-IV15+ | CCAAAGGTTGGATTTGATGCC |
| PDS-IV15- | GAATAGCTCAGTTGTTCTTTGATACG |
| PDS-EXON5+ | CCGACGAACACTTTCTCGTATC |
| PDS-EXON5- | GGGTTCCAGGAAATTACTTTGTTT |
| PDS-EXON7 + 8+ | AAGTCTCCCTGTTCTGTCCTA |
| PDS-EXON7 + 8- | AGGGTGTTGCAGACAAAGT |
| PDS-EXON10+ | TTCACTGCTGGATTGCTCAC |
| PDS-EXON10- | CCCCTTGGGATGGATTTAAC |
| PDS-EXON17+ | GGAGGAACTTGATATCCCAACC |
| PDS-EXON17- | ATACTGGACAACCCACATCATT |
| PDS-EXON19+ | GAGCAATGCGGGTTCTTTG |
| PDS-EXON19- | GCTAGACTAGACTTGTGTAATGTTTG |
| HBB+ | GGTTGGCCAATCTACTCCCA |
| HBB- | AAGGTGCCCTTGAGGTTGTC |
| HBB3+ | TCATGCCTCTTTGCACCATT |
| HBB3- | AATCCAGCCTTATCCCAACCA |
| MMACHC+ | GGAGTCGAAGCTGACTCA |
| MMACHC- | CAGTTGCAACGAAGCCAATC |
| HBA2+ | CTTCTCTGCACAGCTCCTAAG |
| HBA2- | GCTGCCCACTCAGACTTTAT |
| GJB2+ | GACGCCAAGTTTGAAGGAAC |

TABLE 11-continued

Corresponding primers to the second batch of pathogenic sites

| Name of pathogenic site | Primer sequences |
| --- | --- |
| GJB2− | CTACTGCTAGAAACAGCCTACTC |
| GJB2-C79+ | TCGCATTATGATCCTCGTTG |
| GJB2-C79− | GGACACAAAGCAGTCCACAG |

3 samples amplified according to Example 2 (shown as 2_1, 2_3 and 2_7 in FIG. 4) and three samples amplified according to Example 3 (shown as 3_1, 3_4 and 3_8 in FIG. 4) were randomly selected as template DNA, respectively, and the 20 pathogenic sites above were respectively amplified by PCR using dye-containing 2×Taq MasterMix (purchased from Beijing ComWin Biotech Co., Ltd., Cat. No. CW0682). Amplification system and amplification program are shown in Table 8 and Table 9, respectively, except that the annealing temperature was both selected as 55° C.

Figure 4:
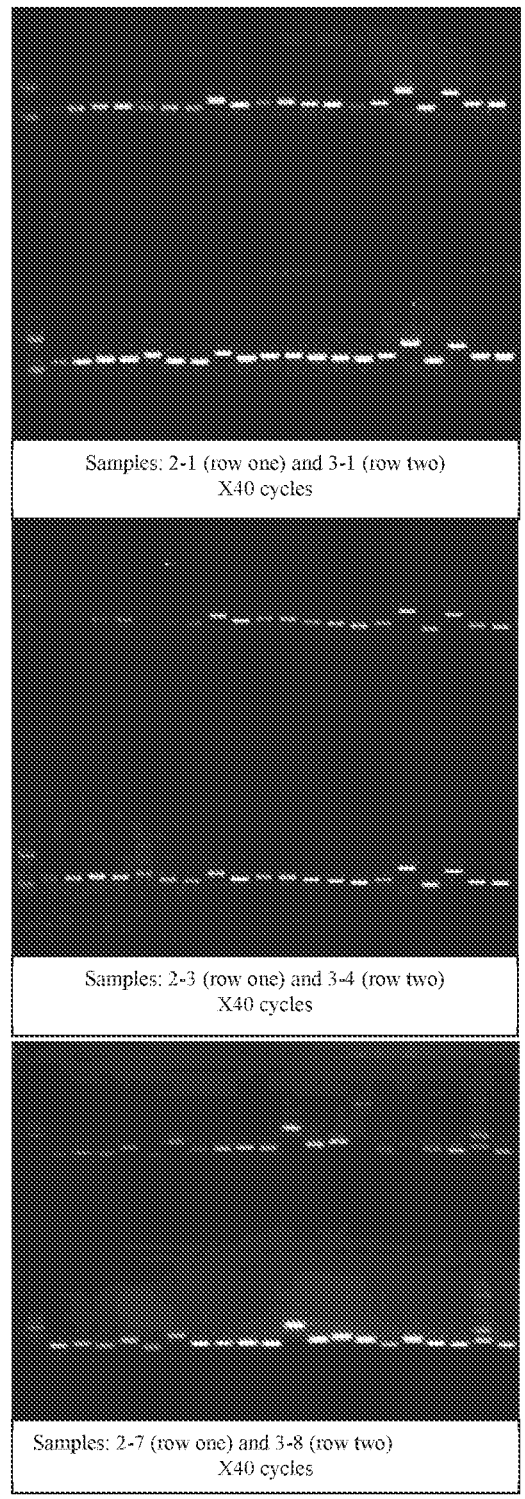
FIG. 4 shows gel electrophoresis results of the following: genomic DNA of normal human epidermal fibroblasts (AFP) was amplified using the three-step method of Example 2 and the two-step method of Example 3, respectively, and 3 samples were randomly selected from the amplification products obtained from the two methods (i.e., a total of 6 samples) as templates, respectively, and the 20 pathogenic sites shown in Table 10 were amplified using primers shown in Table 11, and the amplification products were subject to gel electrophoresis. a-c therein represent gel electrophoresis images of re-amplified products of the single-cell genomic DNA amplification products, respectively, wherein the upper-row bands indicate results of amplification using the two-step method and the lower-row bands indicate results of amplification using the three-step method (a: Upper-row corresponds to sample 2_1 and lower-row corresponds to sample 3_1; b: Upper-row corresponds to sample 2_2 and lower-row corresponds to sample 3_4; c: Upper-row corresponds to sample 2_7 and lower-row corresponds to sample 3_8). In each electrophoresis image, from left to right, lanes sequentially indicate molecular-weight marker, and results of amplification of pathogenic sites 1-20 shown in Table 6.

Amplification results are shown in FIG. 4. The amplification results show that: the 20 disease-causing sites can all be well amplified in the amplification products of the two amplification methods above, and there was no significant difference in amplification accuracy and amount of amplification products between the two methods.

q-PCR Detection Using Quality Detection Primers 4 samples amplified according to the three-step method of Example 2 (shown as 3-5, 3-6, 3-9, 3-10 in FIG. 5) and 4 samples amplified according to the two-step method of Example 3 (shown as 2-1, 2-3, 2-7, 2-10 in FIG. 5) were randomly selected as template DNA, respectively. The template DNA was subject to q-PCR detection using 6 pairs of quality inspection primers as shown in Table 14, which target DNA sequences on different chromosomes, respectively. 2×FastSYBR Mixture (purchased from Beijing ComWin Biotech Co., Ltd., Cat. No. CW0955) was used in fluorescent quantitative PCR. Composition of amplification system is shown in Table 12, and amplification program is shown in Table 13.

TABLE 12 q-PCR amplification system

| | |
| --- | --- |
| 2 × FastSYBR Mixture | 25 μl |
| Forward primer, 10 μM | 2 μl |
| Reverse primer, 10 μM | 2 μl |
| Template DNA | 40 ng |
| RNase-free water | Added to a final volume of 50 μl |

TABLE 13 q-PCR amplification program

| Cycle number | Temperature (centigrade) | Step | Time |
| --- | --- | --- | --- |
| 1 | 95 | Pre-denaturation | 1 min |
| 40 | 95 | Denaturation | 15 s |
| | 58 | Anneal/extension | 40 s |

TABLE 14

Quality inspection primer pairs

| Name of primer | Primer sequence | Chromosomal location |
| --- | --- | --- |
| CH1+ | AGGAAAGGCATACTGGAGGGACAT | chr1 |
| CH1− | TTAGGGATGGCACCACACTCTTGA | |
| CH2+ | TCCCAGAGAAGCATCCTCCATGTT | chr2 |
| CH2− | CACCACACTGCCTCAAATGTTGCT | |
| CH4+ | ATGGGCAAATCCAGAAGAGTCCAG | chr4 |
| CH4− | CCATTCACTTCCTTGGAAAGGTAGCC | |
| CH5+ | AATAGCGTGCAGTTCTGGGTAGCA | chr5 |
| CH5− | TTCACATCCTGGGAGGAACAGCAT | |
| CH6+ | TGAATGCCAGGGTGAGACCTTTGA | chr6 |
| CH6− | TGTTCATTATCCCACGCCAGGACT | |
| CH7+ | ACCAAAGGAAAGCCAGCCAGTCTA | chr7 |
| CH7− | ACTCCACAGCTCCCAAGCATACAA | |

Figure 5:
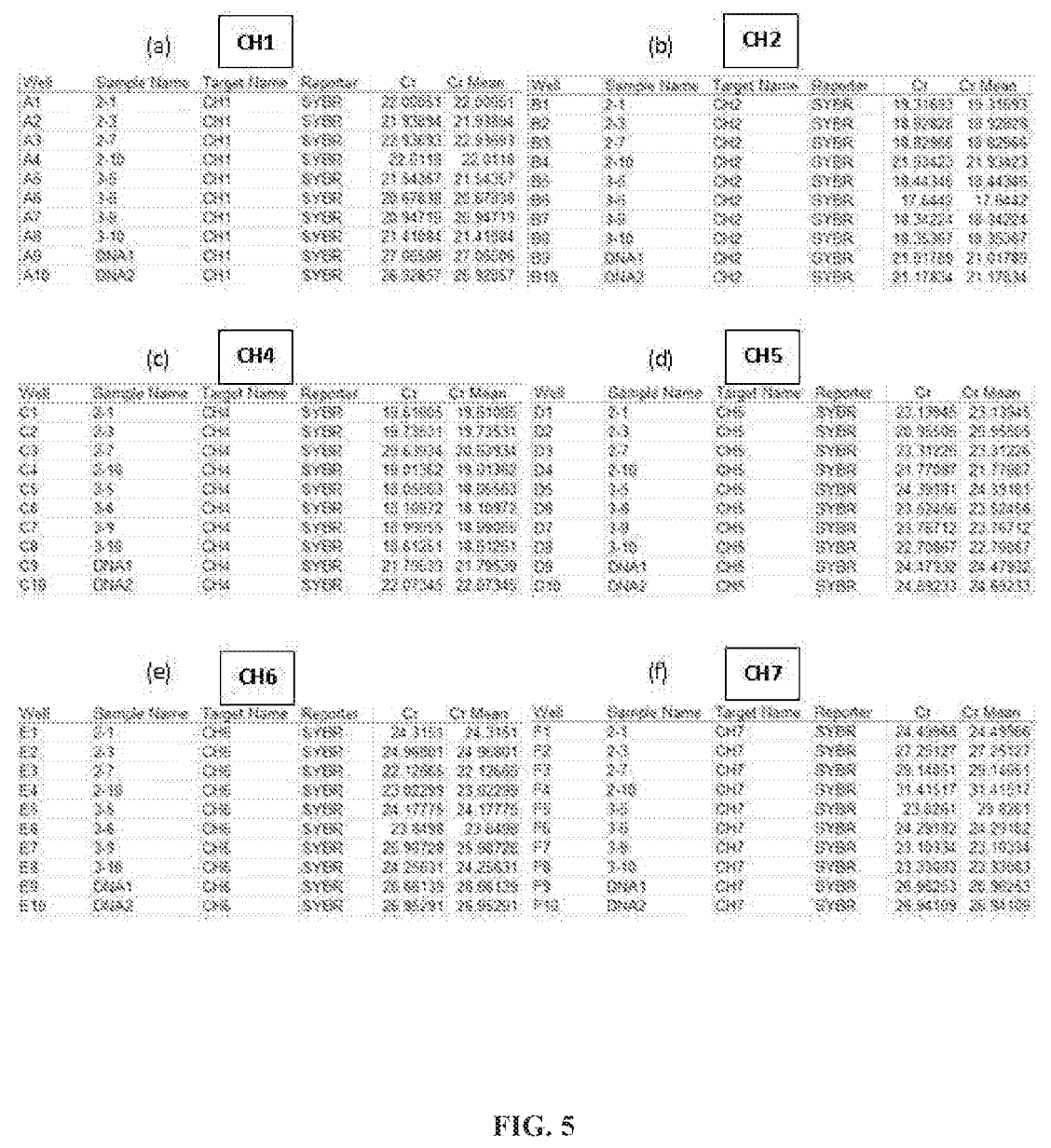

Amplification results are shown in FIG. 5, wherein a-f refer to data of q-PCR detection for template DNA, targeting DNA sequences on chromosomes CH1, CH2, CH3, CH4, CH5, CH6 and CH7, respectively. Amplification results show that: Cr values obtained from q-PCR using amplification products of the two-step method and those of the three-step method as q-PCR templates, were comparable, with no significant difference, indicating that there was no significant difference in the initial number of templates for q-PCR, i.e., there was no significant difference between the amount of amplification products of the two-step method and the three-step method. Moreover, the 6 pairs of quality inspection primers verified different sequences on chromosomes 1, 2, 4, 5, 6 and 7, respectively, and results consistently showed no significant difference between initial amounts of template of the two methods.

Figure 6:
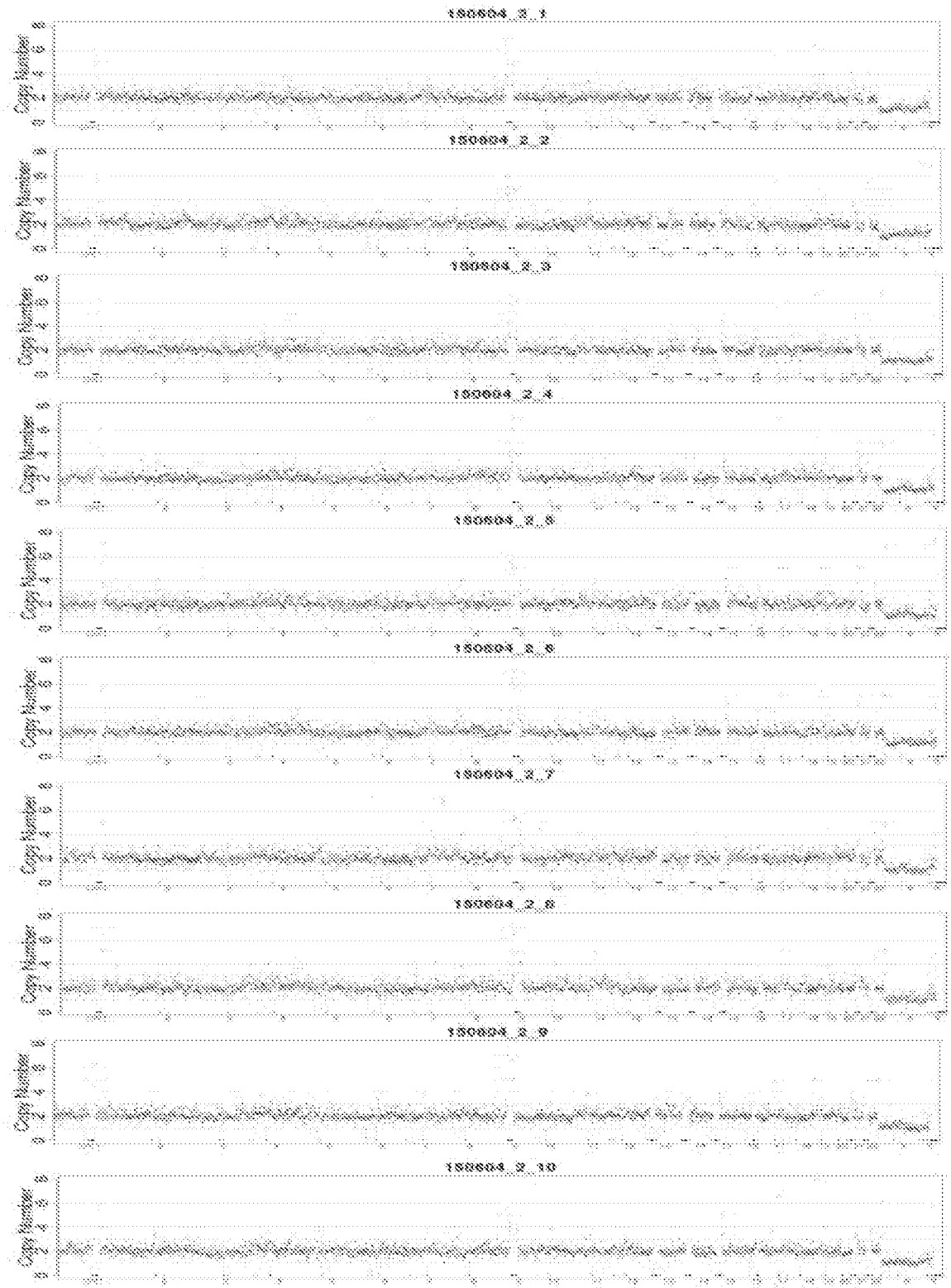
FIG. 6 shows results of chromosome copy number obtained by sequencing the genomic library constructed using the amplification products obtained by amplifying genomic DNA of normal human epidermal fibroblasts (AFP) using the two-step method of Example 3. The vertical ordinate represents chromosome copy number, which is 2 in normal persons; the horizontal ordinate represents chromosomes 1-22 and sex chromosomes, wherein a-j represent results of chromosome copy number obtained by sequencing genomic libraries constructed with samples 2_1, 2_2, 2_3, 2_4, 2_5, 2_6, 2_7, 2_8, 2_9, and 2_10.
Figure 7:
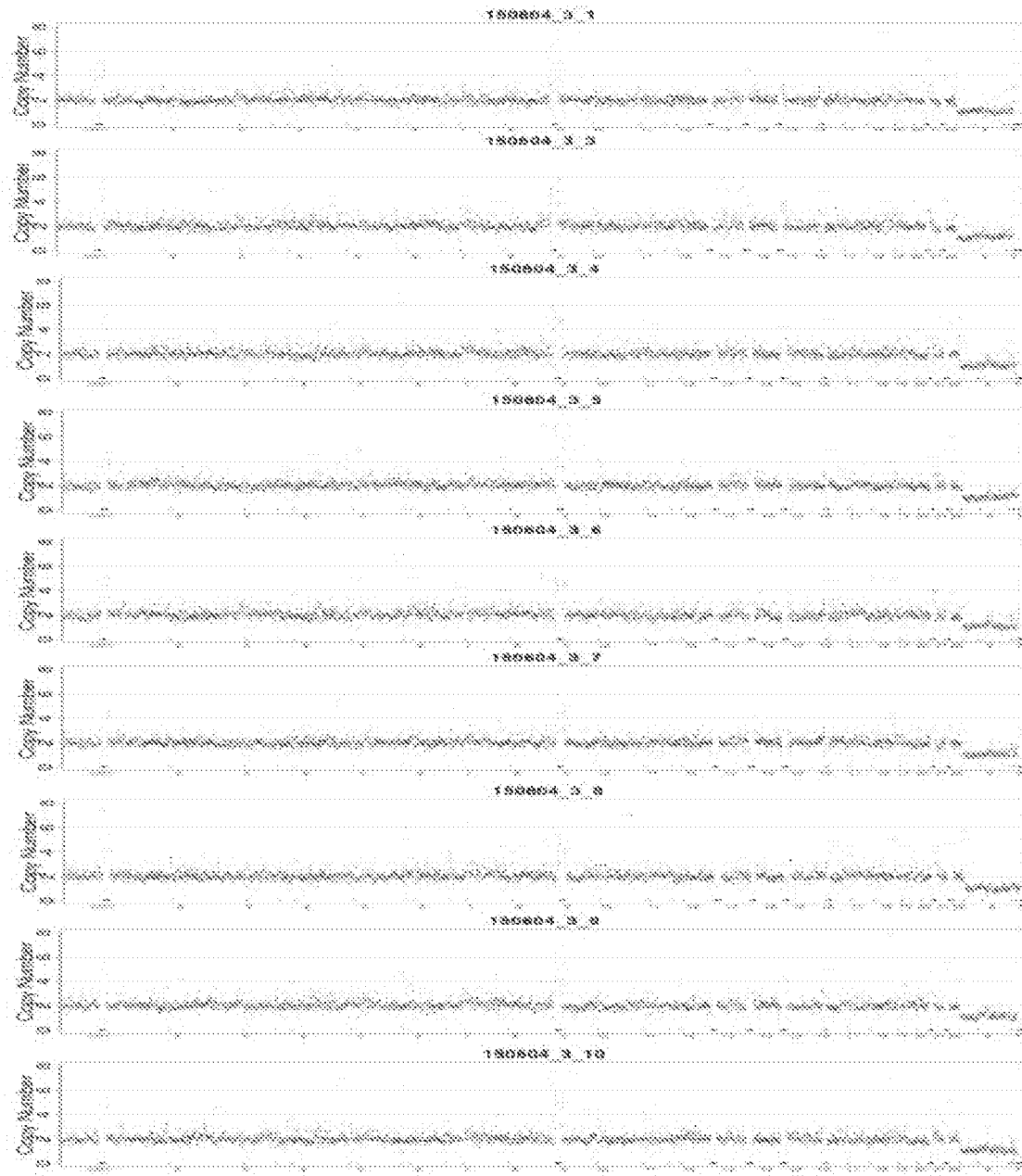
FIG. 7 shows results of chromosome copy number obtained by sequencing the genomic library constructed using the amplification products obtained by amplifying genomic DNA of normal human epidermal fibroblasts (AFP) using the three-step method of Example 2. The vertical ordinate represents chromosome copy number, which is 2 in normal persons; the horizontal ordinate represents chromosomes 1-22 and sex chromosomes. a-i represent results of chromosome copy number obtained by sequencing genomic libraries constructed from samples 3_1, 3_3, 3_4, 3_5, 3_6, 3_7, 3_8, 3_9 and 3_10.
Figure 8:
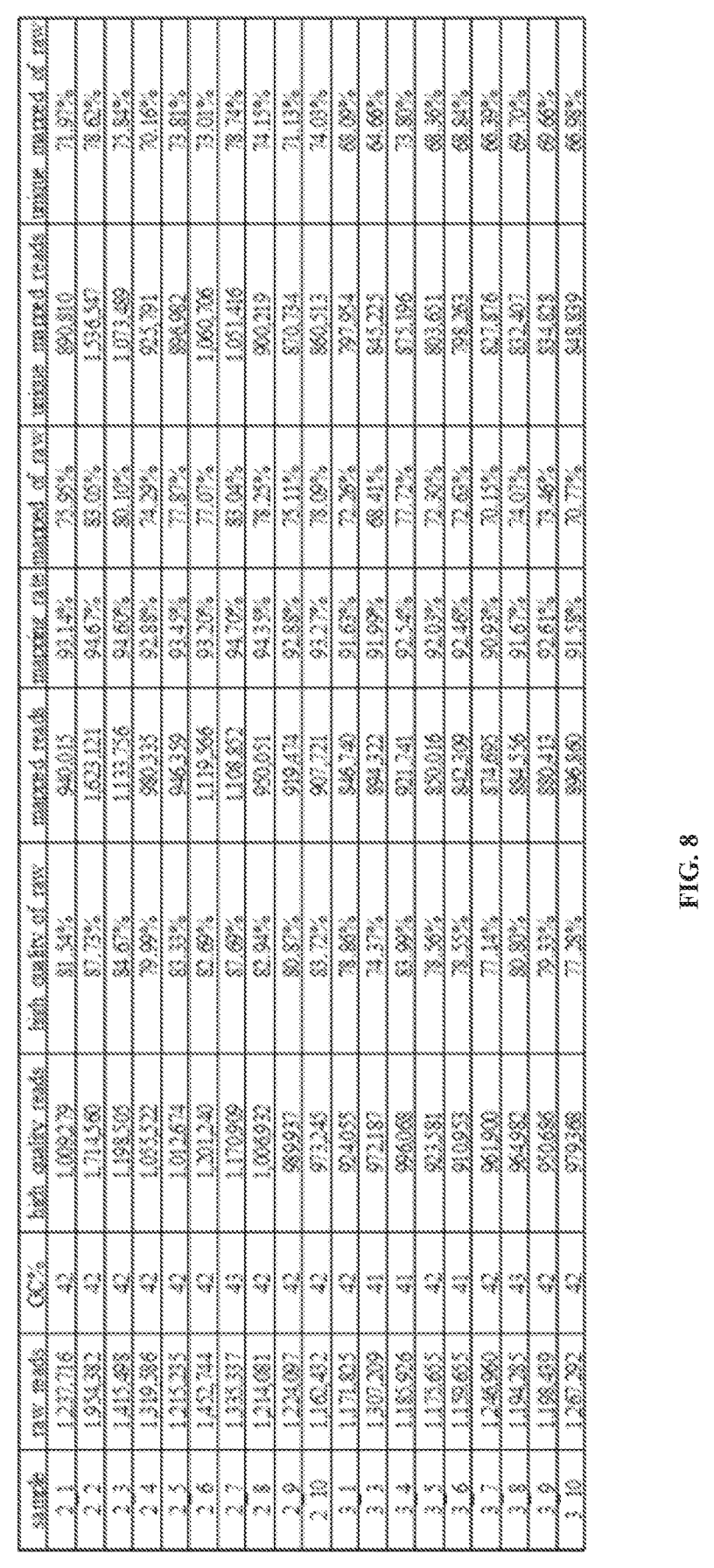
Figure 9:
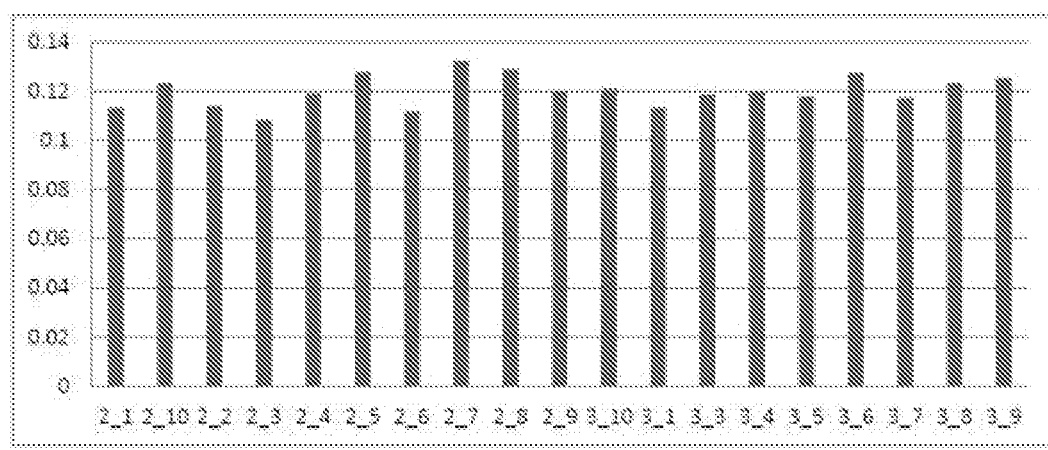
FIG. 9 shows comparison results of copy number variation coefficient after second-generation sequencing of genomic libraries constructed respectively using the amplification products obtained by amplifying genomic DNA of normal human epidermal fibroblasts (AFP) using the three-step method of Example 2 (i.e. samples 3_1, 3_3, 3_4, 3_5, 3_6, 3_7, 3_8, 3_9 and 3_10) and using the two-step method of Example 3 (i.e. samples 2_1, 2_2, 2_3, 2_4, 2_5, 2_6, 2_7, 2_8, 2_9 and 2_10), respectively.

Gene Sequencing 10 purified products amplified by the two-step method of Example 3 (shown as 2-1, 2-2, 2-3, 2-4, 2-5, 2-6, 2-7, 2-8, 2-9, 2-10 in FIG. 6, FIG. 8 and FIG. 9) and 10 purified samples amplified by the three-step method of Example 2 (shown as 3-1, 3-2, 3-3, 3-4, 3-5, 3-6, 3-7, 3-8, 3-9, 3-10 in FIG. 7, FIG. 8 and FIG. 9) were randomly selected, constructed into genomic library through fragmentation, and sequenced with hiseq2500 sequencer by means of shallow sequencing. For each sample, a data volume of 1.5 Mb was measured, and the sequence obtained by sequencing was mapped to human reference genome (hg19).

Results of the two-step method in Example 3 is shown in FIG. 6, and results of the three-step method in Example 2 is shown in FIG. 7, wherein the vertical ordinate represents chromosome copy number, which is 2 in normal persons; the horizontal ordinate represents chromosomes 1-22 and sex chromosomes. The results above show that: chromosomal detection of cells by the three-step method of Example 2 and by the two-step method of Example 3 have consistent results.

In sequencing results, various indicator parameters of high-throughput sequencing results are also provided, as shown in FIG. 8, wherein the "unique reads ratio mapped to human genome" in raw data (i.e., unique_mapped_of_raw) is the most important measuring indicator. The average unique_mapped_of_raw of all samples of the two-step method in Example 3 was 74.15%, while that of all samples of the three-step method in Example 2 was 68.5%, indicating that the ratio of unique_mapped_of_raw for amplification sample of the two-step method of Example 3 was significantly higher than that for amplification sample of the MALBAC three-step method.

The copy-number variation coefficient can be used to compare the dispersion degree of sample copy-number after the sample is amplified by the two types of amplification methods. The average copy-number variation coefficient of all amplified samples using the two-step method of Example 3 was 0.1200, while that of all amplified samples using the three-step method of Example 2 was 0.1205. There was no significant difference between the copy-number variation coefficients of the two types of amplification methods. See FIG. 9 for detailed data.

ADO Evaluation

150 SNP sites were randomly selected and corresponding primers were designed. See Table 15 for selected sites and corresponding primers.

TABLE 15

150 SNP sites and the corresponding primers thereof

| Primer name | Primer | Chromosomal location | Site of amplification |
|---|---|---|---|
| HBB-SNP1-F | TGGGCTGCAGAAAGAAATAGA | chr11 | rs7102381 |
| HBB-SNP1-R | TCCCAAAGTGCTGGGATTAC | chr11 | |
| HBB-SNP2-F | GTGCATAAAACTTTAGAGTACAGCTCA | chr11 | rs10836574 |
| HBB-SNP2-R | TGGTTACTATTCGAGAGGACACTG | chr11 | |
| HBB-SNP3-F | TGACAGTCAAGGCAGTAGCAA | chr11 | rs16907084 |
| HBB-SNP3-R | TAACCCTTGTTGGTGAGCAG | chr11 | |
| HBB-SNP4-F | CTGGTCCTTGACTTCCTCTCA | chr11 | rs919900 |
| HBB-SNP4-R | TGGCTAAGAAGACCTGGTTGA | chr11 | |
| HBB-SNP5-F | TCCTGCACAGAGTCCGTAGA | chr11 | rs17339000 |
| HBB-SNP5-R | GGGGTTCTTCTGACTTCCAA | chr11 | |
| HBB-SNP6-F | CACAGAAGTGTTGTAGGGTAGAGG | chr11 | rs10082629 |
| HBB-SNP6-R | AGCAGGCAGGCATTGTTTAT | chr11 | |
| HBB-SNP7-F | GGAGTGCCTTTGCATCATCT | chr11 | rs2124447 |
| HBB-SNP7-R | GCGGTGTTTGGTTTTCTGTT | chr11 | |
| HBB-SNP8-F | TCTTGGTAGAAATGGATAACCTG | chr11 | rs2500035 |
| HBB-SNP8-R | AGCAACAGGGTTCAAGAAGG | chr11 | |
| HBB-SNP9-F | AGCTCTTCAGGTGGCAGGTA | chr11 | rs1378749 |
| HBB-SNP9-R | CCTTGAAGCAGCCTTGTGAT | chr11 | |
| HBB-SNP10-F | CCTCCTGAATTAATCGGCATT | chr11 | rs2500014 |
| HBB-SNP10-R | CACATTAAAAATTGAAGGATTCTATGA | chr11 | |
| HBB-SNP11-F | TCCCCATGAACTTTTTGCTT | chr11 | rs4144715 |
| HBB-SNP11-R | TGTCCAGAATGGTGTTGCTC | chr11 | |
| HBB-SNP12-F | CGTGTTGCTTAACGATGAGG | chr11 | rs2445296 |
| HBB-SNP12-R | TGTACAGGTTTGTAGCCAAGGA | chr11 | |
| HBB-SNP13-F | TGCTCATCCCCCAGTAAAAC | chr11 | rs4910715 |
| HBB-SNP13-R | GGAAATCCCTCATTTCATGC | chr11 | |
| HBB-SNP14-F | TCCAAGCATGATGAGGGATT | chr11 | rs4910721 |
| HBB-SNP14-R | TTTTTATGCATGCTGGCTTTT | chr11 | |
| HBB-SNP15-F | GGGATTATTTGAGGCAATCAG | chr11 | rs10837582 |
| HBB-SNP15-R | AACAATAACCAATAAACACGGACA | chr11 | |
| HBB-SNP16-F | CCCCTAGGCACATGAAACAC | chr11 | rs3888708 |
| HBB-SNP16-R | TTTGGGTGTGGGGATAACTC | chr11 | |
| HBB-SNP17-F | AGTGCAGTTGTGTGGCATGT | chr11 | rs2723381 |
| HBB-SNP17-R | GGGGTCCTGACTTGATGTGT | chr11 | |
| HBB-SNP18-F | CAGCATGACTGGCATTTGAT | chr11 | rs5017236 |
| HBB-SNP18-R | TCACCACACTATTTTCCATTGTG | chr11 | |
| HBB-SNP19-F | TGCATCCTGTGAGAAAGCAG | chr11 | rs12360876 |
| HBB-SNP19-R | AAAAAGAAAAGCCATCGTAAGC | chr11 | |
| HBB-SNP20-F | GCAATTTCCTGGCCATATTC | chr11 | rs2736532 |
| HBB-SNP20-R | GACATTTGACTTGAGCCACTGA | chr11 | |
| HBB-SNP21-F | TGCCCCCAAAAGTCTCATTA | chr11 | rs2647579 |
| HBB-SNP21-R | TTGAGGCATGTGCTCATTTT | chr11 | |

TABLE 15-continued

150 SNP sites and the corresponding primers thereof

| Primer name | Primer | Chromosomal location | Site of amplification |
|---|---|---|---|
| HBB-SNP22-F | GCACATAAAAGGCCAGCACT | chr11 | rs11037444 |
| HBB-SNP22-R | TGGGCTCTTGGTGATCATTT | chr11 | |
| HBB-SNP23-F | AGTCCTAGCCAGAGCGTCAA | chr11 | rs1118715 |
| HBB-SNP23-R | TTTCGCTGAAATTGTTTATCAGA | chr11 | |
| HBB-SNP24-F | TGGGTTGGTGACATCACTGT | chr11 | rs365943 |
| HBB-SNP24-R | CTCCAAGGATTCCCTTCCAT | chr11 | |
| HBB-SNP25-F | TACAGTGGAGATGGCAGCAG | chr11 | rs4910812 |
| HBB-SNP25-R | AGGGCCAGAGTAGGGTGAAT | chr11 | |
| HBB-SNP26-F | CTTTGCAGAACCACTGGATG | chr11 | rs10742709 |
| HBB-SNP26-R | GAGGGCTCTTCTGCACTGAG | chr11 | |
| HBB-SNP27-F | GCATGCCATAGGACATTTGA | chr11 | rs2341428 |
| HBB-SNP27-R | TTTCATCTTGAAGGAACACACAA | chr11 | |
| HBB-SNP28-F | CCAGAAGGAGTTGGGAGATG | chr11 | rs12272467 |
| HBB-SNP28-R | CGCTCACTCGGCTTTTATCT | chr11 | |
| HBB-SNP29-F | GCCACCACAGTTGGCTTTAT | chr11 | rs10838441 |
| HBB-SNP29-R | TCATTTTTGCCCTCTCCATC | chr11 | |
| HBB-SNP30-F | TGACTCTCTCCATGGCTGTG | chr11 | rs3740998 |
| HBB-SNP30-R | AAGAGCTTGGTGGGCATAGA | chr11 | |
| HBB-SNP31-F | ACATGACCTCACCAAATGAACT | chr11 | rs2709135 |
| HBB-SNP31-R | ACTGCATTCTTCAGTAGGCTAATC | chr11 | |
| HBB-SNP32-F | CTGCTGTCCCTGTGTCTTC | chr11 | rs2657175 |
| HBB-SNP32-R | CTGGAAGTTCCCAGCTTCTC | chr11 | |
| HBB-SNP33-F | GTCCTCTGGATTGTCTCATTGG | chr11 | rs2641405 |
| HBB-SNP33-R | CATGGCTGTCGAACAGATGA | chr11 | |
| HBB-SNP34-F | GGACGCTGTACCCTTGTAAA | chr11 | rs4910630 |
| HBB-SNP34-R | CCATCCTCTCCAAACTGTCC | chr11 | |
| HBB-SNP35-F | TTTCATGCCTTCGAGAGTGG | chr11 | rs1009240 |
| HBB-SNP35-R | CACTGGCAACAGATCCTTGA | chr11 | |
| HBB-SNP36-F | CACGAGCTGATCCTTCAACA | chr11 | rs4910511 |
| HBB-SNP36-R | CAGGTGAGACTTCTTGCCTATT | chr11 | |
| HBB-SNP37-F | ATATGGGCATGGAACTTGGT | chr11 | rs4910512 |
| HBB-SNP37-R | TCCTATGTCTAGCTGGTTAATTCAT | chr11 | |
| HBB-SNP38-F | AAATTGCTGTGGAAACTGAGTG | chr11 | rs11600417 |
| HBB-SNP38-R | GGGTCTGGTCCTCAACAATTA | chr11 | |
| HBB-SNP39-F | GGTGGTGATTGGTGATGAAGA | chr11 | rs4625457 |
| HBB-SNP39-R | CTGCCTCCAAACCTAGTCTATTC | chr11 | |
| HBB-SNP40-F | CTTCCGAATTATGAACCTGGATTAC | chr11 | rs4291666 |
| HBB-SNP40-R | TGTTCCTCGGCTCTCTCTAA | chr11 | |
| HBB-SNP41-F | AATGTGGGAAACGCAGGT | chr11 | rs10768157 |
| HBB-SNP41-R | GTTCTGTTTCCACCCTGATGTA | chr11 | |
| HBB-SNP42-F | TCTAGGACCACCTCAGTGAAT | chr11 | rs10836452 |
| HBB-SNP42-R | GAAGAAGGAATGCCAACAGAAAG | chr11 | |
| HBB-SNP43-F | ACAGATAAATGCTACTAGTTGTAGAGTG | chr11 | rs7108524 |
| HBB-SNP43-R | CATCCTTATAAACTCACATTTACCCATC | chr11 | |
| HBB-SNP44-F | CTCATGCACAGACACATGGA | chr11 | rs4436535 |
| HBB-SNP44-R | TGTGCACTGGTGACAAACT | chr11 | |
| HBB-SNP45-F | CGTGGGTCTCGATATTCTTCAC | chr11 | rs34438514 |
| HBB-SNP45-R | GGTACCAGGAGCTGATGAAAG | chr11 | |
| HBB-SNP46-F | GGATGTCTGTCCACTCTGAAA | chr11 | rs16933888 |
| HBB-SNP46-R | GGACATTGTGTGCTGATGATG | chr11 | |

TABLE 15-continued

150 SNP sites and the corresponding primers thereof

| Primer name | Primer | Chromosomal location | Site of amplification |
|---|---|---|---|
| HBB-SNP47-F | TTGGGTGACAGAGACAAACC | chr11 | rs1976339 |
| HBB-SNP47-R | ACAAACTGAATTATGTGGGAATCAG | chr11 | |
| HBB-SNP48-F | TTGGTGAATGTGCTCCCTAC | chr11 | rs10769175 |
| HBB-SNP48-R | GGGTTAGATGGGTAGAGATTTGG | chr11 | |
| HBB-SNP49-F | ATCCAGATCGAGAGACAGAAGA | chr11 | rs2291842 |
| HBB-SNP49-R | GTCTTACCTGCAGCATCTCTAC | chr11 | |
| HBB-SNP50-F | TGAAGGAGTCAATAAGCTGTTAGAG | chr11 | rs4910841 |
| HBB-SNP50-R | ACTCCTGCAGATCAGCATTTC | chr11 | |
| HBB-SNP51-F | CCAAAGCCATGTGATCCTACA | chr11 | rs7944807 |
| HBB-SNP51-R | ATGACACAGACATGGGAACC | chr11 | |
| HBB-SNP52-F | CACTTTATCTTGCTGACTACAGAA | chr11 | rs2133266 |
| HBB-SNP52-R | CATAAAGGAATTTATAGGCTGATAGCTG | chr11 | |
| HBB-SNP53-F | AACTGCTTATTTCTGCTTCAGT | chr11 | rs7950248 |
| HBB-SNP53-R | CTGTATTGTGTCTAACTGCCCAA | chr11 | |
| HBB-SNP54-F | CAGGGCAACTATCAAACCATAGA | chr11 | rs7948009 |
| HBB-SNP54-R | GTTATGCCACCATCCTCACTAA | chr11 | |
| HBB-SNP55-F | TCAGTTACAGTCATAGGACCATTC | chr11 | rs10047437 |
| HBB-SNP55-R | AGCTGTTGGCTCCATTCAT | chr11 | |
| HBB-SNP56-F | CCTATGCCTATGATGTCAGGTAAT | chr11 | rs7112569 |
| HBB-SNP56-R | CTGGTAGTAATACACTCTCTTAGCTTT | chr11 | |
| HBB-SNP57-F | GAGTAGTTGTGACACAGGCAT | chr11 | rs10838688 |
| HBB-SNP57-R | AAACTTGTTGGCTGACATTGATAG | chr11 | |
| HBB-SNP58-F | TGTGGCAGTATTCACAGATTCTC | chr11 | rs1901845 |
| HBB-SNP58-R | TCCAAGCCAAGAGCCAAATAA | chr11 | |
| HBB-SNP59-F | GACCATTTCTTAAAGCCACACAA | chr11 | rs1013377 |
| HBB-SNP59-R | AGCCCAGATTTCACCATGTAATA | chr11 | |
| HBB-SNP60-F | ATTATGTCATGCCCTGTGCT | chr11 | rs10838750 |
| HBB-SNP60-R | CTACACTGACCCAACCATCTG | chr11 | |
| SLC26A4-SNP1-F | GTGTGGAATAGAAGGACAAGTGA | chr7 | rs7786720 |
| SLC26A4-SNP1-R | GCCACCATGCTCAGACAA | chr7 | |
| SLC26A4-SNP2-F | GGATATGTTCCTTAATCTATGTCAAACAGG | chr7 | rs6946733 |
| SLC26A4-SNP2-R | GCAGTCCTGGGCCAATTTATG | chr7 | |
| SLC26A4-SNP3-F | ACTGATTAGATTGGATGAGTTCCA | chr7 | rs2536505 |
| SLC26A4-SNP3-R | TAAGACAGAGAGGCCTGGT | chr7 | |
| SLC26A4-SNP4-F | CATTTCTCTCTTACTGCTTTGACA | chr7 | rs717099 |
| SLC26A4-SNP4-R | GAAACAGAGAGAGAAGCAAAGAAA | chr7 | |
| SLC26A4-SNP5-F | GGTGACGATGGTGACAACTTT | chr7 | rs2302453 |
| SLC26A4-SNP5-R | TGTGGTTTCACTGCATGTACTC | chr7 | |
| SLC26A4-SNP6-F | CGAAGCTTGAAAGACTTGGTAATG | chr7 | rs4730221 |
| SLC26A4-SNP6-R | CCACCTCTTCCCTAACTGAAAG | chr7 | |

TABLE 15-continued

150 SNP sites and the corresponding primers thereof

| Primer name | Primer | Chromosomal location | Site of amplification |
|---|---|---|---|
| SLC26A4-SNP7-F | TACACACAGCAGGACAACTG | chr7 | rs2158347 |
| SLC26A4-SNP7-R | CTGGGCTAACACAGGGATTT | chr7 | |
| SLC26A4-SNP8-F | AAATTGCAGTGCTTAGTGGAAA | chr7 | rs7794437 |
| SLC26A4-SNP8-R | AGCTAGGAGTTTAGCAACTGTG | chr7 | |
| SLC26A4-SNP9-F | AGGAAGCCTCGTAACATGAC | chr7 | rs6966616 |
| SLC26A4-SNP9-R | CTGATTGTCTCCACTATCTTTAGAATG | chr7 | |
| SLC26A4-SNP10-F | AGCCCTAAGAGATTTCTCACATT | chr7 | rs10260250 |
| SLC26A4-SNP10-R | TTTCCTATCACCAGTGGATTGAG | chr7 | |
| SLC26A4-SNP11-F | CATTGGACTAAGGTGCCAGATAG | chr7 | rs2107763 |
| SLC26A4-SNP11-R | TTGTGCTTGGGCAGAGATAC | chr7 | |
| SLC26A4-SNP12-F | CCACAGTCAGAAGAGTCCTTAC | chr7 | rs6979121 |
| SLC26A4-SNP12-R | CACAGTTCAACCCATAACACATAG | chr7 | |
| SLC26A4-SNP13-F | CTGGACAACGAGAACACCTT | chr7 | rs10276321 |
| SLC26A4-SNP13-R | CCTTAAAGGTCCTTATCACACCA | chr7 | |
| SLC26A4-SNP14-F | TTCTAGAAGACATCTACATACCTTGG | chr7 | rs2520279 |
| SLC26A4-SNP14-R | GGTCTTGGCAGGTACGTTTA | chr7 | |
| SLC26A4-SNP15-F | GGACTGGTCAAGACTGAACTAC | chr7 | rs2520257 |
| SLC26A4-SNP15-R | CCAATGTGCTGTTGGCTTTAC | chr7 | |
| SLC26A4-SNP16-F | GGGTAAATACAGACCACAGATG | chr7 | rs13224313 |
| SLC26A4-SNP16-R | GGAAATCCAGGTTCAGAATAGT | chr7 | |
| SLC26A4-SNP17-F | GTGGTTCTTTATTGTAGCCCATTT | chr7 | rs2269778 |
| SLC26A4-SNP17-R | TCTTCCTTGAGGGCAAGATTC | chr7 | |
| SLC26A4-SNP18-F | AGAATGTGGACAGGTCATTAGC | chr7 | rs989960 |
| SLC26A4-SNP18-R | CTAAGCTATCTATGGTTGTTATGAGGA | chr7 | |
| SLC26A4-SNP19-F | TCCCTGAGGTCAAGACTATGT | chr7 | rs2108227 |
| SLC26A4-SNP19-R | TCTATGCTCCTGCTTCTCTCT | chr7 | |
| SLC26A4-SNP20-F | CTTTCTGAAGTGTGAATTACCACAA | chr7 | rs10272963 |
| SLC26A4-SNP20-R | AAGAAATGTGGGCAGCTTCTA | chr7 | |
| SLC26A4-SNP21-F | GAGGCACAGATATAAGCCACATA | chr7 | rs7811034 |
| SLC26A4-SNP21-R | CCAGTAACAACCCTGCTTCA | chr7 | |

TABLE 15-continued

150 SNP sites and the corresponding primers thereof

| Primer name | Primer | Chromosomal location | Site of amplification |
|---|---|---|---|
| SLC26A4-SNP22-F | GACAAGATGATGGAGCAGAAGAG | chr7 | rs17412104 |
| SLC26A4-SNP22-R | TGTCAGGGAAATCTATTTCAGGTTAG | chr7 | |
| SLC26A4-SNP23-F | GGTAAAGGAAGCTCTGGAAGAA | chr7 | rs1131398 |
| SLC26A4-SNP23-R | CATCCATGCTAACGGAGTAGTT | chr7 | |
| SLC26A4-SNP24-F | CTGCCACTTAGAAGTAGGAATGA | chr7 | rs2072208 |
| SLC26A4-SNP24-R | GTGGCTGATCTGTGAGGATAAA | chr7 | |
| SLC26A4-SNP25-F | TTCCTCCTCTCTGGAGGTTT | chr7 | rs1544474 |
| SLC26A4-SNP25-R | CATTGAGCAAGCTTCATGTACTC | chr7 | |
| SLC26A4-SNP26-F | TGGAGGGCAGTCTGAAATATG | chr7 | rs12670994 |
| SLC26A4-SNP26-R | GTAAGTAACTGTTTGGTACTCTGTTG | chr7 | |
| SLC26A4-SNP27-F | AAACATCCCTCTGCAATCCATC | chr7 | rs1990158 |
| SLC26A4-SNP27-R | TATCCTTGAAATCCATATTAGCAGAAGC | chr7 | |
| SLC26A4-SNP28-F | CCCAATCTGACAGCACAATTTC | chr7 | rs390547 |
| SLC26A4-SNP28-R | CCAAGTTACTTAGCCTGGAGTT | chr7 | |
| SLC26A4-SNP29-F | ACCAGGACAGACACAGATTATT | chr7 | rs401487 |
| SLC26A4-SNP29-R | CAAGACCATCTCAGATCCCTAC | chr7 | |
| SLC26A4-SNP30-F | GGGATGGAAGGGTAAATAAGACA | chr7 | rs760355 |
| SLC26A4-SNP30-R | GCTGCTAGAGTCTCAGTATCAC | chr7 | |
| SLC26A4-SNP31-F | GGAAAGCCTGGAGTGTGAG | chr7 | rs17153388 |
| SLC26A4-SNP31-R | ATACAACAGAGTGCTGGACTTAG | chr7 | |
| SLC26A4-SNP32-F | AAGTTGGAGGATTCACGCTTC | chr7 | rs2107910 |
| SLC26A4-SNP32-R | TCAGATTGTGTCAGCACCATTTA | chr7 | |
| SLC26A4-SNP33-F | GTTTGCTTGGCTGCAGTAAT | chr7 | rs17153394 |
| SLC26A4-SNP33-R | AAGTCCCAAAGGAAGGTAAGAG | chr7 | |
| SLC26A4-SNP34-F | ACTTGCTCTTGTACCCATCAC | chr7 | rs6466131 |
| SLC26A4-SNP34-R | ATGTTTCATGAACTGGGCAATC | chr7 | |
| SLC26A4-SNP35-F | GAGGGAGATCTTTATCCATCTCAAG | chr7 | rs2132462 |
| SLC26A4-SNP35-R | TGGAGACCAATAATCCACTGTTT | chr7 | |
| SLC26A4-SNP36-F | CCTTTAATCCTTTAATCTGGGCAAG | chr7 | rs10268373 |
| SLC26A4-SNP36-R | TCCTAGCCTTCACATCCAGTA | chr7 | |

TABLE 15-continued

150 SNP sites and the corresponding primers thereof

| Primer name | Primer | Chromosomal location | Site of amplification |
|---|---|---|---|
| SLC26A4-SNP37-F | ACCTTCTATTCCTGCTAGCAAAT | chr7 | rs2028009 |
| SLC26A4-SNP37-R | CACAAATGACCCAAATGACTGG | chr7 | |
| SLC26A4-SNP38-F | CTCAGCTCATCTGTAACTCCAC | chr7 | rs10274710 |
| SLC26A4-SNP38-R | TGTCCATGGTTGTCTGCATAA | chr7 | |
| SLC26A4-SNP39-F | AGCACATCTGGAAAGTGAAATG | chr7 | rs4727663 |
| SLC26A4-SNP39-R | GAGTGAGCCAAGTTGGTTAATG | chr7 | |
| SLC26A4-SNP40-F | ACCATCCTCCACTCTCATCTT | chr7 | rs849380 |
| SLC26A4-SNP40-R | CCAGGCGCCAGAAACTTTA | chr7 | |
| SLC26A4-SNP41-F | CAAACCCTCCGAGACAGTAAA | chr7 | rs1526083 |
| SLC26A4-SNP41-R | CTTCTACAATTGGTCCAGGTAGG | chr7 | |
| SLC26A4-SNP42-F | AACACATTTCCATCAGTGCTTTG | chr7 | rs12536620 |
| SLC26A4-SNP42-R | CAGACAAGTTTCAGCTTATTTCTTACTC | chr7 | |
| SLC26A4-SNP43-F | GTTACTCATTAGGTGAATGCTTGTATC | chr7 | rs11763202 |
| SLC26A4-SNP43-R | AACCTTGCACTCATCCTTCC | chr7 | |
| SLC26A4-SNP44-F | CACCACGCCCAGAATCTAT | chr7 | rs10953524 |
| SLC26A4-SNP44-R | CTTAGTCACTTAGAGCTTAAACTAAGG | chr7 | |
| SLC26A4-SNP45-F | AATGCATCAAGAAGCATGTGTT | chr7 | rs12530679 |
| SLC26A4-SNP45-R | CTTCAAATTCCCTACAAATTTCTACCAC | chr7 | |
| SLC26A4-SNP46-F | GGATGATGTCACAGAAGCTGAG | chr7 | rs2072546 |
| SLC26A4-SNP46-R | GGCACAGGAACGCTCATAAT | chr7 | |
| SLC26A4-SNP47-F | GGCTGAAACTTCGCTGAAAC | chr7 | rs1035204 |
| SLC26A4-SNP47-R | CATGCTTCAAGTACCTAAATGACTAC | chr7 | |
| SLC26A4-SNP48-F | GCTGGCTGTTCAGGTACATT | chr7 | rs10262724 |
| SLC26A4-SNP48-R | GAAACCAGTAGGAGGCTAGAGA | chr7 | |
| SLC26A4-SNP49-F | CCTCTCTTTCCTTCATCTTGGG | chr7 | rs2111201 |
| SLC26A4-SNP49-R | TTGGACAAGGCAGCCAAA | chr7 | |
| SLC26A4-SNP50-F | GTTGTGAGGGAGGAGTCA | chr7 | rs17155518 |
| SLC26A4-SNP50-R | CCCTCATTTAATACCCTAGTAACTT | chr7 | |
| SLC26A4-SNP51-F | CTGCAAGGCCTAGGCTTAAT | chr7 | rs13244715 |
| SLC26A4-SNP51-R | TTTGGCTATTCTGGGTCTCTTT | chr7 | |

TABLE 15-continued

150 SNP sites and the corresponding primers thereof

| Primer name | Primer | Chromosomal location | Site of amplification |
|---|---|---|---|
| SLC26A4-SNP52-F | GGCAACATGCATTTGGACTT | chr7 | rs7783893 |
| SLC26A4-SNP52-R | TGCTGGCATCACTGTTGT | chr7 | |
| SLC26A4-SNP53-F | ATGGAGGGCCATTTGAAGAA | chr7 | rs12333431 |
| SLC26A4-SNP53-R | CCTCCCTCTCTCTCCATAGAC | chr7 | |
| SLC26A4-SNP54-F | GCTCACCTTCCTTTCACACATA | chr7 | rs1859768 |
| SLC26A4-SNP54-R | AAAGGCAGCTAATGCAGTCT | chr7 | |
| SLC26A4-SNP55-F | TACATCACCCAACTTTGACAAGTA | chr7 | rs2300043 |
| SLC26A4-SNP55-R | TTTATTAAGCACCTTCTCAATGCC | chr7 | |
| SLC26A4-SNP56-F | GGGACACATAAGGACTTGTACG | chr7 | rs13221639 |
| SLC26A4-SNP56-R | TGTGTCTGGCTTCTTTGAGG | chr7 | |
| SLC26A4-SNP57-F | AATTAGTTGAGAGGTGCAAGGT | chr7 | rs3763462 |
| SLC26A4-SNP57-R | TCTCCTTCTACTGCCATCCT | chr7 | |
| SLC26A4-SNP58-F | ACCTGGTTGCCTATGTTGAC | chr7 | rs2396001 |
| SLC26A4-SNP58-R | TCAGTGGGAAAGGACAGTCT | chr7 | |
| SLC26A4-SNP59-F | GCCTAGCAGTGGGTGTATAAT | chr7 | rs194585 |
| SLC26A4-SNP59-R | GAGTGTTGCTTGAGTTCTGTTT | chr7 | |
| SLC26A4-SNP60-F | TCCCGAAGTGCTAGGATTAGA | chr7 | rs40856 |
| SLC26A4-SNP60-R | TGTGCGGTATGTATGTGTATGT | chr7 | |
| TNNT2-SNP1-F | CTCCTCCCACCACACAATTAC | chr1 | rs1572789 |
| TNNT2-SNP1-R | GGAAGGTGGTGGCTTGATT | chr1 | |
| TNNT2-SNP2-F | GTTGGCCTTCTCCTCAGTATAG | chr1 | rs10920088 |
| TNNT2-SNP2-R | GGCCTTGGGCATCAACTA | chr1 | |
| TNNT2-SNP3-F | CTCAATTAGGAGGCAGCTTAGA | chr1 | rs957957 |
| TNNT2-SNP3-R | GGAGGTGGCTAAGCACTATAA | chr1 | |
| TNNT2-SNP4-F | TGAACCAGAGAAGGCTGCTA | chr1 | rs6675915 |
| TNNT2-SNP4-R | GGCCTTGGAAGATGAACAGAAT | chr1 | |
| TNNT2-SNP5-F | GTGGTGAAGCCCACACTT | chr1 | rs3767500 |
| TNNT2-SNP5-R | CAGCCAAGCTTTGGGAAATC | chr1 | |
| TNNT2-SNP6-F | GGAGGGACGGAGCTTCTA | chr1 | rs2297901 |
| TNNT2-SNP6-R | AGCCTCCAGCCATATCCT | chr1 | |
| TNNT2-SNP7-F | GAAACCTCCAGGGTCTTTCT | chr1 | rs6704355 |
| TNNT2-SNP7-R | TGGAGCCATTGCAGACTT | chr1 | |
| TNNT2-SNP8-F | CATGCCGGAAGATGACAACA | chr1 | rs1325310 |
| TNNT2-SNP8-R | AAACCCATTGAGCCACTCAG | chr1 | |
| TNNT2-SNP9-F | TAGATGAGCCTCCGGCAA | chr1 | rs112365857 |
| TNNT2-SNP9-R | TTGGCACCTCAGCCTAGT | chr1 | |
| TNNT2-SNP10-F | GGAAAGCCAAGGGTAGAACA | chr1 | rs6427880 |
| TNNT2-SNP10-R | GTGGTCCCAATAACAGGTGTA | chr1 | |

TABLE 15-continued

150 SNP sites and the corresponding primers thereof

| Primer name | Primer | Chromosomal location | Site of amplification |
|---|---|---|---|
| TNNT2-SNP11-F | CATCACCCTGCCTGTATCTTT | chr1 | rs3753969 |
| TNNT2-SNP11-R | GGGAGTAACCAGTGATGAGATG | chr1 | |
| TNNT2-SNP12-F | ATAGGGAGGAATATCGGCTAGG | chr1 | rs12734645 |
| TNNT2-SNP12-R | CTGGAGCTAGGGCATAAGATTC | chr1 | |
| TNNT2-SNP13-F | AGCTGGATGAGTTTGGCTAC | chr1 | rs947379 |
| TNNT2-SNP13-R | GGGCCTGTGATTCTCTGTAAA | chr1 | |
| TNNT2-SNP14-F | TAGTTAGGAGCACGTGGGA | chr1 | rs10920156 |
| TNNT2-SNP14-R | GGCTTATGTGCATCCTTCTCT | chr1 | |
| TNNT2-SNP15-F | GGACCCAGAGCAAATCTAGT | chr1 | rs4915504 |
| TNNT2-SNP15-R | AGGGTTTGGATGAGTCTAAGG | chr1 | |
| TNNT2-SNP16-F | GGAGACTGAGTCGGGAACA | chr1 | rs2799677 |
| TNNT2-SNP16-R | TCTCTGACACTGCTATCTTCTCT | chr1 | |
| TNNT2-SNP17-F | GTCTGAGGAAAGAGACCTGATG | chr1 | rs1256944 |
| TNNT2-SNP17-R | GCTAAAGTGCCTTGCTGAAG | chr1 | |
| TNNT2-SNP18-F | CTTGTCCTTGGTGGGCATTT | chr1 | rs2799670 |
| TNNT2-SNP18-R | TGTCAGAGCACAGGCTGA | chr1 | |
| TNNT2-SNP19-F | CCCAGAGCTGCTGTGAATG | chr1 | rs6677665 |
| TNNT2-SNP19-R | CTTGAGAAGTGGCCTTCTTTGA | chr1 | |
| TNNT2-SNP20-F | GATCCTTCTGATGGCCCAAATA | chr1 | rs3753990 |
| TNNT2-SNP20-R | GGAAGGGTCTTCATCAGCTAAG | chr1 | |
| TNNT2-SNP21-F | GAGAGGCAGAGCTTACTGTG | chr1 | rs10800785 |
| TNNT2-SNP21-R | GGTTATCTGAGGAAGACAGAGATG | chr1 | |
| TNNT2-SNP22-F | CTGGAACCACAGACATGAACTA | chr1 | rs10920215 |
| TNNT2-SNP22-R | CCAGGACTCTGATAATTCCAACA | chr1 | |
| TNNT2-SNP23-F | CTGAGGTGGGTAAAGGGAATG | chr1 | rs12031389 |
| TNNT2-SNP23-R | ATTGAGGCTCAGGGAGGT | chr1 | |
| TNNT2-SNP24-F | AGCTTACTGAGCAAGTGGGAAG | chr1 | rs521075 |
| TNNT2-SNP24-R | TAAACAGAGGCAGGGAGGGT | chr1 | |
| TNNT2-SNP25-F | CTCCTTGCCTCTTCTCTCATTT | chr1 | rs608356 |
| TNNT2-SNP25-R | CAGTCAATCTTTCCGTGTTGC | chr1 | |
| TNNT2-SNP26-F | TCTCTCCCAGAGAGTAGTTACC | chr1 | rs540597 |
| TNNT2-SNP26-R | GTGTGGAGTTTGGCCTCATA | chr1 | |
| TNNT2-SNP27-F | CCCAGTCAACGCTAGGC | chr1 | rs1736450 |
| TNNT2-SNP27-R | TGAGAGAGATGTCGGGAGAG | chr1 | |
| TNNT2-SNP28-F | CTTTGCTCTGTCCAGCACTA | chr1 | rs724220 |
| TNNT2-SNP28-R | CCTTGCACTACATCAGTCTAGC | chr1 | |
| TNNT2-SNP29-F | GATTCTGTTCTGTGCCCTTCT | chr1 | rs490748 |
| TNNT2-SNP29-R | CCTGCACCATGCTTCCTATAC | chr1 | |
| TNNT2-SNP30-F | AGAGCAGCCATGGATCTTG | chr1 | rs12744392 |
| TNNT2-SNP30-R | CATTTCTCCACCTCCAAGACA | chr1 | |

To measure the efficiency of amplifying a given site and allelic dropout (ADO) in order to determine amplification efficiency and whether the amplification was successful, two amplification products (3-1 and 3-2) of the three-step method of Example 2, one amplification product (2-1) of the two-step method of Example 3, and 120 ng of DNA extracted from human epidermal fibroblasts (AFP) cells were randomly selected and subjected to multiplex PCR, respectively (see Table 15 for primers). Composition of amplification system is shown in Table 16, and amplification program is shown in Table 17.

TABLE 16

Multiplex PCR amplification mixture

| | |
|---|---|
| 2 × Taq MaterMix | 25 µl |
| Forward primer, 10 µM | 1 µl |
| Reverse primer, 10 µM | 1 µl |
| Template DNA | 120 ng |
| RNase-free water | Add to a final volume of 50 µl |

TABLE 17

Multiplex PCR amplification program

| Cycle number | Temperature (centigrade) | Time |
|---|---|---|
| 1 | 95 | 10 min |
| 10 | 95 | 30 s |
|  | 60, decreased by 1° C. each cycle | 30 s |
|  | 72 | 45 s |
| 30 | 95 | 30 s |
|  | 50 | 30 s |
|  | 72 | 45 s |
|  | 72 | 5 min |
| 1 | 4 | Maintained |

The amplification products were constructed into a genomic library by means of fragmentation, and sequenced with hiseq2500 sequencer, with an average sequencing depth of 5 Mb (see FIG. 10 for statistical results). Multiplex PCR data show that: there was no significant difference among index parameters such as GC content, high-quality data (high_quality_of_raw), unique mapped ratio of raw data (unique_mapped_of_raw), and average coverage (average depth) of amplification products of the three types of samples described above.

In addition, results of second-generation sequencing analysis show that a total of 23 homozygous loci were detected in multiplex PCR products using gDNA as starting material. Of these 23 homozygous loci, 23 and 22 were detected respectively in the two amplification products of the three-step method of Example 2; 21 were detected in amplification product from the two-step method of Example 3. There was no significant difference between ADO proportion of homozygous loci of amplification product of Example 2 and that of Example 3. See Table 18 for detailed data.

TABLE 18

Comparison of ADO of amplification product of Example 3 and of amplification product of Example 2 in gDNA homozygous loci

|  | Homozygous loci | | |
|---|---|---|---|
|  | 2_1 | 3_1 | 3_2 |
| 23 (gDNA) | 1/21 | 1/23 | 0/22 |
| ADO | 4.7619 | 4.34783 | 0 |
| Amplification efficiency | 91.30% | 100% | 95.65% |

Second-generation sequencing analysis results showed that a total of 62 heterozygous loci were detected in multiplex PCR products using gDNA as starting material. Of these 62 heterozygous loci, 59 and 56 were detected respectively in the two samples of Example 2; 51 were detected in one sample of Example 3. There was no significant difference between ADO proportion of heterozygous loci of amplification product of Example 2 and that of Example 3. See Table 19 for detailed data.

TABLE 19

Comparison of ADO of amplification product of Example 3 and of amplification product of Example 2 in gDNA homozygous loci

|  | Homozygous loci | | |
|---|---|---|---|
|  | 2_1 | 3_1 | 3_2 |
| 62 (gDNA) | 4/51 | 1/59 | 4/56 |
| ADO | 7.84314 | 1.69492 | 7.14286 |
| Amplification efficiency | 82.2581 | 95.1613 | 90.3226 |

Example 5: Genomic Amplification Using a Method in which Lysing and Amplification are Completed in One Step (Referred to as One-Step Method)

The method of the present example is also referred to as one-step method herein, because lysing of cell, pre-amplification and exponential amplification were combined and completed within one step.

Human epidermal fibroblasts were isolated and lysed according to the method of Example 1 to obtain single-cell genomic DNA.

Amplification mixture was prepared, which contained $Na^+$, $Mg^{2+}$, $Cl^-$, Tris-Cl, dNTP, TritonX-100, Vent polymerase, primer of SEQ ID NO:1, primer of SEQ ID NO:12, and primer of SEQ ID NO:13.

TABLE 20

One-step amplification program of the present application

| Cycle number | Temperature (Centigrade) | Time |
|---|---|---|
| 1 | 50 | 20 min |
|  | 80 | 10 min |
|  | 94 | 3 min |
| 8 | 10 | 20 s |
|  | 30 | 30 s |
|  | 50 | 40 s |
|  | 70 | 2 min |
|  | 95 | 20 s |
| 1 | 94 | 30 s |
| 17 | 94 | 20 s |
|  | 58 | 15 s |
|  | 72 | 2 min |
| 1 | 72 | 5 min |
|  | 4 | Maintained |

Example 6: Comparison of Amplification Product from the One-Step Method of Example 5 and that from the Three-Step Method of Example 2

Gel Electrophoresis 5 microliters of unpurified amplification product from the three-step method of Example 2 and unpurified amplification product from the one-step method of Example 5 were taken, respectively, and were respectively added with 1 microliter of 6×DNA loading buffer (purchased from Beijing ComWin Biotech Co., Ltd., Cat. No. CW0610A) for sample loading. 1% agarose gel was used as the gel, and DM2000 (purchased from Beijing ComWin Biotech Co., Ltd., Cat. No. CW0632C) was used as the marker.

Figure 11:
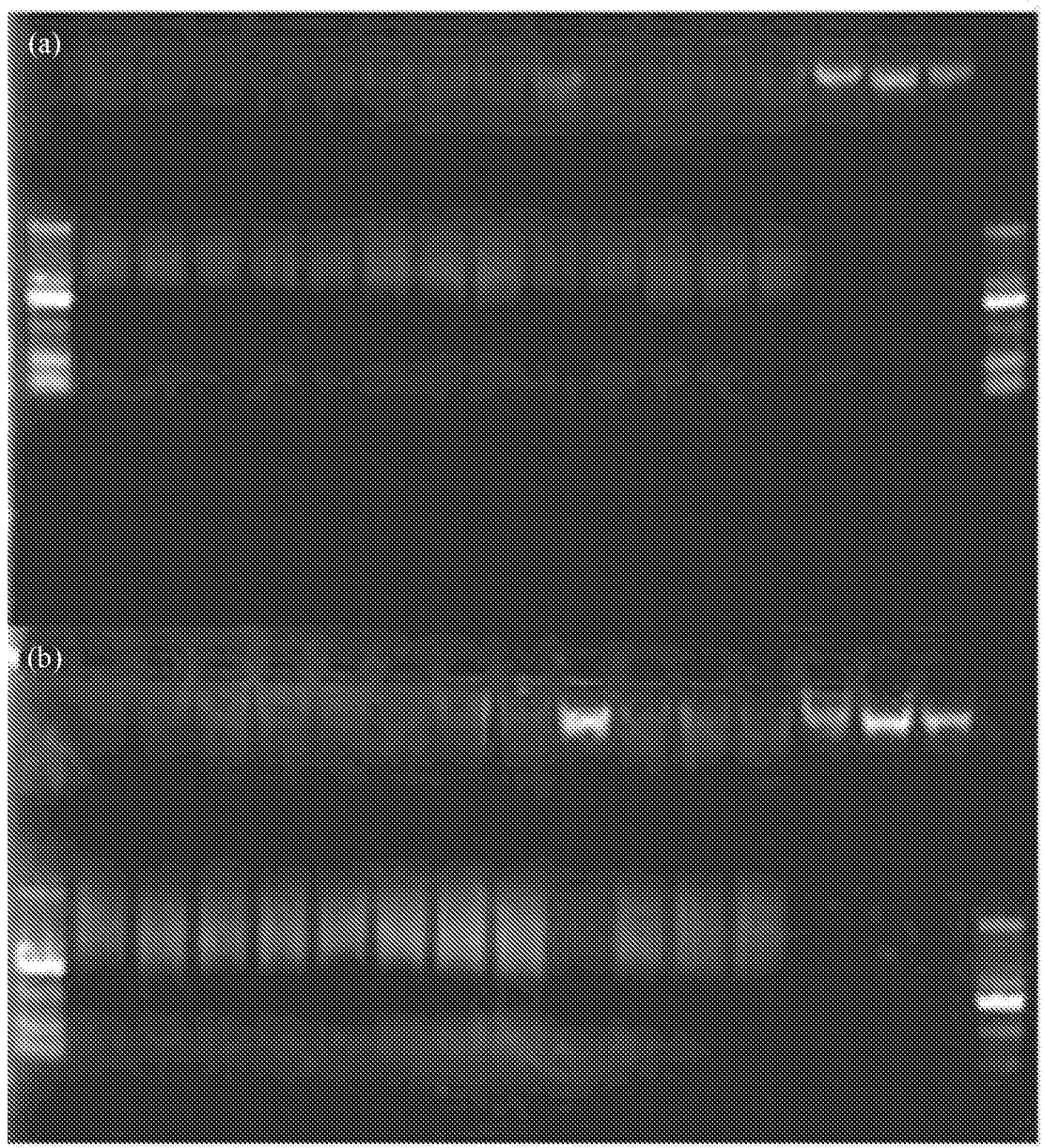
FIG. 11 shows results of gel electrophoresis of amplification products obtained by amplifying genomic DNA of normal human epidermal fibroblasts (AFP) using the three-step method of Example 2 and using the one-step method of Example 5, respectively, wherein a shows amplification result of the one-step method of Example 5 (from left to right, lane 1, molecular-weight marker; lanes 2-11, single-cell amplification samples; lanes 12-14, positive control (40 pg gDNA); Lanes 15-17, negative control; lane 18, molecular-weight marker); b represents the amplification results of the three-step method of Example 2 (from left to right, lane 1, molecular-weight marker; lanes 2-11, single-cell amplification samples; lanes 12-14, positive control (40 pg gDNA); Lanes 15-17, negative control; lane 18, molecular-weight marker).

See FIG. 11 for electrophoresis, wherein the first row shows the one-step amplification result of Example 5 (from left to right, lane 1, molecular-weight marker; lanes 2-11, single-cell amplification samples; lanes 12-14, positive control (40 pg gDNA); lanes 15-17, negative control (free of genomic DNA); lane 18, molecular-weight marker). Electrophoresis show that: the band position and brightness of the one-step amplification product of Example 5 were comparable to those of the three-step amplification product of Example 2, with no significant difference.

Purification Product 50 microliters of unpurified amplification products from the three-step method of Example 2 and from the one-step method of Example 5 were taken, and the amplification products were purified with a universal column purification kit (purchased from Beijing ComWin Biotech Co., Ltd., Cat. No. CW2301), the purification steps of which were performed in accordance with the kit instructions. 50 microliters of EB was used for elution. After purification was completed, 2 μl of the purified product was subject to concentration measurement using Nanodrop (AOSHENG, NANO-100). Results of concentration measurement are shown in Table 21.

TABLE 21

Concentration of amplification products after purification

| One-step method | Concentration (ng/μl) | Three-step method | Concentration (ng/μl) |
| --- | --- | --- | --- |
| 1-1 | 49.481 | 3-1 | 47.044 |
| 1-2 | 51.956 | 3-2 | 46.268 |
| 1-3 | 40.976 | 3-3 | 71.316 |
| 1-4 | 45.041 | 3-4 | 73.675 |
| 1-5 | 57.89 | 3-5 | 68.86 |
| 1-6 | 49.494 | 3-6 | 64.411 |
| 1-7 | 47.94 | 3-7 | 52.018 |
| 1-8 | 65.17 | 3-8 | 49.532 |
| 1-9 | 36.519 | 3-9 | No amplification product |
| 1-10 | 39.538 | 3-10 | 13.157 |
| Mean | 48.401 | Mean | 54.031 |

Concentration measurement results show that: post-purification concentration of amplification products obtained by the two amplification methods after purification were comparable, with no significant difference.

Pathogenic Site Detection

Twenty pathogenic sites were randomly selected and primers were designed. The selected pathogenic sites and their corresponding primers are shown in Table 6 and Table 7 in Example 4, respectively.

Four samples amplified according to Example 2 and four samples amplified according to Example 5 were randomly selected as template DNA, respectively. Composition of amplification system and amplification program are as shown in Tables 8 and 9 in Example 4, respectively, except that the cycle numbers in FIGS. 12(*a*) and 12(*b*) were 30 cycles. The 20 pathogenic sites above were respectively amplified by PCR using dye-containing 2×Taq MasterMix (purchased from Beijing ComWin Biotech Co., Ltd., Cat. No. CW0682).

Figure 12:
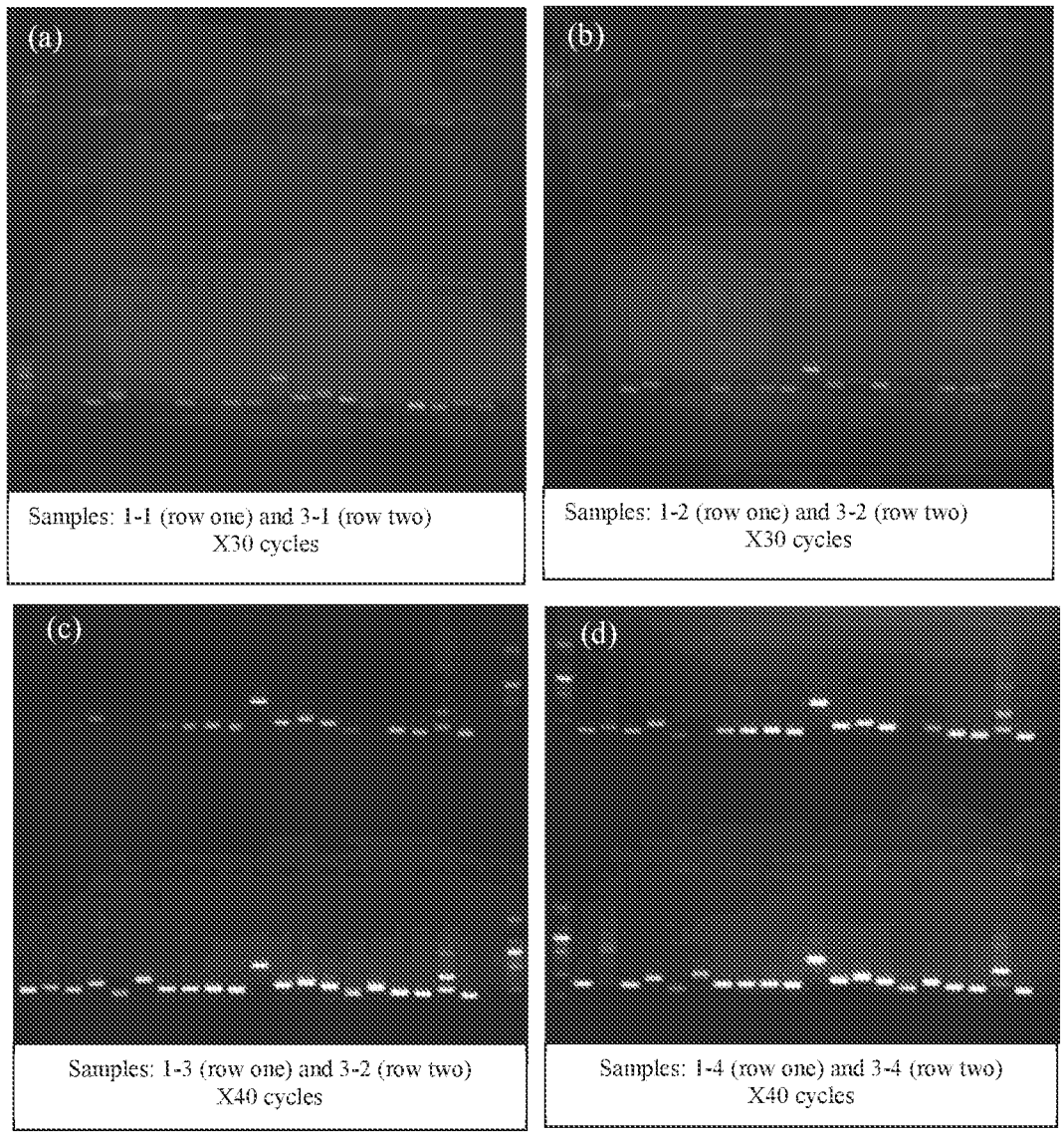
FIG. 12 shows results of gel electrophoresis of the following: genomic DNA of normal human epidermal fibroblasts (AFP) was amplified using the three-step method of Example 2 and the one-step method of Example 5, respectively, and 4 samples were randomly selected from the amplification products obtained from the two methods (i.e. a total of 8 samples) as templates, respectively, and amplification for the 20 pathogenic sites as shown in Table 6 was performed using primers shown in Table 7, respectively, and the amplification products were subject to gel electrophoresis. a-d represent gel electrophoresis images of products of repeated single-cell genomic DNA amplification, respectively, wherein the upper-row bands indicate results of amplification using the two-step method and the lower-row bands indicate results of amplification using the three-step method (a: Upper-row corresponds to sample 1_1 and lower-row corresponds to sample 3_1; b: Upper-row corresponds to sample 1_2 and lower-row corresponds to sample 3_2; c: Upper-row corresponds to sample 1_3 and lower-row corresponds to sample 3_3; d: Upper-row corresponds to sample 1_4 and lower-row corresponds to sample 3_4. In each electrophoresis image, from left to right, lanes sequentially indicate amplification results for pathogenic sites 1-20 shown in Table 6.

Amplification results are as shown in FIG. 12. The amplification results show that: there was no significant difference in amplification accuracy and amount of amplification products between the two methods.

Figure 13:
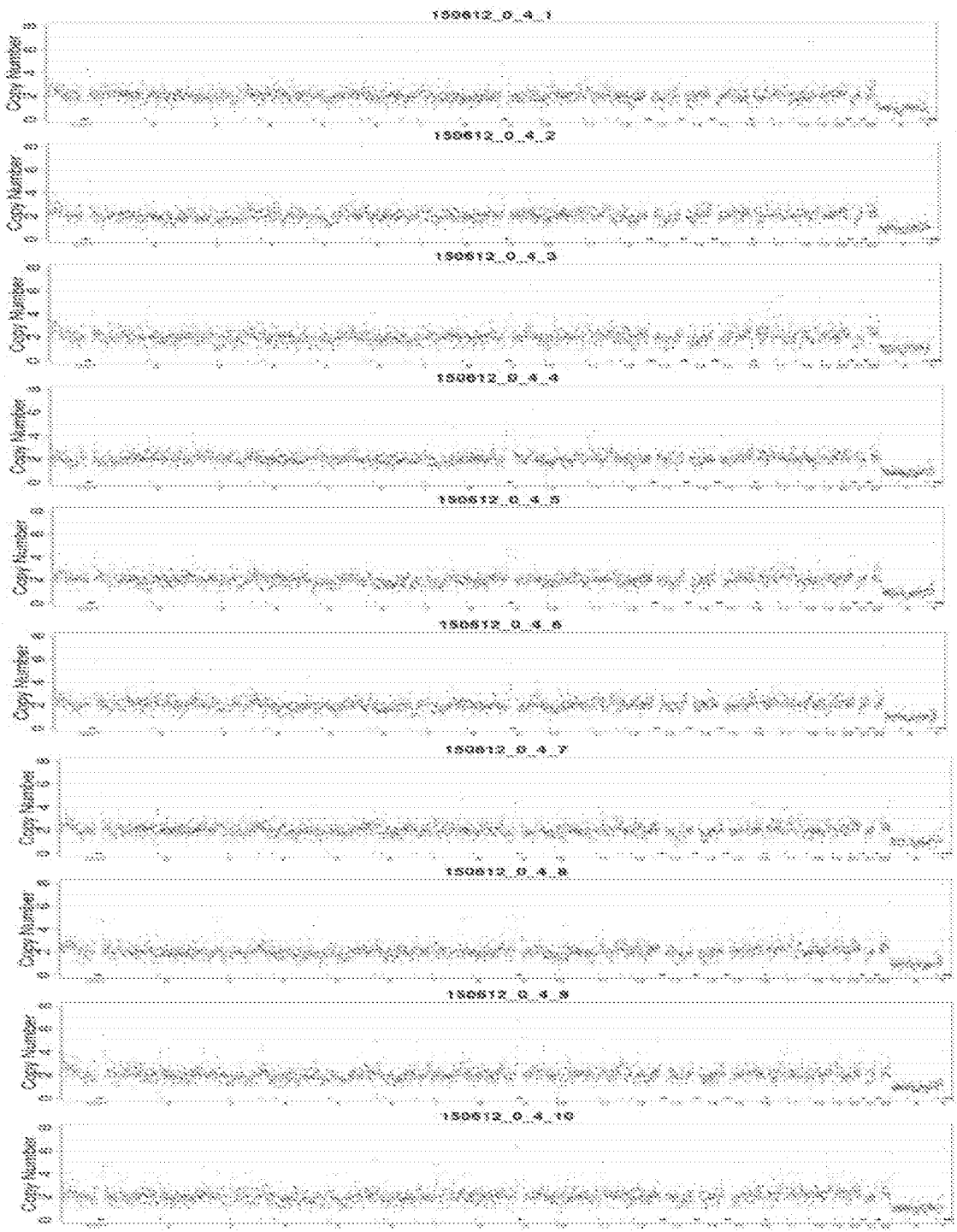
FIG. 13 shows results of chromosome copy number obtained by sequencing genomic libraries constructed using amplification products obtained by amplifying genomic DNA of normal human epidermal fibroblasts (AFP) using the one-step method of Example 5, wherein the vertical ordinate represents chromosome copy number, which is 2 in normal persons; the horizontal ordinate represents chromosomes 1-22 and sex chromosomes, wherein a-j represent results of chromosome copy number obtained by sequencing genomic libraries constructed with samples 1_1, 1_2, 1_3, 1_4, 1_5, 1_6, 1_7, 1_8, 1_9 and 1_10, respectively.
Figure 14:
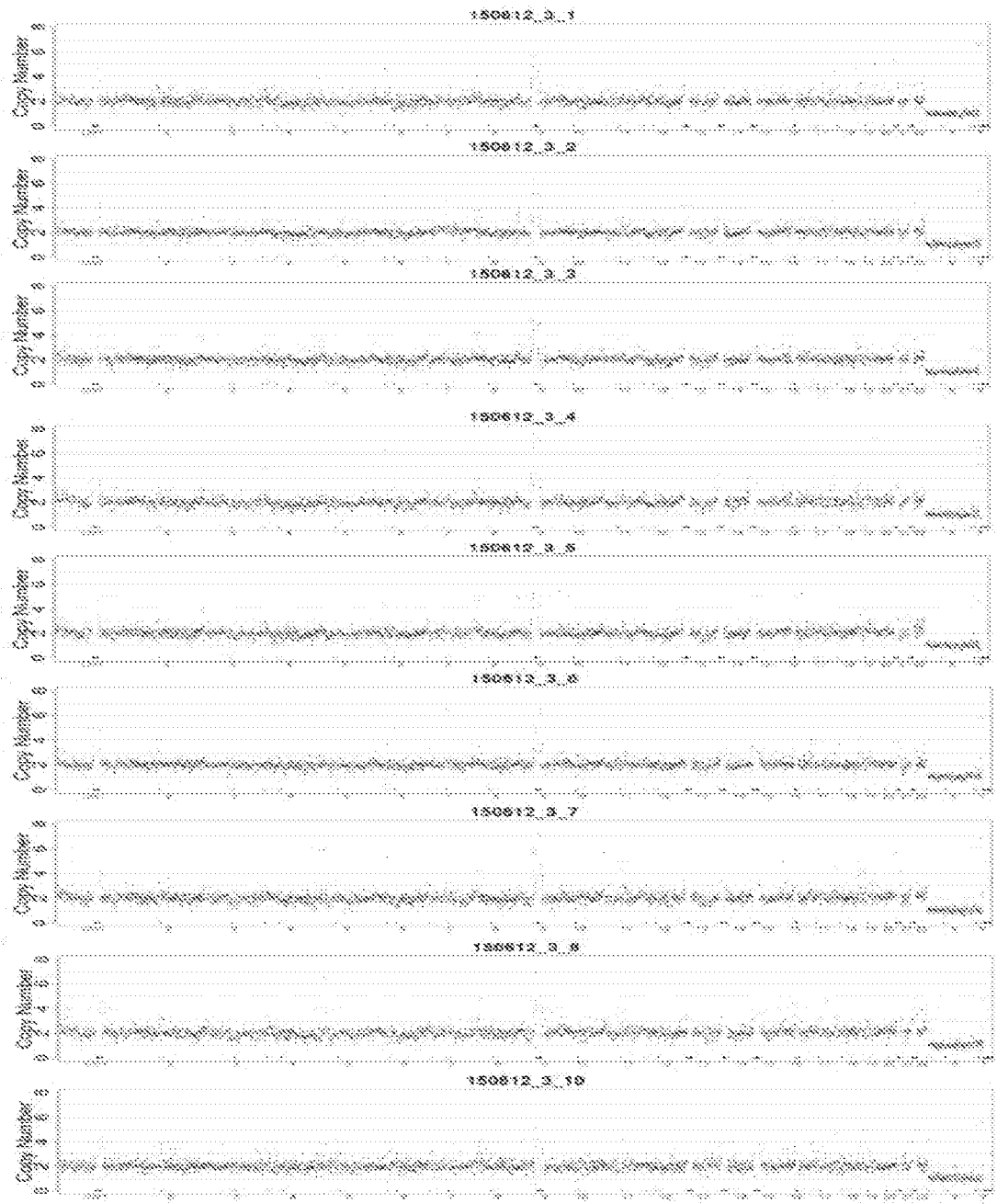
FIG. 14 shows results of chromosome copy number obtained by sequencing genomic libraries constructed using amplification products obtained by amplifying genomic DNA of normal human epidermal fibroblasts (AFP) using the three-step method of Example 2, wherein the vertical ordinate represents chromosome copy number, which is 2 in normal persons; the horizontal ordinate represents chromosomes 1-22 and sex chromosomes, wherein a-i represent results of chromosome copy number obtained by sequencing genomic libraries constructed with samples 3_1, 3_2, 3_3, 3_4, 3_5, 3_6, 3_7, 3_8 and 3_10, respectively.

Gene Sequencing 10 purified products amplified by the three-step method of Example 2 (shown as 2-1, 2-2, 2-3, 2-4, 2-5, 2-6, 2-7, 2-8, 2-9, 2-10 in FIG. 14) and 10 purified products amplified by the one-step method of Example 5 (shown as 1-1, 1-2, 1-3, 1-4, 1-5, 1-6, 1-7, 1-8, 1-9, 1-10 in FIG. 13) were randomly selected, constructed into genomic library through fragmentation, and sequenced with hiseq2500 sequencer by means of shallow sequencing. For each sample, a data volume of 1.5 Mb was measured, and the sequence obtained by sequencing was mapped to human reference genome (hg19).

Results of the one-step method in Example 5 are as shown in FIG. 13, and results of the three-step method in Example 2 are as shown in FIG. 14, wherein the vertical ordinate represents chromosome copy number, which is 2 in normal persons; the horizontal ordinate represents chromosomes 1-22 and sex chromosomes. The above results show that: chromosomal detection of cells by the three-step method of Example 2 and by the two-step method of Example 3 have consistent results.

In sequencing results, various index parameters of high-throughput sequencing results are also provided, as shown in FIG. 15, wherein the "unique reads ratio mapped to human genome" in raw data (i.e., unique_mapped_of_raw) is the most important measuring index. The average unique_mapped_of_raw of all samples of the one-step method in Example 5 was 79.13%, while that of all samples of the three-step method in Example 2 was 74.25%, which indicating that the ratio of unique_mapped_of_raw among amplification samples of the one-step method of Example 5 was significantly higher than that for amplification samples of the three-step method of Example 2.

Figure 16:
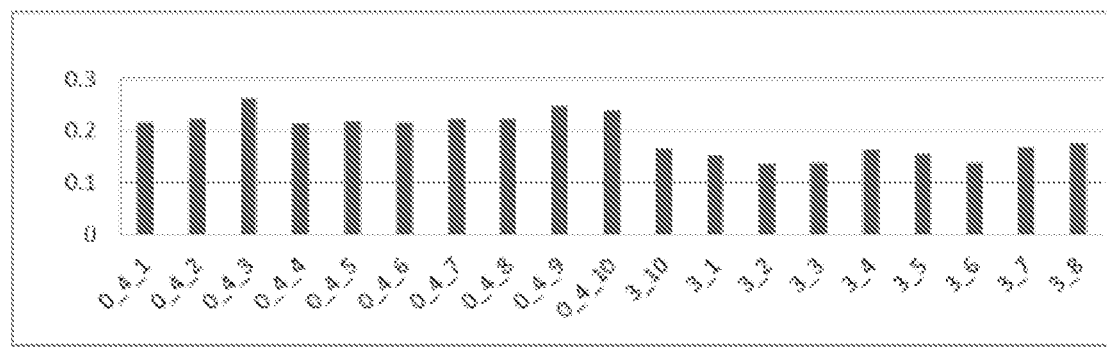
FIG. 16 shows comparison results of copy number variation coefficient after second-generation sequencing of genomic libraries constructed with the amplification products obtained by amplifying genomic DNA of normal human epidermal fibroblasts (AFP) using the three-step method of Example 2 and using the one-step method of Example 5, respectively.

The copy-number variation coefficient can be used to compare the dispersion degree of sample copy-number, after the sample is amplified by the two types of amplification methods. The average copy-number variation coefficient of all amplified samples using the one-step method of Example 5 was close to that of all amplified samples using the three-step method of Example 2. See FIG. 16 for detailed data.

Although various aspects and embodiments have been disclosed by the present disclosure, other aspects and embodiments will be apparent to those skilled in the art. The various aspects and embodiments disclosed herein are for the purpose of illustration only, and are not intended to limit the scope of the present disclosure. The actual scope of the protection of the present disclosure is governed by the claims.

What is claimed is:

1. A method of amplifying genomic DNA of a cell, comprising:
   (a) providing a reaction mixture, wherein the reaction mixture comprises the genomic DNA, a first type of primer, a second type of primer, a mixture of nucleotide monomers, and a nucleic acid polymerase, wherein the first type of primer comprises, in a 5' to 3' orientation, a common sequence and a variable sequence, wherein the common sequence consists of three or two types of bases selected from the group consisting of four types of bases: G, A, C and T, provided that the common sequence does not comprise G and C at the same time, and wherein the second type of primer comprises the common sequence but not the variable sequence;
   (b) placing the reaction mixture to a first thermal cycle program such that the variable sequence of the first type of primer can pair with the genomic DNA and amplify the genomic DNA to obtain a genomic amplification product, wherein the genomic amplification product comprises the common sequence at its 5' end and comprises the complementary sequence of the common sequence at its 3' end;
   (c) placing the reaction mixture obtained from step (b) to a second thermal cycle program, such that the common sequence of the second type of primer can pair with the 3' end of the genomic amplification product and amplify the genomic amplification product to obtain an expanded genomic amplification product,
   wherein the reaction mixture is provided prior to the step (b).

2. The method of claim 1, further comprising analyzing the amplification product to identify disease- or phenotype-associated sequence features.

3. The method of claim 2, wherein the disease- or phenotype-associated sequence features include chromosomal abnormalities, chromosomal translocation, aneuploidy, partial or complete chromosomal deletion or duplication, fetal HLA haplotypes and paternal mutations, or the disease or phenotype is selected from the group consisting of: beta-thalassemia, Down's syndrome, cystic fibrosis, sickle cell disease, Tay-Sachs disease, Fragile X syndrome, and spinal muscular.

4. The method of claim 1, wherein the genomic DNA is contained within a cell, and the reaction mixture further comprises a surfactant and/or a lyase capable of lysing the cell.

5. The method of claim 1, further comprising placing the reaction mixture to a lysing thermal cycle program prior to said steps (b) and (c), such that the cell is lysed and the genomic DNA is released.

6. The method of claim 1, wherein the common sequence is selected such that the common sequence does not substantially bind to genomic DNA to cause amplification.

7. The method of claim 1, wherein the common sequence is selected from the group consisting of SEQ ID NO: 1, SEQ ID NO: 2, SEQ ID NO: 3, SEQ ID NO: 4, SEQ ID NO: 5, and SEQ ID NO: 6.

8. The method of claim 1, wherein the variable sequence comprises a random sequence.

9. The method of claim 1, wherein the variable sequence has a length of 2-20 bases, 3-10 bases, 4-9 bases, or 5-8 bases.

10. The method of claim 1, wherein three or more base positions in the variable sequence consist of one or more types of bases selected from G, A and T, or consist of one or more types of bases selected from C, A and T.

11. The method of claim 10, wherein the three or more base positions are located at the 3' end or in the middle of the variable sequence.

12. The method of any of claims 1-11, wherein the variable sequence is selected from the group consisting of (N)nGGG, (N)nTTT, (N)mTNTNG, and (N)xGTGG(N)y, wherein N refers to any nucleotide that can pair with a naturally occurring nucleic acid, n is a positive integer selected from 3-17, m is a positive integer selected from 3-15, x and y are positive integers selected from 3-13, respectively.

13. The method of claim 1, wherein the variable sequence is selected such that the variable sequence is homogeneously distributed in the genome and with a high coverage.

14. The method of claim 1, wherein the first type of primer includes a sequence of SEQ ID NO: 11 [GTGAGTGATGGTTGAGGTAGTGTGGAG], SEQ ID NO: 12 [GTGAGTGATGGTTGAGGTAGTGTGGAG GGG], SEQ ID NO: 13 [GTGAGTGATGGTTGAGGTAGTGTGGAG TTT], SEQ ID NO: 14 [GTGAGTGATGGTTGAGGTAGTGTGGAGNNNTNTNG] or SEQ ID NO: 15 [GTGAGTGATGGTTGAGGTAGTGTGGAG-NNNGTGGNN], and the second type of primer, in a 5' to 3' orientation, has a sequence of SEQ ID NO: 1 [GTGAGTGATGGTTGAGGTAGTGTGGAG], wherein N is any nucleotide that can pair with a naturally occurring nucleic acid.

15. The method of claim 1, wherein the reaction mixture further comprises a pH adjusting agent, such that the pH of the reaction mixture is maintained between 7.0-9.0.

16. The method of claim 1, wherein the first thermal cycle program included:
(b1) placing the reaction mixture to a thermal program capable of opening double strands of the genomic DNA;
(b2) placing the reaction mixture to a thermal program that enables binding of the first type of primer to single-strand DNA template;
(b3) placing the reaction mixture to a thermal program that enables extension of the length of the first type of primer that binds a single-strand DNA template under the action of the nucleic acid polymerase, to produce an amplification product;
(b4) placing the reaction mixture to a thermal program capable of denaturing the amplification product into single strands;
(b5) repeating steps (b2) to (b4) to a designated first cycle number.

17. The method of claim 16, wherein the designated first cycle number is more than 2.

18. The method of claim 16, after proceeding to the second cycle, the amplification product comprises a genomic amplification product comprising the common sequence at the 5' end and a complementary sequence of the common sequence at the 3' end.

19. The method of claim 16, further comprising a step (b4') after step (b4) and prior to step (b5), wherein the reaction mixture is placed in a suitable thermal program enabling hybridization of the 3' end and 5' end of the genomic amplification product to form a loop structure, or enabling binding of the 3' end of the genomic amplification product to a primer.

20. The method of claim 16, the method goes directly to step (b5) after step (b4).

21. The method of claim 16, wherein the first cycle number of the step (b5) is more than 3, more than 4, more than 5, or more than 6; and no more than 10.

22. The method of claim 16, wherein the step (c) comprises:
(c1) placing the reaction mixture from step (b) to a thermal program capable of opening DNA double strands;
(c2) placing the reaction mixture to a thermal program that enables binding of the second type of primer to single strands of the genomic amplification product from step (b);
(c3) placing the reaction mixture to a thermal program that enables extension of the length of the second type of primer that binds to single strands of the amplification products, under the action of the nucleic acid polymerase;
(c4) repeating steps (c1) to (c3) to a designated second cycle number.

23. The method of claim 22, wherein the second cycle number in the step (c4) is greater than the first cycle number in the step (b5).

24. The method of claim 16, wherein the thermal program in the step (b1) comprises allowing reacting for 1-10 minutes at a temperature between 90-95° C.

25. The method of claim 16, wherein the step (b2) comprises placing the reaction mixture to more than one thermal program to promote sufficient and efficient binding of the first type of primer to the DNA template.

26. The method of claim 25 wherein the more than one thermal program comprises: a first temperature between 5-10° C., a second temperature between 25-30° C., and a third temperature between 45-50° C.

27. The method of claim 16, wherein the step (b2) comprises allowing reacting at a first temperature for 3-50 s, allowing reacting at a second temperature for 3-50 s, and allowing reacting at a third temperature for 3-50 s.

28. The method of claim 16, wherein the thermal program in the step (b3) comprises allowing reacting at a temperature of 60-90° C. for 1-15 minutes.

29. The method of claim 16, wherein the thermal program in the step (b4) comprises allowing reacting at a temperature of 90-95° C. for 10-50 s.

30. The method of claim 22, wherein the thermal program in the step (c1) comprises allowing reacting at a temperature of 90-95° C. for 10-30 s.

31. The method of claim 22, wherein the thermal program in the step (c2) comprises allowing reacting at a temperature of 45-65° C. for 10-30 s.

32. The method of claim 22, wherein the thermal program in the step (c3) comprises allowing reacting at a temperature of 60-80° C. for 1-15 minutes.

33. The method of claim 1, wherein the genomic DNA in the step (a) is released from a lysed cell, and the lysing includes thermal lysis, base lysis, enzymatic lysing or mechanical lysing.

34. The method of claim 33, wherein the thermal lysing comprises lysing at a temperature between 20-100° C. for 10-100 minutes.

35. The method of claim 33, where the thermal lysing is carried out in presence of a lysis reagent.

36. The method of claim 35, wherein the lysis reagent includes one or more surfactants selected from the group consisting of: NP-40, Tween, SDS, Triton X-100, EDTA, and guanidinium isothiocyanate, and/or lyase.

* * * * *

SEQUENCE LISTING

<160> NUMBER OF SEQ ID NOS: 407

<210> SEQ ID NO 1
<211> LENGTH: 27
<212> TYPE: DNA
<213> ORGANISM: Artificial Sequence
<220> FEATURE:
<223> OTHER INFORMATION: Primer

<400> SEQUENCE: 1

```
gtgagtgatg gttgaggtag tgtggag                                          27
```

<210> SEQ ID NO 2
<211> LENGTH: 24
<212> TYPE: DNA
<213> ORGANISM: Artificial Sequence
<220> FEATURE:
<223> OTHER INFORMATION: Primer

<400> SEQUENCE: 2

```
gtggagttag tgagtgtaat ggat                                             24
```

<210> SEQ ID NO 3
<211> LENGTH: 24
<212> TYPE: DNA
<213> ORGANISM: Artificial Sequence
<220> FEATURE:
<223> OTHER INFORMATION: Primer

<400> SEQUENCE: 3

```
ggtttggtgt ggtgtgtggt ggtg                                             24
```

<210> SEQ ID NO 4
<211> LENGTH: 25
<212> TYPE: DNA
<213> ORGANISM: Artificial Sequence
<220> FEATURE:
<223> OTHER INFORMATION: Primer

<400> SEQUENCE: 4

```
acaacactat caatccctat cctac                                            25
```

<210> SEQ ID NO 5
<211> LENGTH: 24
<212> TYPE: DNA
<213> ORGANISM: Artificial Sequence
<220> FEATURE:
<223> OTHER INFORMATION: Primer

<400> SEQUENCE: 5

```
atggtagtgg gtagatgatt aggt                                             24
```

<210> SEQ ID NO 6
<211> LENGTH: 26
<212> TYPE: DNA
<213> ORGANISM: Artificial Sequence
<220> FEATURE:
<223> OTHER INFORMATION: Primer

<400> SEQUENCE: 6

```
catatcccta tacctaatac cattac                                           26
```

<210> SEQ ID NO 7
<211> LENGTH: 8
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(5)
<223> OTHER INFORMATION: n is a, c, g, or t

<400> SEQUENCE: 7

```
nnnnnggg                                                                8
```

```
<210> SEQ ID NO 8
<211> LENGTH: 8
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(5)
<223> OTHER INFORMATION: n is a, c, g, or t

<400> SEQUENCE: 8 nnnnnttt                                                                  8

<210> SEQ ID NO 9
<211> LENGTH: 8
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (7)..(7)
<223> OTHER INFORMATION: n is a, c, g, or t

<400> SEQUENCE: 9 nnntntng                                                                  8

<210> SEQ ID NO 10
<211> LENGTH: 9
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (8)..(9)
<223> OTHER INFORMATION: n is a, c, g, or t

<400> SEQUENCE: 10 nnngtggnn                                                                 9

<210> SEQ ID NO 11
<211> LENGTH: 35
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (28)..(35)
<223> OTHER INFORMATION: n is a, c, g, or t

<400> SEQUENCE: 11
gtgagtgatg gttgaggtag tgtggagnnn nnnnn                                    35

<210> SEQ ID NO 12
<211> LENGTH: 35
```

```
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (28)..(32)
<223> OTHER INFORMATION: n is a, c, g, or t

<400> SEQUENCE: 12
gtgagtgatg gttgaggtag tgtggagnnn nnggg                              35

<210> SEQ ID NO 13
<211> LENGTH: 35
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (28)..(32)
<223> OTHER INFORMATION: n is a, c, g, or t

<400> SEQUENCE: 13
gtgagtgatg gttgaggtag tgtggagnnn nnttt                              35

<210> SEQ ID NO 14
<211> LENGTH: 35
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (28)..(30)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (34)..(34)
<223> OTHER INFORMATION: n is a, c, g, or t

<400> SEQUENCE: 14
gtgagtgatg gttgaggtag tgtggagnnn tntng                              35

<210> SEQ ID NO 15
<211> LENGTH: 36
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (28)..(30)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t

<400> SEQUENCE: 15
gtgagtgatg gttgaggtag tgtggagnnn gtggnn                             36

<210> SEQ ID NO 16
<211> LENGTH: 27
<212> TYPE: DNA
<213> ORGANISM: Artificial Sequence
<220> FEATURE:
```

<223> OTHER INFORMATION: Primer

<400> SEQUENCE: 16
agtgattgtc attgaaattg gtgattc                                27

<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17
agccaatgac tccctttgac                                       20

<210> SEQ ID NO 18
<211> LENGTH: 22
<212> TYPE: DNA
<213> ORGANISM: Artificial Sequence
<220> FEATURE:
<223> OTHER INFORMATION: Primer

<400> SEQUENCE: 18
cagagcgatg acatcttaac ct                                    22

<210> SEQ ID NO 19
<211> LENGTH: 21
<212> TYPE: DNA
<213> ORGANISM: Artificial Sequence
<220> FEATURE:
<223> OTHER INFORMATION: Primer

<400> SEQUENCE: 19
gtgaacacca gggcagatga g                                     21

<210> SEQ ID NO 20
<211> LENGTH: 25
<212> TYPE: DNA
<213> ORGANISM: Artificial Sequence
<220> FEATURE:
<223> OTHER INFORMATION: Primer

<400> SEQUENCE: 20
tgtcccttgt ggtttttgc atttc                                  25

<210> SEQ ID NO 21
<211> LENGTH: 25
<212> TYPE: DNA
<213> ORGANISM: Artificial Sequence
<220> FEATURE:
<223> OTHER INFORMATION: Primer

<400> SEQUENCE: 21
tttcgtccaa gcatctcaaa gagtc                                 25

<210> SEQ ID NO 22
<211> LENGTH: 23
<212> TYPE: DNA
<213> ORGANISM: Artificial Sequence
<220> FEATURE:
<223> OTHER INFORMATION: Primer

<400> SEQUENCE: 22
ctcttcttac cctgcaccca gag                                   23

```
<210> SEQ ID NO 23
<211> LENGTH: 27
<212> TYPE: DNA
<213> ORGANISM: Artificial Sequence
<220> FEATURE:
<223> OTHER INFORMATION: Primer

<400> SEQUENCE: 23
gcattttcgt ccaagcatct caaagag                                    27

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24
aagaacaagt cagggtcaat                                            20

<210> SEQ ID NO 25
<211> LENGTH: 30
<212> TYPE: DNA
<213> ORGANISM: Artificial Sequence
<220> FEATURE:
<223> OTHER INFORMATION: Primer

<400> SEQUENCE: 25
ttaaaatact tttcaagtta tagttctttt                                 30

<210> SEQ ID NO 26
<211> LENGTH: 24
<212> TYPE: DNA
<213> ORGANISM: Artificial Sequence
<220> FEATURE:
<223> OTHER INFORMATION: Primer

<400> SEQUENCE: 26
gtgaaacatc ttaaggcttg aaag                                       24

<210> SEQ ID NO 27
<211> LENGTH: 24
<212> TYPE: DNA
<213> ORGANISM: Artificial Sequence
<220> FEATURE:
<223> OTHER INFORMATION: Primer

<400> SEQUENCE: 27
taacaagtgc ttgtctgata taat                                       24

<210> SEQ ID NO 28
<211> LENGTH: 23
<212> TYPE: DNA
<213> ORGANISM: Artificial Sequence
<220> FEATURE:
<223> OTHER INFORMATION: Primer

<400> SEQUENCE: 28
aaaagctgag aagttcagaa aac                                        23

<210> SEQ ID NO 29
<211> LENGTH: 26
<212> TYPE: DNA
<213> ORGANISM: Artificial Sequence
<220> FEATURE:
<223> OTHER INFORMATION: Primer
```

-continued

<400> SEQUENCE: 29
aaatttgtat ttaacaagtg cttgtc                                          26

<210> SEQ ID NO 30
<211> LENGTH: 23
<212> TYPE: DNA
<213> ORGANISM: Artificial Sequence
<220> FEATURE:
<223> OTHER INFORMATION: Primer

<400> SEQUENCE: 30
gtttattctc tggtcatcct ggt                                             23

<210> SEQ ID NO 31
<211> LENGTH: 22
<212> TYPE: DNA
<213> ORGANISM: Artificial Sequence
<220> FEATURE:
<223> OTHER INFORMATION: Primer

<400> SEQUENCE: 31
ggtgttcaga ggaagtgaga tt                                              22

<210> SEQ ID NO 32
<211> LENGTH: 20
<212> TYPE: DNA
<213> ORGANISM: Artificial Sequence
<220> FEATURE:
<223> OTHER INFORMATION: Primer

<400> SEQUENCE: 32
gaactctcaa cctgcctctg                                                 20

<210> SEQ ID NO 33
<211> LENGTH: 20
<212> TYPE: DNA
<213> ORGANISM: Artificial Sequence
<220> FEATURE:
<223> OTHER INFORMATION: Primer

<400> SEQUENCE: 33
cttgatgagg atgccgttct                                                 20

<210> SEQ ID NO 34
<211> LENGTH: 23
<212> TYPE: DNA
<213> ORGANISM: Artificial Sequence
<220> FEATURE:
<223> OTHER INFORMATION: Primer

<400> SEQUENCE: 34
ccattcaagg aacaacagct aaa                                             23

<210> SEQ ID NO 35
<211> LENGTH: 21
<212> TYPE: DNA
<213> ORGANISM: Artificial Sequence
<220> FEATURE:
<223> OTHER INFORMATION: Primer

<400> SEQUENCE: 35
acccaggcaa agactaaaga g                                               21

<210> SEQ ID NO 36
<211> LENGTH: 20

<212> TYPE: DNA
<213> ORGANISM: Artificial Sequence
<220> FEATURE:
<223> OTHER INFORMATION: Primer

<400> SEQUENCE: 36
gacgccaagt ttgaaggaac                                        20

<210> SEQ ID NO 37
<211> LENGTH: 23
<212> TYPE: DNA
<213> ORGANISM: Artificial Sequence
<220> FEATURE:
<223> OTHER INFORMATION: Primer

<400> SEQUENCE: 37
ctactgctag aaacagccta ctc                                    23

<210> SEQ ID NO 38
<211> LENGTH: 20
<212> TYPE: DNA
<213> ORGANISM: Artificial Sequence
<220> FEATURE:
<223> OTHER INFORMATION: Primer

<400> SEQUENCE: 38
tcgcattatg atcctcgttg                                        20

<210> SEQ ID NO 39
<211> LENGTH: 20
<212> TYPE: DNA
<213> ORGANISM: Artificial Sequence
<220> FEATURE:
<223> OTHER INFORMATION: Primer

<400> SEQUENCE: 39
ggacacaaag cagtccacag                                        20

<210> SEQ ID NO 40
<211> LENGTH: 21
<212> TYPE: DNA
<213> ORGANISM: Artificial Sequence
<220> FEATURE:
<223> OTHER INFORMATION: Primer

<400> SEQUENCE: 40
aagtctccct gttctgtcct a                                      21

<210> SEQ ID NO 41
<211> LENGTH: 19
<212> TYPE: DNA
<213> ORGANISM: Artificial Sequence
<220> FEATURE:
<223> OTHER INFORMATION: Primer

<400> SEQUENCE: 41
agggtgttgc agacaaagt                                         19

<210> SEQ ID NO 42
<211> LENGTH: 20
<212> TYPE: DNA
<213> ORGANISM: Artificial Sequence
<220> FEATURE:
<223> OTHER INFORMATION: Primer

<400> SEQUENCE: 42
ttcactgctg gattgctcac                                          20

<210> SEQ ID NO 43
<211> LENGTH: 20
<212> TYPE: DNA
<213> ORGANISM: Artificial Sequence
<220> FEATURE:
<223> OTHER INFORMATION: Primer

<400> SEQUENCE: 43
ccccttggga tggatttaac                                          20

<210> SEQ ID NO 44
<211> LENGTH: 22
<212> TYPE: DNA
<213> ORGANISM: Artificial Sequence
<220> FEATURE:
<223> OTHER INFORMATION: Primer

<400> SEQUENCE: 44
aaatcccagt ccctattcct at                                       22

<210> SEQ ID NO 45
<211> LENGTH: 22
<212> TYPE: DNA
<213> ORGANISM: Artificial Sequence
<220> FEATURE:
<223> OTHER INFORMATION: Primer

<400> SEQUENCE: 45
ctaagaggaa caccacactc ac                                       22

<210> SEQ ID NO 46
<211> LENGTH: 23
<212> TYPE: DNA
<213> ORGANISM: Artificial Sequence
<220> FEATURE:
<223> OTHER INFORMATION: Primer

<400> SEQUENCE: 46
tttgcagaga atgggataga gag                                      23

<210> SEQ ID NO 47
<211> LENGTH: 24
<212> TYPE: DNA
<213> ORGANISM: Artificial Sequence
<220> FEATURE:
<223> OTHER INFORMATION: Primer

<400> SEQUENCE: 47
cacctattca ccagatttcg tagt                                     24

<210> SEQ ID NO 48
<211> LENGTH: 24
<212> TYPE: DNA
<213> ORGANISM: Artificial Sequence
<220> FEATURE:
<223> OTHER INFORMATION: Primer

<400> SEQUENCE: 48
tgaccaggaa atagagagga aatg                                     24

<210> SEQ ID NO 49
<211> LENGTH: 22
<212> TYPE: DNA
<213> ORGANISM: Artificial Sequence

```
<220> FEATURE:
<223> OTHER INFORMATION: Primer

<400> SEQUENCE: 49
cattctgcca taccaacaat gg                                             22

<210> SEQ ID NO 50
<211> LENGTH: 21
<212> TYPE: DNA
<213> ORGANISM: Artificial Sequence
<220> FEATURE:
<223> OTHER INFORMATION: Primer

<400> SEQUENCE: 50
attggaagcc gtggttatct c                                              21

<210> SEQ ID NO 51
<211> LENGTH: 21
<212> TYPE: DNA
<213> ORGANISM: Artificial Sequence
<220> FEATURE:
<223> OTHER INFORMATION: Primer

<400> SEQUENCE: 51
cttccatcac caaaccctct t                                              21

<210> SEQ ID NO 52
<211> LENGTH: 22
<212> TYPE: DNA
<213> ORGANISM: Artificial Sequence
<220> FEATURE:
<223> OTHER INFORMATION: Primer

<400> SEQUENCE: 52
ctgagtgaat cccagctaga ac                                             22

<210> SEQ ID NO 53
<211> LENGTH: 20
<212> TYPE: DNA
<213> ORGANISM: Artificial Sequence
<220> FEATURE:
<223> OTHER INFORMATION: Primer

<400> SEQUENCE: 53
gcagagaaca ggagcttgat                                                20

<210> SEQ ID NO 54
<211> LENGTH: 20
<212> TYPE: DNA
<213> ORGANISM: Artificial Sequence
<220> FEATURE:
<223> OTHER INFORMATION: Primer

<400> SEQUENCE: 54
ctccagacac tcaggcattc                                                20

<210> SEQ ID NO 55
<211> LENGTH: 21
<212> TYPE: DNA
<213> ORGANISM: Artificial Sequence
<220> FEATURE:
<223> OTHER INFORMATION: Primer

<400> SEQUENCE: 55
gtgctcacct ggtagatgaa a                                              21
```

<210> SEQ ID NO 56
<211> LENGTH: 24
<212> TYPE: DNA
<213> ORGANISM: Artificial Sequence
<220> FEATURE:
<223> OTHER INFORMATION: Primer

<400> SEQUENCE: 56
aaaatgtctt gtgaaacaaa atgc                                      24

<210> SEQ ID NO 57
<211> LENGTH: 30
<212> TYPE: DNA
<213> ORGANISM: Artificial Sequence
<220> FEATURE:
<223> OTHER INFORMATION: Primer

<400> SEQUENCE: 57
ttttacaaaa gtaagattca ctttcataat                                30

<210> SEQ ID NO 58
<211> LENGTH: 27
<212> TYPE: DNA
<213> ORGANISM: Artificial Sequence
<220> FEATURE:
<223> OTHER INFORMATION: Primer

<400> SEQUENCE: 58
agggtttcag acaaaatcaa aagaag                                    27

<210> SEQ ID NO 59
<211> LENGTH: 30
<212> TYPE: DNA
<213> ORGANISM: Artificial Sequence
<220> FEATURE:
<223> OTHER INFORMATION: Primer

<400> SEQUENCE: 59
ctaatagttt tggcatcaaa attctttaat                                30

<210> SEQ ID NO 60
<211> LENGTH: 25
<212> TYPE: DNA
<213> ORGANISM: Artificial Sequence
<220> FEATURE:
<223> OTHER INFORMATION: Primer

<400> SEQUENCE: 60
ctttatggtt tgtggaaaac aaatg                                     25

<210> SEQ ID NO 61
<211> LENGTH: 26
<212> TYPE: DNA
<213> ORGANISM: Artificial Sequence
<220> FEATURE:
<223> OTHER INFORMATION: Primer

<400> SEQUENCE: 61
gtctgcctac tagtgatata aaatgg                                    26

<210> SEQ ID NO 62
<211> LENGTH: 21
<212> TYPE: DNA
<213> ORGANISM: Artificial Sequence
<220> FEATURE:
<223> OTHER INFORMATION: Primer

<400> SEQUENCE: 62
ctggaatgtg aagcgttata g								21

<210> SEQ ID NO 63
<211> LENGTH: 26
<212> TYPE: DNA
<213> ORGANISM: Artificial Sequence
<220> FEATURE:
<223> OTHER INFORMATION: Primer

<400> SEQUENCE: 63
caaaatctaa tccacattca aatttt								26

<210> SEQ ID NO 64
<211> LENGTH: 20
<212> TYPE: DNA
<213> ORGANISM: Artificial Sequence
<220> FEATURE:
<223> OTHER INFORMATION: Primer

<400> SEQUENCE: 64
tgtgggattg taggcatgag								20

<210> SEQ ID NO 65
<211> LENGTH: 22
<212> TYPE: DNA
<213> ORGANISM: Artificial Sequence
<220> FEATURE:
<223> OTHER INFORMATION: Primer

<400> SEQUENCE: 65
gctggcagac ttactcctta at								22

<210> SEQ ID NO 66
<211> LENGTH: 22
<212> TYPE: DNA
<213> ORGANISM: Artificial Sequence
<220> FEATURE:
<223> OTHER INFORMATION: Primer

<400> SEQUENCE: 66
aagtctgcca gcattatgaa ag								22

<210> SEQ ID NO 67
<211> LENGTH: 21
<212> TYPE: DNA
<213> ORGANISM: Artificial Sequence
<220> FEATURE:
<223> OTHER INFORMATION: Primer

<400> SEQUENCE: 67
ccacataacc aaccagttaa g								21

<210> SEQ ID NO 68
<211> LENGTH: 24
<212> TYPE: DNA
<213> ORGANISM: Artificial Sequence
<220> FEATURE:
<223> OTHER INFORMATION: Primer

<400> SEQUENCE: 68
gttcagatgt taaaaagttg aaag								24

<210> SEQ ID NO 69

<211> LENGTH: 24
<212> TYPE: DNA
<213> ORGANISM: Artificial Sequence
<220> FEATURE:
<223> OTHER INFORMATION: Primer

<400> SEQUENCE: 69
tggtctgcct actagtgata taaa                                          24

<210> SEQ ID NO 70
<211> LENGTH: 22
<212> TYPE: DNA
<213> ORGANISM: Artificial Sequence
<220> FEATURE:
<223> OTHER INFORMATION: Primer

<400> SEQUENCE: 70
ggaagtggaa tgggtaactc tt                                            22

<210> SEQ ID NO 71
<211> LENGTH: 21
<212> TYPE: DNA
<213> ORGANISM: Artificial Sequence
<220> FEATURE:
<223> OTHER INFORMATION: Primer

<400> SEQUENCE: 71
ccacatacgc ctcacataca t                                             21

<210> SEQ ID NO 72
<211> LENGTH: 21
<212> TYPE: DNA
<213> ORGANISM: Artificial Sequence
<220> FEATURE:
<223> OTHER INFORMATION: Primer

<400> SEQUENCE: 72
ccaaaggttg gatttgatgc c                                             21

<210> SEQ ID NO 73
<211> LENGTH: 26
<212> TYPE: DNA
<213> ORGANISM: Artificial Sequence
<220> FEATURE:
<223> OTHER INFORMATION: Primer

<400> SEQUENCE: 73
gaatagctca gttgttcttt gatacg                                        26

<210> SEQ ID NO 74
<211> LENGTH: 22
<212> TYPE: DNA
<213> ORGANISM: Artificial Sequence
<220> FEATURE:
<223> OTHER INFORMATION: Primer

<400> SEQUENCE: 74
ccgacgaaca ctttctcgta tc                                            22

<210> SEQ ID NO 75
<211> LENGTH: 24
<212> TYPE: DNA
<213> ORGANISM: Artificial Sequence
<220> FEATURE:
<223> OTHER INFORMATION: Primer

<400> SEQUENCE: 75
gggttccagg aaattacttt gttt                                          24

<210> SEQ ID NO 76
<211> LENGTH: 21
<212> TYPE: DNA
<213> ORGANISM: Artificial Sequence
<220> FEATURE:
<223> OTHER INFORMATION: Primer

<400> SEQUENCE: 76
aagtctccct gttctgtcct a                                             21

<210> SEQ ID NO 77
<211> LENGTH: 19
<212> TYPE: DNA
<213> ORGANISM: Artificial Sequence
<220> FEATURE:
<223> OTHER INFORMATION: Primer

<400> SEQUENCE: 77
agggtgttgc agacaaagt                                                19

<210> SEQ ID NO 78
<211> LENGTH: 20
<212> TYPE: DNA
<213> ORGANISM: Artificial Sequence
<220> FEATURE:
<223> OTHER INFORMATION: Primer

<400> SEQUENCE: 78
ttcactgctg gattgctcac                                               20

<210> SEQ ID NO 79
<211> LENGTH: 20
<212> TYPE: DNA
<213> ORGANISM: Artificial Sequence
<220> FEATURE:
<223> OTHER INFORMATION: Primer

<400> SEQUENCE: 79
ccccttggga tggatttaac                                               20

<210> SEQ ID NO 80
<211> LENGTH: 22
<212> TYPE: DNA
<213> ORGANISM: Artificial Sequence
<220> FEATURE:
<223> OTHER INFORMATION: Primer

<400> SEQUENCE: 80
ggaggaactt gatatcccaa cc                                            22

<210> SEQ ID NO 81
<211> LENGTH: 22
<212> TYPE: DNA
<213> ORGANISM: Artificial Sequence
<220> FEATURE:
<223> OTHER INFORMATION: Primer

<400> SEQUENCE: 81
atactggaca acccacatca tt                                            22

<210> SEQ ID NO 82
<211> LENGTH: 19
<212> TYPE: DNA

```
<213> ORGANISM: Artificial Sequence
<220> FEATURE:
<223> OTHER INFORMATION: Primer

<400> SEQUENCE: 82
gagcaatgcg ggttctttg                                                19

<210> SEQ ID NO 83
<211> LENGTH: 26
<212> TYPE: DNA
<213> ORGANISM: Artificial Sequence
<220> FEATURE:
<223> OTHER INFORMATION: Primer

<400> SEQUENCE: 83
gctagactag acttgtgtaa tgtttg                                        26

<210> SEQ ID NO 84
<211> LENGTH: 20
<212> TYPE: DNA
<213> ORGANISM: Artificial Sequence
<220> FEATURE:
<223> OTHER INFORMATION: Primer

<400> SEQUENCE: 84
ggttggccaa tctactccca                                               20

<210> SEQ ID NO 85
<211> LENGTH: 20
<212> TYPE: DNA
<213> ORGANISM: Artificial Sequence
<220> FEATURE:
<223> OTHER INFORMATION: Primer

<400> SEQUENCE: 85
aaggtgccct tgaggttgtc                                               20

<210> SEQ ID NO 86
<211> LENGTH: 20
<212> TYPE: DNA
<213> ORGANISM: Artificial Sequence
<220> FEATURE:
<223> OTHER INFORMATION: Primer

<400> SEQUENCE: 86
tcatgcctct ttgcaccatt                                               20

<210> SEQ ID NO 87
<211> LENGTH: 21
<212> TYPE: DNA
<213> ORGANISM: Artificial Sequence
<220> FEATURE:
<223> OTHER INFORMATION: Primer

<400> SEQUENCE: 87
aatccagcct tatcccaacc a                                             21

<210> SEQ ID NO 88
<211> LENGTH: 18
<212> TYPE: DNA
<213> ORGANISM: Artificial Sequence
<220> FEATURE:
<223> OTHER INFORMATION: Primer

<400> SEQUENCE: 88
ggagtcgaag ctgactca                                                 18
```

```
<210> SEQ ID NO 89
<211> LENGTH: 20
<212> TYPE: DNA
<213> ORGANISM: Artificial Sequence
<220> FEATURE:
<223> OTHER INFORMATION: Primer

<400> SEQUENCE: 89
cagttgcaac gaagccaatc                                                    20

<210> SEQ ID NO 90
<211> LENGTH: 21
<212> TYPE: DNA
<213> ORGANISM: Artificial Sequence
<220> FEATURE:
<223> OTHER INFORMATION: Primer

<400> SEQUENCE: 90
cttctctgca cagctcctaa g                                                  21

<210> SEQ ID NO 91
<211> LENGTH: 20
<212> TYPE: DNA
<213> ORGANISM: Artificial Sequence
<220> FEATURE:
<223> OTHER INFORMATION: Primer

<400> SEQUENCE: 91
gctgcccact cagactttat                                                    20

<210> SEQ ID NO 92
<211> LENGTH: 20
<212> TYPE: DNA
<213> ORGANISM: Artificial Sequence
<220> FEATURE:
<223> OTHER INFORMATION: Primer

<400> SEQUENCE: 92
gacgccaagt ttgaaggaac                                                    20

<210> SEQ ID NO 93
<211> LENGTH: 23
<212> TYPE: DNA
<213> ORGANISM: Artificial Sequence
<220> FEATURE:
<223> OTHER INFORMATION: Primer

<400> SEQUENCE: 93
ctactgctag aaacagccta ctc                                                23

<210> SEQ ID NO 94
<211> LENGTH: 20
<212> TYPE: DNA
<213> ORGANISM: Artificial Sequence
<220> FEATURE:
<223> OTHER INFORMATION: Primer

<400> SEQUENCE: 94
tcgcattatg atcctcgttg                                                    20

<210> SEQ ID NO 95
<211> LENGTH: 20
<212> TYPE: DNA
<213> ORGANISM: Artificial Sequence
<220> FEATURE:
```

<223> OTHER INFORMATION: Primer

<400> SEQUENCE: 95
ggacacaaag cagtccacag                                                      20

<210> SEQ ID NO 96
<211> LENGTH: 24
<212> TYPE: DNA
<213> ORGANISM: Artificial Sequence
<220> FEATURE:
<223> OTHER INFORMATION: Primer

<400> SEQUENCE: 96
aggaaaggca tactggaggg acat                                                 24

<210> SEQ ID NO 97
<211> LENGTH: 24
<212> TYPE: DNA
<213> ORGANISM: Artificial Sequence
<220> FEATURE:
<223> OTHER INFORMATION: Primer

<400> SEQUENCE: 97
ttagggatgg caccacactc ttga                                                 24

<210> SEQ ID NO 98
<211> LENGTH: 24
<212> TYPE: DNA
<213> ORGANISM: Artificial Sequence
<220> FEATURE:
<223> OTHER INFORMATION: Primer

<400> SEQUENCE: 98
tcccagagaa gcatcctcca tgtt                                                 24

<210> SEQ ID NO 99
<211> LENGTH: 24
<212> TYPE: DNA
<213> ORGANISM: Artificial Sequence
<220> FEATURE:
<223> OTHER INFORMATION: Primer

<400> SEQUENCE: 99
caccacactg cctcaaatgt tgct                                                 24

<210> SEQ ID NO 100
<211> LENGTH: 24
<212> TYPE: DNA
<213> ORGANISM: Artificial Sequence
<220> FEATURE:
<223> OTHER INFORMATION: Primer

<400> SEQUENCE: 100
atgggcaaat ccagaagagt ccag                                                 24

<210> SEQ ID NO 101
<211> LENGTH: 26
<212> TYPE: DNA
<213> ORGANISM: Artificial Sequence
<220> FEATURE:
<223> OTHER INFORMATION: Primer

<400> SEQUENCE: 101
ccattcactt ccttggaaag gtagcc                                               26

```
<210> SEQ ID NO 102
<211> LENGTH: 24
<212> TYPE: DNA
<213> ORGANISM: Artificial Sequence
<220> FEATURE:
<223> OTHER INFORMATION: Primer

<400> SEQUENCE: 102
aatagcgtgc agttctgggt agca                                          24

<210> SEQ ID NO 103
<211> LENGTH: 24
<212> TYPE: DNA
<213> ORGANISM: Artificial Sequence
<220> FEATURE:
<223> OTHER INFORMATION: Primer

<400> SEQUENCE: 103
ttcacatcct gggaggaaca gcat                                          24

<210> SEQ ID NO 104
<211> LENGTH: 24
<212> TYPE: DNA
<213> ORGANISM: Artificial Sequence
<220> FEATURE:
<223> OTHER INFORMATION: Primer

<400> SEQUENCE: 104
tgaatgccag ggtgagacct ttga                                          24

<210> SEQ ID NO 105
<211> LENGTH: 24
<212> TYPE: DNA
<213> ORGANISM: Artificial Sequence
<220> FEATURE:
<223> OTHER INFORMATION: Primer

<400> SEQUENCE: 105
tgttcattat cccacgccag gact                                          24

<210> SEQ ID NO 106
<211> LENGTH: 24
<212> TYPE: DNA
<213> ORGANISM: Artificial Sequence
<220> FEATURE:
<223> OTHER INFORMATION: Primer

<400> SEQUENCE: 106
accaaaggaa agccagccag tcta                                          24

<210> SEQ ID NO 107
<211> LENGTH: 24
<212> TYPE: DNA
<213> ORGANISM: Artificial Sequence
<220> FEATURE:
<223> OTHER INFORMATION: Primer

<400> SEQUENCE: 107
actccacagc tcccaagcat acaa                                          24

<210> SEQ ID NO 108
<211> LENGTH: 21
<212> TYPE: DNA
<213> ORGANISM: Artificial Sequence
<220> FEATURE:
<223> OTHER INFORMATION: Primer
```

<400> SEQUENCE: 108
tgggctgcag aaagaaatag a                                              21

<210> SEQ ID NO 109
<211> LENGTH: 20
<212> TYPE: DNA
<213> ORGANISM: Artificial Sequence
<220> FEATURE:
<223> OTHER INFORMATION: Primer

<400> SEQUENCE: 109
tcccaaagtg ctgggattac                                                20

<210> SEQ ID NO 110
<211> LENGTH: 27
<212> TYPE: DNA
<213> ORGANISM: Artificial Sequence
<220> FEATURE:
<223> OTHER INFORMATION: Primer

<400> SEQUENCE: 110
gtgcataaaa ctttagagta cagctca                                        27

<210> SEQ ID NO 111
<211> LENGTH: 24
<212> TYPE: DNA
<213> ORGANISM: Artificial Sequence
<220> FEATURE:
<223> OTHER INFORMATION: Primer

<400> SEQUENCE: 111
tggttactat tcgagaggac actg                                           24

<210> SEQ ID NO 112
<211> LENGTH: 21
<212> TYPE: DNA
<213> ORGANISM: Artificial Sequence
<220> FEATURE:
<223> OTHER INFORMATION: Primer

<400> SEQUENCE: 112
tgacagtcaa ggcagtagca a                                              21

<210> SEQ ID NO 113
<211> LENGTH: 20
<212> TYPE: DNA
<213> ORGANISM: Artificial Sequence
<220> FEATURE:
<223> OTHER INFORMATION: Primer

<400> SEQUENCE: 113
taacccttgt tggtgagcag                                                20

<210> SEQ ID NO 114
<211> LENGTH: 21
<212> TYPE: DNA
<213> ORGANISM: Artificial Sequence
<220> FEATURE:
<223> OTHER INFORMATION: Primer

<400> SEQUENCE: 114
ctggtccttg acttcctctc a                                              21

<210> SEQ ID NO 115
<211> LENGTH: 21

```
<212> TYPE: DNA
<213> ORGANISM: Artificial Sequence
<220> FEATURE:
<223> OTHER INFORMATION: Primer

<400> SEQUENCE: 115
tggctaagaa gacctggttg a                                            21

<210> SEQ ID NO 116
<211> LENGTH: 20
<212> TYPE: DNA
<213> ORGANISM: Artificial Sequence
<220> FEATURE:
<223> OTHER INFORMATION: Primer

<400> SEQUENCE: 116
tcctgcacag agtccgtaga                                              20

<210> SEQ ID NO 117
<211> LENGTH: 20
<212> TYPE: DNA
<213> ORGANISM: Artificial Sequence
<220> FEATURE:
<223> OTHER INFORMATION: Primer

<400> SEQUENCE: 117
ggggttcttc tgacttccaa                                              20

<210> SEQ ID NO 118
<211> LENGTH: 24
<212> TYPE: DNA
<213> ORGANISM: Artificial Sequence
<220> FEATURE:
<223> OTHER INFORMATION: Primer

<400> SEQUENCE: 118
cacagaagtg ttgtagggta gagg                                         24

<210> SEQ ID NO 119
<211> LENGTH: 20
<212> TYPE: DNA
<213> ORGANISM: Artificial Sequence
<220> FEATURE:
<223> OTHER INFORMATION: Primer

<400> SEQUENCE: 119
agcaggcagg cattgtttat                                              20

<210> SEQ ID NO 120
<211> LENGTH: 20
<212> TYPE: DNA
<213> ORGANISM: Artificial Sequence
<220> FEATURE:
<223> OTHER INFORMATION: Primer

<400> SEQUENCE: 120
ggagtgcctt tgcatcatct                                              20

<210> SEQ ID NO 121
<211> LENGTH: 20
<212> TYPE: DNA
<213> ORGANISM: Artificial Sequence
<220> FEATURE:
<223> OTHER INFORMATION: Primer

<400> SEQUENCE: 121
```
gcggtgtttg gttttctgtt                                                  20

<210> SEQ ID NO 122
<211> LENGTH: 23
<212> TYPE: DNA
<213> ORGANISM: Artificial Sequence
<220> FEATURE:
<223> OTHER INFORMATION: Primer

<400> SEQUENCE: 122
tcttggtaga aatggataac ctg                                              23

<210> SEQ ID NO 123
<211> LENGTH: 20
<212> TYPE: DNA
<213> ORGANISM: Artificial Sequence
<220> FEATURE:
<223> OTHER INFORMATION: Primer

<400> SEQUENCE: 123
agcaacaggg ttcaagaagg                                                  20

<210> SEQ ID NO 124
<211> LENGTH: 20
<212> TYPE: DNA
<213> ORGANISM: Artificial Sequence
<220> FEATURE:
<223> OTHER INFORMATION: Primer

<400> SEQUENCE: 124
agctcttcag gtggcaggta                                                  20

<210> SEQ ID NO 125
<211> LENGTH: 20
<212> TYPE: DNA
<213> ORGANISM: Artificial Sequence
<220> FEATURE:
<223> OTHER INFORMATION: Primer

<400> SEQUENCE: 125
ccttgaagca gccttgtgat                                                  20

<210> SEQ ID NO 126
<211> LENGTH: 21
<212> TYPE: DNA
<213> ORGANISM: Artificial Sequence
<220> FEATURE:
<223> OTHER INFORMATION: Primer

<400> SEQUENCE: 126
cctcctgaat taatcggcat t                                                21

<210> SEQ ID NO 127
<211> LENGTH: 27
<212> TYPE: DNA
<213> ORGANISM: Artificial Sequence
<220> FEATURE:
<223> OTHER INFORMATION: Primer

<400> SEQUENCE: 127
cacattaaaa attgaaggat tctatga                                          27

<210> SEQ ID NO 128
<211> LENGTH: 20
<212> TYPE: DNA
<213> ORGANISM: Artificial Sequence

```
<220> FEATURE:
<223> OTHER INFORMATION: Primer

<400> SEQUENCE: 128
tccccatgaa cttttttgctt                                              20

<210> SEQ ID NO 129
<211> LENGTH: 20
<212> TYPE: DNA
<213> ORGANISM: Artificial Sequence
<220> FEATURE:
<223> OTHER INFORMATION: Primer

<400> SEQUENCE: 129
tgtccagaat ggtgttgctc                                               20

<210> SEQ ID NO 130
<211> LENGTH: 20
<212> TYPE: DNA
<213> ORGANISM: Artificial Sequence
<220> FEATURE:
<223> OTHER INFORMATION: Primer

<400> SEQUENCE: 130
cgtgttgctt aacgatgagg                                               20

<210> SEQ ID NO 131
<211> LENGTH: 22
<212> TYPE: DNA
<213> ORGANISM: Artificial Sequence
<220> FEATURE:
<223> OTHER INFORMATION: Primer

<400> SEQUENCE: 131
tgtacaggtt tgtagccaag ga                                            22

<210> SEQ ID NO 132
<211> LENGTH: 20
<212> TYPE: DNA
<213> ORGANISM: Artificial Sequence
<220> FEATURE:
<223> OTHER INFORMATION: Primer

<400> SEQUENCE: 132
tgctcatccc ccagtaaaac                                               20

<210> SEQ ID NO 133
<211> LENGTH: 20
<212> TYPE: DNA
<213> ORGANISM: Artificial Sequence
<220> FEATURE:
<223> OTHER INFORMATION: Primer

<400> SEQUENCE: 133
ggaaatccct catttcatgc                                               20

<210> SEQ ID NO 134
<211> LENGTH: 20
<212> TYPE: DNA
<213> ORGANISM: Artificial Sequence
<220> FEATURE:
<223> OTHER INFORMATION: Primer

<400> SEQUENCE: 134
tccaagcatg atgagggatt                                               20
```

```
<210> SEQ ID NO 135
<211> LENGTH: 21
<212> TYPE: DNA
<213> ORGANISM: Artificial Sequence
<220> FEATURE:
<223> OTHER INFORMATION: Primer

<400> SEQUENCE: 135
tttttatgca tgctggcttt t                                         21

<210> SEQ ID NO 136
<211> LENGTH: 21
<212> TYPE: DNA
<213> ORGANISM: Artificial Sequence
<220> FEATURE:
<223> OTHER INFORMATION: Primer

<400> SEQUENCE: 136
gggattattt gaggcaatca g                                         21

<210> SEQ ID NO 137
<211> LENGTH: 24
<212> TYPE: DNA
<213> ORGANISM: Artificial Sequence
<220> FEATURE:
<223> OTHER INFORMATION: Primer

<400> SEQUENCE: 137
aacaataacc aataaacacg gaca                                      24

<210> SEQ ID NO 138
<211> LENGTH: 20
<212> TYPE: DNA
<213> ORGANISM: Artificial Sequence
<220> FEATURE:
<223> OTHER INFORMATION: Primer

<400> SEQUENCE: 138
cccctaggca catgaaacac                                           20

<210> SEQ ID NO 139
<211> LENGTH: 20
<212> TYPE: DNA
<213> ORGANISM: Artificial Sequence
<220> FEATURE:
<223> OTHER INFORMATION: Primer

<400> SEQUENCE: 139
tttgggtgtg gggataactc                                           20

<210> SEQ ID NO 140
<211> LENGTH: 20
<212> TYPE: DNA
<213> ORGANISM: Artificial Sequence
<220> FEATURE:
<223> OTHER INFORMATION: Primer

<400> SEQUENCE: 140
agtgcagttg tgtggcatgt                                           20

<210> SEQ ID NO 141
<211> LENGTH: 20
<212> TYPE: DNA
<213> ORGANISM: Artificial Sequence
<220> FEATURE:
<223> OTHER INFORMATION: Primer
```

-continued

```
<400> SEQUENCE: 141
ggggtcctga cttgatgtgt                                           20

<210> SEQ ID NO 142
<211> LENGTH: 20
<212> TYPE: DNA
<213> ORGANISM: Artificial Sequence
<220> FEATURE:
<223> OTHER INFORMATION: Primer

<400> SEQUENCE: 142
cagcatgact ggcatttgat                                           20

<210> SEQ ID NO 143
<211> LENGTH: 23
<212> TYPE: DNA
<213> ORGANISM: Artificial Sequence
<220> FEATURE:
<223> OTHER INFORMATION: Primer

<400> SEQUENCE: 143
tcaccacact attttccatt gtg                                       23

<210> SEQ ID NO 144
<211> LENGTH: 20
<212> TYPE: DNA
<213> ORGANISM: Artificial Sequence
<220> FEATURE:
<223> OTHER INFORMATION: Primer

<400> SEQUENCE: 144
tgcatcctgt gagaaagcag                                           20

<210> SEQ ID NO 145
<211> LENGTH: 22
<212> TYPE: DNA
<213> ORGANISM: Artificial Sequence
<220> FEATURE:
<223> OTHER INFORMATION: Primer

<400> SEQUENCE: 145
aaaaagaaaa gccatcgtaa gc                                        22

<210> SEQ ID NO 146
<211> LENGTH: 20
<212> TYPE: DNA
<213> ORGANISM: Artificial Sequence
<220> FEATURE:
<223> OTHER INFORMATION: Primer

<400> SEQUENCE: 146
gcaatttcct ggccatattc                                           20

<210> SEQ ID NO 147
<211> LENGTH: 22
<212> TYPE: DNA
<213> ORGANISM: Artificial Sequence
<220> FEATURE:
<223> OTHER INFORMATION: Primer

<400> SEQUENCE: 147
gacatttgac ttgagccact ga                                        22

<210> SEQ ID NO 148
```

```
<211> LENGTH: 20
<212> TYPE: DNA
<213> ORGANISM: Artificial Sequence
<220> FEATURE:
<223> OTHER INFORMATION: Primer

<400> SEQUENCE: 148
tgcccccaaa agtctcatta                                               20

<210> SEQ ID NO 149
<211> LENGTH: 20
<212> TYPE: DNA
<213> ORGANISM: Artificial Sequence
<220> FEATURE:
<223> OTHER INFORMATION: Primer

<400> SEQUENCE: 149
ttgaggcatg tgctcatttt                                               20

<210> SEQ ID NO 150
<211> LENGTH: 20
<212> TYPE: DNA
<213> ORGANISM: Artificial Sequence
<220> FEATURE:
<223> OTHER INFORMATION: Primer

<400> SEQUENCE: 150
gcacataaaa ggccagcact                                               20

<210> SEQ ID NO 151
<211> LENGTH: 20
<212> TYPE: DNA
<213> ORGANISM: Artificial Sequence
<220> FEATURE:
<223> OTHER INFORMATION: Primer

<400> SEQUENCE: 151
tgggctcttg gtgatcattt                                               20

<210> SEQ ID NO 152
<211> LENGTH: 20
<212> TYPE: DNA
<213> ORGANISM: Artificial Sequence
<220> FEATURE:
<223> OTHER INFORMATION: Primer

<400> SEQUENCE: 152
agtcctagcc agagcgtcaa                                               20

<210> SEQ ID NO 153
<211> LENGTH: 23
<212> TYPE: DNA
<213> ORGANISM: Artificial Sequence
<220> FEATURE:
<223> OTHER INFORMATION: Primer

<400> SEQUENCE: 153
tttcgctgaa attgtttatc aga                                           23

<210> SEQ ID NO 154
<211> LENGTH: 20
<212> TYPE: DNA
<213> ORGANISM: Artificial Sequence
<220> FEATURE:
<223> OTHER INFORMATION: Primer

<400> SEQUENCE: 154
```
tgggttggtg acatcactgt 20

<210> SEQ ID NO 155
<211> LENGTH: 20
<212> TYPE: DNA
<213> ORGANISM: Artificial Sequence
<220> FEATURE:
<223> OTHER INFORMATION: Primer

<400> SEQUENCE: 155
ctccaaggat tcccttccat 20

<210> SEQ ID NO 156
<211> LENGTH: 20
<212> TYPE: DNA
<213> ORGANISM: Artificial Sequence
<220> FEATURE:
<223> OTHER INFORMATION: Primer

<400> SEQUENCE: 156
tacagtggag atggcagcag 20

<210> SEQ ID NO 157
<211> LENGTH: 20
<212> TYPE: DNA
<213> ORGANISM: Artificial Sequence
<220> FEATURE:
<223> OTHER INFORMATION: Primer

<400> SEQUENCE: 157
agggccagag tagggtgaat 20

<210> SEQ ID NO 158
<211> LENGTH: 20
<212> TYPE: DNA
<213> ORGANISM: Artificial Sequence
<220> FEATURE:
<223> OTHER INFORMATION: Primer

<400> SEQUENCE: 158
ctttgcagaa ccactggatg 20

<210> SEQ ID NO 159
<211> LENGTH: 20
<212> TYPE: DNA
<213> ORGANISM: Artificial Sequence
<220> FEATURE:
<223> OTHER INFORMATION: Primer

<400> SEQUENCE: 159
gagggctctt ctgcactgag 20

<210> SEQ ID NO 160
<211> LENGTH: 20
<212> TYPE: DNA
<213> ORGANISM: Artificial Sequence
<220> FEATURE:
<223> OTHER INFORMATION: Primer

<400> SEQUENCE: 160
gcatgccata ggacatttga 20

<210> SEQ ID NO 161
<211> LENGTH: 23
<212> TYPE: DNA

```
<213> ORGANISM: Artificial Sequence
<220> FEATURE:
<223> OTHER INFORMATION: Primer

<400> SEQUENCE: 161
tttcatcttg aaggaacaca caa                                          23

<210> SEQ ID NO 162
<211> LENGTH: 20
<212> TYPE: DNA
<213> ORGANISM: Artificial Sequence
<220> FEATURE:
<223> OTHER INFORMATION: Primer

<400> SEQUENCE: 162
ccagaaggag ttgggagatg                                              20

<210> SEQ ID NO 163
<211> LENGTH: 20
<212> TYPE: DNA
<213> ORGANISM: Artificial Sequence
<220> FEATURE:
<223> OTHER INFORMATION: Primer

<400> SEQUENCE: 163
cgctcactcg gcttttatct                                              20

<210> SEQ ID NO 164
<211> LENGTH: 20
<212> TYPE: DNA
<213> ORGANISM: Artificial Sequence
<220> FEATURE:
<223> OTHER INFORMATION: Primer

<400> SEQUENCE: 164
gccaccacag ttggctttat                                              20

<210> SEQ ID NO 165
<211> LENGTH: 20
<212> TYPE: DNA
<213> ORGANISM: Artificial Sequence
<220> FEATURE:
<223> OTHER INFORMATION: Primer

<400> SEQUENCE: 165 tcattttgc cctctccatc                                               20

<210> SEQ ID NO 166
<211> LENGTH: 20
<212> TYPE: DNA
<213> ORGANISM: Artificial Sequence
<220> FEATURE:
<223> OTHER INFORMATION: Primer

<400> SEQUENCE: 166
tgactctctc catggctgtg                                              20

<210> SEQ ID NO 167
<211> LENGTH: 20
<212> TYPE: DNA
<213> ORGANISM: Artificial Sequence
<220> FEATURE:
<223> OTHER INFORMATION: Primer

<400> SEQUENCE: 167
aagagcttgg tgggcataga                                              20
```

<210> SEQ ID NO 168
<211> LENGTH: 22
<212> TYPE: DNA
<213> ORGANISM: Artificial Sequence
<220> FEATURE:
<223> OTHER INFORMATION: Primer

<400> SEQUENCE: 168
acatgacctc accaaatgaa ct                                              22

<210> SEQ ID NO 169
<211> LENGTH: 24
<212> TYPE: DNA
<213> ORGANISM: Artificial Sequence
<220> FEATURE:
<223> OTHER INFORMATION: Primer

<400> SEQUENCE: 169
actgcattct tcagtaggct aatc                                            24

<210> SEQ ID NO 170
<211> LENGTH: 19
<212> TYPE: DNA
<213> ORGANISM: Artificial Sequence
<220> FEATURE:
<223> OTHER INFORMATION: Primer

<400> SEQUENCE: 170
ctgctgtccc tgtgtcttc                                                  19

<210> SEQ ID NO 171
<211> LENGTH: 20
<212> TYPE: DNA
<213> ORGANISM: Artificial Sequence
<220> FEATURE:
<223> OTHER INFORMATION: Primer

<400> SEQUENCE: 171
ctggaagttc ccagcttctc                                                 20

<210> SEQ ID NO 172
<211> LENGTH: 22
<212> TYPE: DNA
<213> ORGANISM: Artificial Sequence
<220> FEATURE:
<223> OTHER INFORMATION: Primer

<400> SEQUENCE: 172
gtcctctgga ttgtctcatt gg                                              22

<210> SEQ ID NO 173
<211> LENGTH: 20
<212> TYPE: DNA
<213> ORGANISM: Artificial Sequence
<220> FEATURE:
<223> OTHER INFORMATION: Primer

<400> SEQUENCE: 173
catggctgtc gaacagatga                                                 20

<210> SEQ ID NO 174
<211> LENGTH: 20
<212> TYPE: DNA
<213> ORGANISM: Artificial Sequence
<220> FEATURE:

<223> OTHER INFORMATION: Primer

<400> SEQUENCE: 174
ggacgctgta cccttgtaaa                                        20

<210> SEQ ID NO 175
<211> LENGTH: 20
<212> TYPE: DNA
<213> ORGANISM: Artificial Sequence
<220> FEATURE:
<223> OTHER INFORMATION: Primer

<400> SEQUENCE: 175
ccatcctctc caaactgtcc                                        20

<210> SEQ ID NO 176
<211> LENGTH: 20
<212> TYPE: DNA
<213> ORGANISM: Artificial Sequence
<220> FEATURE:
<223> OTHER INFORMATION: Primer

<400> SEQUENCE: 176
tttcatgcct tcgagagtgg                                        20

<210> SEQ ID NO 177
<211> LENGTH: 20
<212> TYPE: DNA
<213> ORGANISM: Artificial Sequence
<220> FEATURE:
<223> OTHER INFORMATION: Primer

<400> SEQUENCE: 177
cactggcaac agatccttga                                        20

<210> SEQ ID NO 178
<211> LENGTH: 20
<212> TYPE: DNA
<213> ORGANISM: Artificial Sequence
<220> FEATURE:
<223> OTHER INFORMATION: Primer

<400> SEQUENCE: 178
cacgagctga tccttcaaca                                        20

<210> SEQ ID NO 179
<211> LENGTH: 22
<212> TYPE: DNA
<213> ORGANISM: Artificial Sequence
<220> FEATURE:
<223> OTHER INFORMATION: Primer

<400> SEQUENCE: 179
caggtgagac ttcttgccta tt                                     22

<210> SEQ ID NO 180
<211> LENGTH: 20
<212> TYPE: DNA
<213> ORGANISM: Artificial Sequence
<220> FEATURE:
<223> OTHER INFORMATION: Primer

<400> SEQUENCE: 180
atatgggcat ggaacttggt                                        20

```
<210> SEQ ID NO 181
<211> LENGTH: 25
<212> TYPE: DNA
<213> ORGANISM: Artificial Sequence
<220> FEATURE:
<223> OTHER INFORMATION: Primer

<400> SEQUENCE: 181
tcctatgtct agctggttaa ttcat                                         25

<210> SEQ ID NO 182
<211> LENGTH: 22
<212> TYPE: DNA
<213> ORGANISM: Artificial Sequence
<220> FEATURE:
<223> OTHER INFORMATION: Primer

<400> SEQUENCE: 182
aaattgctgt ggaaactgag tg                                            22

<210> SEQ ID NO 183
<211> LENGTH: 21
<212> TYPE: DNA
<213> ORGANISM: Artificial Sequence
<220> FEATURE:
<223> OTHER INFORMATION: Primer

<400> SEQUENCE: 183
gggtctggtc ctcaacaatt a                                             21

<210> SEQ ID NO 184
<211> LENGTH: 21
<212> TYPE: DNA
<213> ORGANISM: Artificial Sequence
<220> FEATURE:
<223> OTHER INFORMATION: Primer

<400> SEQUENCE: 184
ggtggtgatt ggtgatgaag a                                             21

<210> SEQ ID NO 185
<211> LENGTH: 23
<212> TYPE: DNA
<213> ORGANISM: Artificial Sequence
<220> FEATURE:
<223> OTHER INFORMATION: Primer

<400> SEQUENCE: 185
ctgcctccaa acctagtcta ttc                                           23

<210> SEQ ID NO 186
<211> LENGTH: 25
<212> TYPE: DNA
<213> ORGANISM: Artificial Sequence
<220> FEATURE:
<223> OTHER INFORMATION: Primer

<400> SEQUENCE: 186
cttccgaatt atgaacctgg attac                                         25

<210> SEQ ID NO 187
<211> LENGTH: 20
<212> TYPE: DNA
<213> ORGANISM: Artificial Sequence
<220> FEATURE:
<223> OTHER INFORMATION: Primer
```

<400> SEQUENCE: 187
tgttcctcgg ctctctctaa                                               20

<210> SEQ ID NO 188
<211> LENGTH: 18
<212> TYPE: DNA
<213> ORGANISM: Artificial Sequence
<220> FEATURE:
<223> OTHER INFORMATION: Primer

<400> SEQUENCE: 188
aatgtgggaa acgcaggt                                                 18

<210> SEQ ID NO 189
<211> LENGTH: 22
<212> TYPE: DNA
<213> ORGANISM: Artificial Sequence
<220> FEATURE:
<223> OTHER INFORMATION: Primer

<400> SEQUENCE: 189
gttctgtttc caccctgatg ta                                            22

<210> SEQ ID NO 190
<211> LENGTH: 21
<212> TYPE: DNA
<213> ORGANISM: Artificial Sequence
<220> FEATURE:
<223> OTHER INFORMATION: Primer

<400> SEQUENCE: 190
tctaggacca cctcagtgaa t                                             21

<210> SEQ ID NO 191
<211> LENGTH: 23
<212> TYPE: DNA
<213> ORGANISM: Artificial Sequence
<220> FEATURE:
<223> OTHER INFORMATION: Primer

<400> SEQUENCE: 191
gaagaaggaa tgccaacaga aag                                           23

<210> SEQ ID NO 192
<211> LENGTH: 28
<212> TYPE: DNA
<213> ORGANISM: Artificial Sequence
<220> FEATURE:
<223> OTHER INFORMATION: Primer

<400> SEQUENCE: 192
acagataaat gctactagtt gtagagtg                                      28

<210> SEQ ID NO 193
<211> LENGTH: 28
<212> TYPE: DNA
<213> ORGANISM: Artificial Sequence
<220> FEATURE:
<223> OTHER INFORMATION: Primer

<400> SEQUENCE: 193
catccttata aactcacatt tacccatc                                      28

<210> SEQ ID NO 194
<211> LENGTH: 20

```
<212> TYPE: DNA
<213> ORGANISM: Artificial Sequence
<220> FEATURE:
<223> OTHER INFORMATION: Primer

<400> SEQUENCE: 194
ctcatgcaca gacacatgga                                              20

<210> SEQ ID NO 195
<211> LENGTH: 19
<212> TYPE: DNA
<213> ORGANISM: Artificial Sequence
<220> FEATURE:
<223> OTHER INFORMATION: Primer

<400> SEQUENCE: 195
tgtgcactgg tgacaaact                                               19

<210> SEQ ID NO 196
<211> LENGTH: 22
<212> TYPE: DNA
<213> ORGANISM: Artificial Sequence
<220> FEATURE:
<223> OTHER INFORMATION: Primer

<400> SEQUENCE: 196
cgtgggtctc gatattcttc ac                                           22

<210> SEQ ID NO 197
<211> LENGTH: 21
<212> TYPE: DNA
<213> ORGANISM: Artificial Sequence
<220> FEATURE:
<223> OTHER INFORMATION: Primer

<400> SEQUENCE: 197
ggtaccagga gctgatgaaa g                                            21

<210> SEQ ID NO 198
<211> LENGTH: 21
<212> TYPE: DNA
<213> ORGANISM: Artificial Sequence
<220> FEATURE:
<223> OTHER INFORMATION: Primer

<400> SEQUENCE: 198
ggatgtctgt ccactctgaa a                                            21

<210> SEQ ID NO 199
<211> LENGTH: 21
<212> TYPE: DNA
<213> ORGANISM: Artificial Sequence
<220> FEATURE:
<223> OTHER INFORMATION: Primer

<400> SEQUENCE: 199
ggacattgtg tgctgatgat g                                            21

<210> SEQ ID NO 200
<211> LENGTH: 20
<212> TYPE: DNA
<213> ORGANISM: Artificial Sequence
<220> FEATURE:
<223> OTHER INFORMATION: Primer

<400> SEQUENCE: 200
```
ttgggtgaca gagacaaacc                                               20

<210> SEQ ID NO 201
<211> LENGTH: 25
<212> TYPE: DNA
<213> ORGANISM: Artificial Sequence
<220> FEATURE:
<223> OTHER INFORMATION: Primer

<400> SEQUENCE: 201
acaaactgaa ttatgtggga atcag                                         25

<210> SEQ ID NO 202
<211> LENGTH: 20
<212> TYPE: DNA
<213> ORGANISM: Artificial Sequence
<220> FEATURE:
<223> OTHER INFORMATION: Primer

<400> SEQUENCE: 202
ttggtgaatg tgctccctac                                               20

<210> SEQ ID NO 203
<211> LENGTH: 23
<212> TYPE: DNA
<213> ORGANISM: Artificial Sequence
<220> FEATURE:
<223> OTHER INFORMATION: Primer

<400> SEQUENCE: 203
gggttagatg ggtagagatt tgg                                           23

<210> SEQ ID NO 204
<211> LENGTH: 22
<212> TYPE: DNA
<213> ORGANISM: Artificial Sequence
<220> FEATURE:
<223> OTHER INFORMATION: Primer

<400> SEQUENCE: 204
atccagatcg agagacagaa ga                                            22

<210> SEQ ID NO 205
<211> LENGTH: 22
<212> TYPE: DNA
<213> ORGANISM: Artificial Sequence
<220> FEATURE:
<223> OTHER INFORMATION: Primer

<400> SEQUENCE: 205
gtcttacctg cagcatctct ac                                            22

<210> SEQ ID NO 206
<211> LENGTH: 25
<212> TYPE: DNA
<213> ORGANISM: Artificial Sequence
<220> FEATURE:
<223> OTHER INFORMATION: Primer

<400> SEQUENCE: 206
tgaaggagtc aataagctgt tagag                                         25

<210> SEQ ID NO 207
<211> LENGTH: 21
<212> TYPE: DNA
<213> ORGANISM: Artificial Sequence

```
<220> FEATURE:
<223> OTHER INFORMATION: Primer

<400> SEQUENCE: 207
actcctgcag atcagcattt c                                            21

<210> SEQ ID NO 208
<211> LENGTH: 21
<212> TYPE: DNA
<213> ORGANISM: Artificial Sequence
<220> FEATURE:
<223> OTHER INFORMATION: Primer

<400> SEQUENCE: 208
ccaaagccat gtgatcctac a                                            21

<210> SEQ ID NO 209
<211> LENGTH: 20
<212> TYPE: DNA
<213> ORGANISM: Artificial Sequence
<220> FEATURE:
<223> OTHER INFORMATION: Primer

<400> SEQUENCE: 209
atgacacaga catgggaacc                                              20

<210> SEQ ID NO 210
<211> LENGTH: 24
<212> TYPE: DNA
<213> ORGANISM: Artificial Sequence
<220> FEATURE:
<223> OTHER INFORMATION: Primer

<400> SEQUENCE: 210
cactttatct tgctgactac agaa                                         24

<210> SEQ ID NO 211
<211> LENGTH: 28
<212> TYPE: DNA
<213> ORGANISM: Artificial Sequence
<220> FEATURE:
<223> OTHER INFORMATION: Primer

<400> SEQUENCE: 211
cataaaggaa tttataggct gatagctg                                     28

<210> SEQ ID NO 212
<211> LENGTH: 22
<212> TYPE: DNA
<213> ORGANISM: Artificial Sequence
<220> FEATURE:
<223> OTHER INFORMATION: Primer

<400> SEQUENCE: 212
aactgcttat ttctgcttca gt                                           22

<210> SEQ ID NO 213
<211> LENGTH: 23
<212> TYPE: DNA
<213> ORGANISM: Artificial Sequence
<220> FEATURE:
<223> OTHER INFORMATION: Primer

<400> SEQUENCE: 213
ctgtattgtg tctaactgcc caa                                          23
```

<210> SEQ ID NO 214
<211> LENGTH: 23
<212> TYPE: DNA
<213> ORGANISM: Artificial Sequence
<220> FEATURE:
<223> OTHER INFORMATION: Primer

<400> SEQUENCE: 214
cagggcaact atcaaaccat aga                                             23

<210> SEQ ID NO 215
<211> LENGTH: 22
<212> TYPE: DNA
<213> ORGANISM: Artificial Sequence
<220> FEATURE:
<223> OTHER INFORMATION: Primer

<400> SEQUENCE: 215
gttatgccac catcctcact aa                                              22

<210> SEQ ID NO 216
<211> LENGTH: 24
<212> TYPE: DNA
<213> ORGANISM: Artificial Sequence
<220> FEATURE:
<223> OTHER INFORMATION: Primer

<400> SEQUENCE: 216
tcagttacag tcataggacc attc                                            24

<210> SEQ ID NO 217
<211> LENGTH: 19
<212> TYPE: DNA
<213> ORGANISM: Artificial Sequence
<220> FEATURE:
<223> OTHER INFORMATION: Primer

<400> SEQUENCE: 217
agctgttggc tccattcat                                                  19

<210> SEQ ID NO 218
<211> LENGTH: 24
<212> TYPE: DNA
<213> ORGANISM: Artificial Sequence
<220> FEATURE:
<223> OTHER INFORMATION: Primer

<400> SEQUENCE: 218
cctatgccta tgatgtcagg taat                                            24

<210> SEQ ID NO 219
<211> LENGTH: 27
<212> TYPE: DNA
<213> ORGANISM: Artificial Sequence
<220> FEATURE:
<223> OTHER INFORMATION: Primer

<400> SEQUENCE: 219
ctggtagtaa tacactctct tagcttt                                         27

<210> SEQ ID NO 220
<211> LENGTH: 21
<212> TYPE: DNA
<213> ORGANISM: Artificial Sequence
<220> FEATURE:
<223> OTHER INFORMATION: Primer

<400> SEQUENCE: 220
gagtagttgt gacacaggca t                                              21

<210> SEQ ID NO 221
<211> LENGTH: 24
<212> TYPE: DNA
<213> ORGANISM: Artificial Sequence
<220> FEATURE:
<223> OTHER INFORMATION: Primer

<400> SEQUENCE: 221
aaacttgttg gctgacattg atag                                           24

<210> SEQ ID NO 222
<211> LENGTH: 23
<212> TYPE: DNA
<213> ORGANISM: Artificial Sequence
<220> FEATURE:
<223> OTHER INFORMATION: Primer

<400> SEQUENCE: 222
tgtggcagta ttcacagatt ctc                                            23

<210> SEQ ID NO 223
<211> LENGTH: 21
<212> TYPE: DNA
<213> ORGANISM: Artificial Sequence
<220> FEATURE:
<223> OTHER INFORMATION: Primer

<400> SEQUENCE: 223
tccaagccaa gagccaaata a                                              21

<210> SEQ ID NO 224
<211> LENGTH: 23
<212> TYPE: DNA
<213> ORGANISM: Artificial Sequence
<220> FEATURE:
<223> OTHER INFORMATION: Primer

<400> SEQUENCE: 224
gaccatttct taaagccaca caa                                            23

<210> SEQ ID NO 225
<211> LENGTH: 23
<212> TYPE: DNA
<213> ORGANISM: Artificial Sequence
<220> FEATURE:
<223> OTHER INFORMATION: Primer

<400> SEQUENCE: 225
agcccagatt tcaccatgta ata                                            23

<210> SEQ ID NO 226
<211> LENGTH: 20
<212> TYPE: DNA
<213> ORGANISM: Artificial Sequence
<220> FEATURE:
<223> OTHER INFORMATION: Primer

<400> SEQUENCE: 226
attatgtcat gccctgtgct                                                20

<210> SEQ ID NO 227

<211> LENGTH: 21
<212> TYPE: DNA
<213> ORGANISM: Artificial Sequence
<220> FEATURE:
<223> OTHER INFORMATION: Primer

<400> SEQUENCE: 227
ctacactgac ccaaccatct g                                               21

<210> SEQ ID NO 228
<211> LENGTH: 23
<212> TYPE: DNA
<213> ORGANISM: Artificial Sequence
<220> FEATURE:
<223> OTHER INFORMATION: Primer

<400> SEQUENCE: 228
gtgtggaata gaaggacaag tga                                             23

<210> SEQ ID NO 229
<211> LENGTH: 18
<212> TYPE: DNA
<213> ORGANISM: Artificial Sequence
<220> FEATURE:
<223> OTHER INFORMATION: Primer

<400> SEQUENCE: 229
gccaccatgc tcagacaa                                                   18

<210> SEQ ID NO 230
<211> LENGTH: 30
<212> TYPE: DNA
<213> ORGANISM: Artificial Sequence
<220> FEATURE:
<223> OTHER INFORMATION: Primer

<400> SEQUENCE: 230
ggatatgttc cttaatctat gtcaaacagg                                      30

<210> SEQ ID NO 231
<211> LENGTH: 21
<212> TYPE: DNA
<213> ORGANISM: Artificial Sequence
<220> FEATURE:
<223> OTHER INFORMATION: Primer

<400> SEQUENCE: 231
gcagtcctgg gccaatttat g                                               21

<210> SEQ ID NO 232
<211> LENGTH: 24
<212> TYPE: DNA
<213> ORGANISM: Artificial Sequence
<220> FEATURE:
<223> OTHER INFORMATION: Primer

<400> SEQUENCE: 232
actgattaga ttggatgagt tcca                                            24

<210> SEQ ID NO 233
<211> LENGTH: 19
<212> TYPE: DNA
<213> ORGANISM: Artificial Sequence
<220> FEATURE:
<223> OTHER INFORMATION: Primer

<400> SEQUENCE: 233

-continued taagacagag aggcctggt                                              19

<210> SEQ ID NO 234
<211> LENGTH: 24
<212> TYPE: DNA
<213> ORGANISM: Artificial Sequence
<220> FEATURE:
<223> OTHER INFORMATION: Primer

<400> SEQUENCE: 234
catttctctc ttactgcttt gaca                                        24

<210> SEQ ID NO 235
<211> LENGTH: 24
<212> TYPE: DNA
<213> ORGANISM: Artificial Sequence
<220> FEATURE:
<223> OTHER INFORMATION: Primer

<400> SEQUENCE: 235
gaaacagaga gagaagcaaa gaaa                                        24

<210> SEQ ID NO 236
<211> LENGTH: 21
<212> TYPE: DNA
<213> ORGANISM: Artificial Sequence
<220> FEATURE:
<223> OTHER INFORMATION: Primer

<400> SEQUENCE: 236
ggtgacgatg gtgacaactt t                                           21

<210> SEQ ID NO 237
<211> LENGTH: 22
<212> TYPE: DNA
<213> ORGANISM: Artificial Sequence
<220> FEATURE:
<223> OTHER INFORMATION: Primer

<400> SEQUENCE: 237
tgtggtttca ctgcatgtac tc                                          22

<210> SEQ ID NO 238
<211> LENGTH: 24
<212> TYPE: DNA
<213> ORGANISM: Artificial Sequence
<220> FEATURE:
<223> OTHER INFORMATION: Primer

<400> SEQUENCE: 238
cgaagcttga aagacttggt aatg                                        24

<210> SEQ ID NO 239
<211> LENGTH: 22
<212> TYPE: DNA
<213> ORGANISM: Artificial Sequence
<220> FEATURE:
<223> OTHER INFORMATION: Primer

<400> SEQUENCE: 239
ccacctcttc cctaactgaa ag                                          22

<210> SEQ ID NO 240
<211> LENGTH: 20
<212> TYPE: DNA

```
<213> ORGANISM: Artificial Sequence
<220> FEATURE:
<223> OTHER INFORMATION: Primer

<400> SEQUENCE: 240
tacacacagc aggacaactg                                                    20

<210> SEQ ID NO 241
<211> LENGTH: 20
<212> TYPE: DNA
<213> ORGANISM: Artificial Sequence
<220> FEATURE:
<223> OTHER INFORMATION: Primer

<400> SEQUENCE: 241
ctgggctaac acaggatttt                                                    20

<210> SEQ ID NO 242
<211> LENGTH: 22
<212> TYPE: DNA
<213> ORGANISM: Artificial Sequence
<220> FEATURE:
<223> OTHER INFORMATION: Primer

<400> SEQUENCE: 242
aaattgcagt gcttagtgga aa                                                 22

<210> SEQ ID NO 243
<211> LENGTH: 22
<212> TYPE: DNA
<213> ORGANISM: Artificial Sequence
<220> FEATURE:
<223> OTHER INFORMATION: Primer

<400> SEQUENCE: 243
agctaggagt ttagcaactg tg                                                 22

<210> SEQ ID NO 244
<211> LENGTH: 20
<212> TYPE: DNA
<213> ORGANISM: Artificial Sequence
<220> FEATURE:
<223> OTHER INFORMATION: Primer

<400> SEQUENCE: 244
aggaagcctc gtaacatgac                                                    20

<210> SEQ ID NO 245
<211> LENGTH: 27
<212> TYPE: DNA
<213> ORGANISM: Artificial Sequence
<220> FEATURE:
<223> OTHER INFORMATION: Primer

<400> SEQUENCE: 245
ctgattgtct ccactatctt tagaatg                                            27

<210> SEQ ID NO 246
<211> LENGTH: 23
<212> TYPE: DNA
<213> ORGANISM: Artificial Sequence
<220> FEATURE:
<223> OTHER INFORMATION: Primer

<400> SEQUENCE: 246
agccctaaga gatttctcac att                                                23
```

```
<210> SEQ ID NO 247
<211> LENGTH: 23
<212> TYPE: DNA
<213> ORGANISM: Artificial Sequence
<220> FEATURE:
<223> OTHER INFORMATION: Primer

<400> SEQUENCE: 247
tttcctatca ccagtggatt gag                                          23

<210> SEQ ID NO 248
<211> LENGTH: 23
<212> TYPE: DNA
<213> ORGANISM: Artificial Sequence
<220> FEATURE:
<223> OTHER INFORMATION: Primer

<400> SEQUENCE: 248
cattggacta aggtgccaga tag                                          23

<210> SEQ ID NO 249
<211> LENGTH: 20
<212> TYPE: DNA
<213> ORGANISM: Artificial Sequence
<220> FEATURE:
<223> OTHER INFORMATION: Primer

<400> SEQUENCE: 249
ttgtgcttgg gcagagatac                                              20

<210> SEQ ID NO 250
<211> LENGTH: 22
<212> TYPE: DNA
<213> ORGANISM: Artificial Sequence
<220> FEATURE:
<223> OTHER INFORMATION: Primer

<400> SEQUENCE: 250
ccacagtcag aagagtcctt ac                                           22

<210> SEQ ID NO 251
<211> LENGTH: 24
<212> TYPE: DNA
<213> ORGANISM: Artificial Sequence
<220> FEATURE:
<223> OTHER INFORMATION: Primer

<400> SEQUENCE: 251
cacagttcaa cccataacac atag                                         24

<210> SEQ ID NO 252
<211> LENGTH: 20
<212> TYPE: DNA
<213> ORGANISM: Artificial Sequence
<220> FEATURE:
<223> OTHER INFORMATION: Primer

<400> SEQUENCE: 252
ctggacaacg agaacacctt                                              20

<210> SEQ ID NO 253
<211> LENGTH: 23
<212> TYPE: DNA
<213> ORGANISM: Artificial Sequence
<220> FEATURE:
```

```
<223> OTHER INFORMATION: Primer

<400> SEQUENCE: 253
ccttaaaggt ccttatcaca cca                                    23

<210> SEQ ID NO 254
<211> LENGTH: 26
<212> TYPE: DNA
<213> ORGANISM: Artificial Sequence
<220> FEATURE:
<223> OTHER INFORMATION: Primer

<400> SEQUENCE: 254
ttctagaaga catctacata ccttgg                                 26

<210> SEQ ID NO 255
<211> LENGTH: 20
<212> TYPE: DNA
<213> ORGANISM: Artificial Sequence
<220> FEATURE:
<223> OTHER INFORMATION: Primer

<400> SEQUENCE: 255
ggtcttggca ggtacgttta                                        20

<210> SEQ ID NO 256
<211> LENGTH: 22
<212> TYPE: DNA
<213> ORGANISM: Artificial Sequence
<220> FEATURE:
<223> OTHER INFORMATION: Primer

<400> SEQUENCE: 256
ggactggtca agactgaact ac                                     22

<210> SEQ ID NO 257
<211> LENGTH: 21
<212> TYPE: DNA
<213> ORGANISM: Artificial Sequence
<220> FEATURE:
<223> OTHER INFORMATION: Primer

<400> SEQUENCE: 257
ccaatgtgct gttggcttta c                                      21

<210> SEQ ID NO 258
<211> LENGTH: 22
<212> TYPE: DNA
<213> ORGANISM: Artificial Sequence
<220> FEATURE:
<223> OTHER INFORMATION: Primer

<400> SEQUENCE: 258
gggtaaatac agaccacaga tg                                     22

<210> SEQ ID NO 259
<211> LENGTH: 22
<212> TYPE: DNA
<213> ORGANISM: Artificial Sequence
<220> FEATURE:
<223> OTHER INFORMATION: Primer

<400> SEQUENCE: 259
ggaaatccag gttcagaata gt                                     22
```

```
<210> SEQ ID NO 260
<211> LENGTH: 24
<212> TYPE: DNA
<213> ORGANISM: Artificial Sequence
<220> FEATURE:
<223> OTHER INFORMATION: Primer

<400> SEQUENCE: 260
gtggttcttt attgtagccc attt                                              24

<210> SEQ ID NO 261
<211> LENGTH: 21
<212> TYPE: DNA
<213> ORGANISM: Artificial Sequence
<220> FEATURE:
<223> OTHER INFORMATION: Primer

<400> SEQUENCE: 261
tcttccttga gggcaagatt c                                                 21

<210> SEQ ID NO 262
<211> LENGTH: 22
<212> TYPE: DNA
<213> ORGANISM: Artificial Sequence
<220> FEATURE:
<223> OTHER INFORMATION: Primer

<400> SEQUENCE: 262
agaatgtgga caggtcatta gc                                                22

<210> SEQ ID NO 263
<211> LENGTH: 27
<212> TYPE: DNA
<213> ORGANISM: Artificial Sequence
<220> FEATURE:
<223> OTHER INFORMATION: Primer

<400> SEQUENCE: 263
ctaagctatc tatggttgtt atgagga                                           27

<210> SEQ ID NO 264
<211> LENGTH: 21
<212> TYPE: DNA
<213> ORGANISM: Artificial Sequence
<220> FEATURE:
<223> OTHER INFORMATION: Primer

<400> SEQUENCE: 264
tccctgaggt caagactatg t                                                 21

<210> SEQ ID NO 265
<211> LENGTH: 21
<212> TYPE: DNA
<213> ORGANISM: Artificial Sequence
<220> FEATURE:
<223> OTHER INFORMATION: Primer

<400> SEQUENCE: 265
tctatgctcc tgcttctctc t                                                 21

<210> SEQ ID NO 266
<211> LENGTH: 25
<212> TYPE: DNA
<213> ORGANISM: Artificial Sequence
<220> FEATURE:
<223> OTHER INFORMATION: Primer
```

```
<400> SEQUENCE: 266
ctttctgaag tgtgaattac cacaa                                         25

<210> SEQ ID NO 267
<211> LENGTH: 21
<212> TYPE: DNA
<213> ORGANISM: Artificial Sequence
<220> FEATURE:
<223> OTHER INFORMATION: Primer

<400> SEQUENCE: 267
aagaaatgtg ggcagcttct a                                             21

<210> SEQ ID NO 268
<211> LENGTH: 23
<212> TYPE: DNA
<213> ORGANISM: Artificial Sequence
<220> FEATURE:
<223> OTHER INFORMATION: Primer

<400> SEQUENCE: 268
gaggcacaga tataagccac ata                                           23

<210> SEQ ID NO 269
<211> LENGTH: 20
<212> TYPE: DNA
<213> ORGANISM: Artificial Sequence
<220> FEATURE:
<223> OTHER INFORMATION: Primer

<400> SEQUENCE: 269
ccagtaacaa ccctgcttca                                               20

<210> SEQ ID NO 270
<211> LENGTH: 23
<212> TYPE: DNA
<213> ORGANISM: Artificial Sequence
<220> FEATURE:
<223> OTHER INFORMATION: Primer

<400> SEQUENCE: 270
gacaagatga tggagcagaa gag                                           23

<210> SEQ ID NO 271
<211> LENGTH: 26
<212> TYPE: DNA
<213> ORGANISM: Artificial Sequence
<220> FEATURE:
<223> OTHER INFORMATION: Primer

<400> SEQUENCE: 271
tgtcagggaa atctatttca ggttag                                        26

<210> SEQ ID NO 272
<211> LENGTH: 22
<212> TYPE: DNA
<213> ORGANISM: Artificial Sequence
<220> FEATURE:
<223> OTHER INFORMATION: Primer

<400> SEQUENCE: 272
ggtaaaggaa gctctggaag aa                                            22

<210> SEQ ID NO 273
<211> LENGTH: 22
```

```
<212> TYPE: DNA
<213> ORGANISM: Artificial Sequence
<220> FEATURE:
<223> OTHER INFORMATION: Primer

<400> SEQUENCE: 273
catccatgct aacggagtag tt                                              22

<210> SEQ ID NO 274
<211> LENGTH: 23
<212> TYPE: DNA
<213> ORGANISM: Artificial Sequence
<220> FEATURE:
<223> OTHER INFORMATION: Primer

<400> SEQUENCE: 274
ctgccactta gaagtaggaa tga                                             23

<210> SEQ ID NO 275
<211> LENGTH: 22
<212> TYPE: DNA
<213> ORGANISM: Artificial Sequence
<220> FEATURE:
<223> OTHER INFORMATION: Primer

<400> SEQUENCE: 275
gtggctgatc tgtgaggata aa                                              22

<210> SEQ ID NO 276
<211> LENGTH: 20
<212> TYPE: DNA
<213> ORGANISM: Artificial Sequence
<220> FEATURE:
<223> OTHER INFORMATION: Primer

<400> SEQUENCE: 276
ttcctcctct ctggaggttt                                                 20

<210> SEQ ID NO 277
<211> LENGTH: 23
<212> TYPE: DNA
<213> ORGANISM: Artificial Sequence
<220> FEATURE:
<223> OTHER INFORMATION: Primer

<400> SEQUENCE: 277
cattgagcaa gcttcatgta ctc                                             23

<210> SEQ ID NO 278
<211> LENGTH: 21
<212> TYPE: DNA
<213> ORGANISM: Artificial Sequence
<220> FEATURE:
<223> OTHER INFORMATION: Primer

<400> SEQUENCE: 278
tggagggcag tctgaaatat g                                               21

<210> SEQ ID NO 279
<211> LENGTH: 26
<212> TYPE: DNA
<213> ORGANISM: Artificial Sequence
<220> FEATURE:
<223> OTHER INFORMATION: Primer

<400> SEQUENCE: 279
```

```
gtaagtaact gtttggtact ctgttg                                          26

<210> SEQ ID NO 280
<211> LENGTH: 22
<212> TYPE: DNA
<213> ORGANISM: Artificial Sequence
<220> FEATURE:
<223> OTHER INFORMATION: Primer

<400> SEQUENCE: 280
aaacatccct ctgcaatcca tc                                              22

<210> SEQ ID NO 281
<211> LENGTH: 28
<212> TYPE: DNA
<213> ORGANISM: Artificial Sequence
<220> FEATURE:
<223> OTHER INFORMATION: Primer

<400> SEQUENCE: 281
tatccttgaa atccatatta gcagaagc                                        28

<210> SEQ ID NO 282
<211> LENGTH: 22
<212> TYPE: DNA
<213> ORGANISM: Artificial Sequence
<220> FEATURE:
<223> OTHER INFORMATION: Primer

<400> SEQUENCE: 282
cccaatctga cagcacaatt tc                                              22

<210> SEQ ID NO 283
<211> LENGTH: 22
<212> TYPE: DNA
<213> ORGANISM: Artificial Sequence
<220> FEATURE:
<223> OTHER INFORMATION: Primer

<400> SEQUENCE: 283
ccaagttact tagcctggag tt                                              22

<210> SEQ ID NO 284
<211> LENGTH: 22
<212> TYPE: DNA
<213> ORGANISM: Artificial Sequence
<220> FEATURE:
<223> OTHER INFORMATION: Primer

<400> SEQUENCE: 284
accaggacag acacagatta tt                                              22

<210> SEQ ID NO 285
<211> LENGTH: 22
<212> TYPE: DNA
<213> ORGANISM: Artificial Sequence
<220> FEATURE:
<223> OTHER INFORMATION: Primer

<400> SEQUENCE: 285
caagaccatc tcagatccct ac                                              22

<210> SEQ ID NO 286
<211> LENGTH: 23
<212> TYPE: DNA
<213> ORGANISM: Artificial Sequence
```

<220> FEATURE:
<223> OTHER INFORMATION: Primer

<400> SEQUENCE: 286
gggatggaag ggtaaataag aca         23

<210> SEQ ID NO 287
<211> LENGTH: 22
<212> TYPE: DNA
<213> ORGANISM: Artificial Sequence
<220> FEATURE:
<223> OTHER INFORMATION: Primer

<400> SEQUENCE: 287
gctgctagag tctcagtatc ac          22

<210> SEQ ID NO 288
<211> LENGTH: 19
<212> TYPE: DNA
<213> ORGANISM: Artificial Sequence
<220> FEATURE:
<223> OTHER INFORMATION: Primer

<400> SEQUENCE: 288
ggaaagcctg gagtgtgag              19

<210> SEQ ID NO 289
<211> LENGTH: 23
<212> TYPE: DNA
<213> ORGANISM: Artificial Sequence
<220> FEATURE:
<223> OTHER INFORMATION: Primer

<400> SEQUENCE: 289
atacaacaga gtgctggact tag         23

<210> SEQ ID NO 290
<211> LENGTH: 21
<212> TYPE: DNA
<213> ORGANISM: Artificial Sequence
<220> FEATURE:
<223> OTHER INFORMATION: Primer

<400> SEQUENCE: 290
aagttggagg attcacgctt c           21

<210> SEQ ID NO 291
<211> LENGTH: 23
<212> TYPE: DNA
<213> ORGANISM: Artificial Sequence
<220> FEATURE:
<223> OTHER INFORMATION: Primer

<400> SEQUENCE: 291
tcagattgtg tcagcaccat tta         23

<210> SEQ ID NO 292
<211> LENGTH: 20
<212> TYPE: DNA
<213> ORGANISM: Artificial Sequence
<220> FEATURE:
<223> OTHER INFORMATION: Primer

<400> SEQUENCE: 292
gtttgcttgg ctgcagtaat             20

```
<210> SEQ ID NO 293
<211> LENGTH: 22
<212> TYPE: DNA
<213> ORGANISM: Artificial Sequence
<220> FEATURE:
<223> OTHER INFORMATION: Primer

<400> SEQUENCE: 293
aagtcccaaa ggaaggtaag ag                                              22

<210> SEQ ID NO 294
<211> LENGTH: 21
<212> TYPE: DNA
<213> ORGANISM: Artificial Sequence
<220> FEATURE:
<223> OTHER INFORMATION: Primer

<400> SEQUENCE: 294
acttgctctt gtacccatca c                                               21

<210> SEQ ID NO 295
<211> LENGTH: 22
<212> TYPE: DNA
<213> ORGANISM: Artificial Sequence
<220> FEATURE:
<223> OTHER INFORMATION: Primer

<400> SEQUENCE: 295
atgtttcatg aactgggcaa tc                                              22

<210> SEQ ID NO 296
<211> LENGTH: 25
<212> TYPE: DNA
<213> ORGANISM: Artificial Sequence
<220> FEATURE:
<223> OTHER INFORMATION: Primer

<400> SEQUENCE: 296
gagggagatc tttatccatc tcaag                                           25

<210> SEQ ID NO 297
<211> LENGTH: 23
<212> TYPE: DNA
<213> ORGANISM: Artificial Sequence
<220> FEATURE:
<223> OTHER INFORMATION: Primer

<400> SEQUENCE: 297
tggagaccaa taatccactg ttt                                             23

<210> SEQ ID NO 298
<211> LENGTH: 25
<212> TYPE: DNA
<213> ORGANISM: Artificial Sequence
<220> FEATURE:
<223> OTHER INFORMATION: Primer

<400> SEQUENCE: 298
cctttaatcc tttaatctgg gcaag                                           25

<210> SEQ ID NO 299
<211> LENGTH: 21
<212> TYPE: DNA
<213> ORGANISM: Artificial Sequence
<220> FEATURE:
<223> OTHER INFORMATION: Primer
```

<400> SEQUENCE: 299
tcctagcctt cacatccagt a                                              21

<210> SEQ ID NO 300
<211> LENGTH: 23
<212> TYPE: DNA
<213> ORGANISM: Artificial Sequence
<220> FEATURE:
<223> OTHER INFORMATION: Primer

<400> SEQUENCE: 300
accttctatt cctgctagca aat                                            23

<210> SEQ ID NO 301
<211> LENGTH: 22
<212> TYPE: DNA
<213> ORGANISM: Artificial Sequence
<220> FEATURE:
<223> OTHER INFORMATION: Primer

<400> SEQUENCE: 301
cacaaatgac ccaaatgact gg                                             22

<210> SEQ ID NO 302
<211> LENGTH: 22
<212> TYPE: DNA
<213> ORGANISM: Artificial Sequence
<220> FEATURE:
<223> OTHER INFORMATION: Primer

<400> SEQUENCE: 302
ctcagctcat ctgtaactcc ac                                             22

<210> SEQ ID NO 303
<211> LENGTH: 21
<212> TYPE: DNA
<213> ORGANISM: Artificial Sequence
<220> FEATURE:
<223> OTHER INFORMATION: Primer

<400> SEQUENCE: 303
tgtccatggt tgtctgcata a                                              21

<210> SEQ ID NO 304
<211> LENGTH: 22
<212> TYPE: DNA
<213> ORGANISM: Artificial Sequence
<220> FEATURE:
<223> OTHER INFORMATION: Primer

<400> SEQUENCE: 304
agcacatctg gaaagtgaaa tg                                             22

<210> SEQ ID NO 305
<211> LENGTH: 22
<212> TYPE: DNA
<213> ORGANISM: Artificial Sequence
<220> FEATURE:
<223> OTHER INFORMATION: Primer

<400> SEQUENCE: 305
gagtgagcca agttggttaa tg                                             22

<210> SEQ ID NO 306

```
<211> LENGTH: 21
<212> TYPE: DNA
<213> ORGANISM: Artificial Sequence
<220> FEATURE:
<223> OTHER INFORMATION: Primer

<400> SEQUENCE: 306
accatcctcc actctcatct t                                               21

<210> SEQ ID NO 307
<211> LENGTH: 19
<212> TYPE: DNA
<213> ORGANISM: Artificial Sequence
<220> FEATURE:
<223> OTHER INFORMATION: Primer

<400> SEQUENCE: 307
ccaggcgcca gaaacttta                                                  19

<210> SEQ ID NO 308
<211> LENGTH: 21
<212> TYPE: DNA
<213> ORGANISM: Artificial Sequence
<220> FEATURE:
<223> OTHER INFORMATION: Primer

<400> SEQUENCE: 308
caaaccctcc gagacagtaa a                                               21

<210> SEQ ID NO 309
<211> LENGTH: 23
<212> TYPE: DNA
<213> ORGANISM: Artificial Sequence
<220> FEATURE:
<223> OTHER INFORMATION: Primer

<400> SEQUENCE: 309
cttctacaat tggtccaggt agg                                             23

<210> SEQ ID NO 310
<211> LENGTH: 23
<212> TYPE: DNA
<213> ORGANISM: Artificial Sequence
<220> FEATURE:
<223> OTHER INFORMATION: Primer

<400> SEQUENCE: 310
aacacatttc catcagtgct ttg                                             23

<210> SEQ ID NO 311
<211> LENGTH: 28
<212> TYPE: DNA
<213> ORGANISM: Artificial Sequence
<220> FEATURE:
<223> OTHER INFORMATION: Primer

<400> SEQUENCE: 311
cagacaagtt tcagcttatt tcttactc                                        28

<210> SEQ ID NO 312
<211> LENGTH: 27
<212> TYPE: DNA
<213> ORGANISM: Artificial Sequence
<220> FEATURE:
<223> OTHER INFORMATION: Primer

<400> SEQUENCE: 312
```
gttactcatt aggtgaatgc ttgtatc					27

<210> SEQ ID NO 313
<211> LENGTH: 20
<212> TYPE: DNA
<213> ORGANISM: Artificial Sequence
<220> FEATURE:
<223> OTHER INFORMATION: Primer

<400> SEQUENCE: 313
aaccttgcac tcatccttcc					20

<210> SEQ ID NO 314
<211> LENGTH: 19
<212> TYPE: DNA
<213> ORGANISM: Artificial Sequence
<220> FEATURE:
<223> OTHER INFORMATION: Primer

<400> SEQUENCE: 314
caccacgccc agaatctat					19

<210> SEQ ID NO 315
<211> LENGTH: 27
<212> TYPE: DNA
<213> ORGANISM: Artificial Sequence
<220> FEATURE:
<223> OTHER INFORMATION: Primer

<400> SEQUENCE: 315
cttagtcact tagagcttaa actaagg					27

<210> SEQ ID NO 316
<211> LENGTH: 22
<212> TYPE: DNA
<213> ORGANISM: Artificial Sequence
<220> FEATURE:
<223> OTHER INFORMATION: Primer

<400> SEQUENCE: 316
aatgcatcaa gaagcatgtg tt					22

<210> SEQ ID NO 317
<211> LENGTH: 28
<212> TYPE: DNA
<213> ORGANISM: Artificial Sequence
<220> FEATURE:
<223> OTHER INFORMATION: Primer

<400> SEQUENCE: 317
cttcaaattc cctacaaatt tctaccac					28

<210> SEQ ID NO 318
<211> LENGTH: 22
<212> TYPE: DNA
<213> ORGANISM: Artificial Sequence
<220> FEATURE:
<223> OTHER INFORMATION: Primer

<400> SEQUENCE: 318
ggatgatgtc acagaagctg ag					22

<210> SEQ ID NO 319
<211> LENGTH: 20
<212> TYPE: DNA

```
<213> ORGANISM: Artificial Sequence
<220> FEATURE:
<223> OTHER INFORMATION: Primer

<400> SEQUENCE: 319
ggcacaggaa cgctcataat                                               20

<210> SEQ ID NO 320
<211> LENGTH: 20
<212> TYPE: DNA
<213> ORGANISM: Artificial Sequence
<220> FEATURE:
<223> OTHER INFORMATION: Primer

<400> SEQUENCE: 320
ggctgaaact tcgctgaaac                                               20

<210> SEQ ID NO 321
<211> LENGTH: 26
<212> TYPE: DNA
<213> ORGANISM: Artificial Sequence
<220> FEATURE:
<223> OTHER INFORMATION: Primer

<400> SEQUENCE: 321
catgcttcaa gtacctaaat gactac                                        26

<210> SEQ ID NO 322
<211> LENGTH: 20
<212> TYPE: DNA
<213> ORGANISM: Artificial Sequence
<220> FEATURE:
<223> OTHER INFORMATION: Primer

<400> SEQUENCE: 322
gctggctgtt caggtacatt                                               20

<210> SEQ ID NO 323
<211> LENGTH: 22
<212> TYPE: DNA
<213> ORGANISM: Artificial Sequence
<220> FEATURE:
<223> OTHER INFORMATION: Primer

<400> SEQUENCE: 323
gaaaccagta ggaggctaga ga                                            22

<210> SEQ ID NO 324
<211> LENGTH: 22
<212> TYPE: DNA
<213> ORGANISM: Artificial Sequence
<220> FEATURE:
<223> OTHER INFORMATION: Primer

<400> SEQUENCE: 324
cctctctttc cttcatcttg gg                                            22

<210> SEQ ID NO 325
<211> LENGTH: 18
<212> TYPE: DNA
<213> ORGANISM: Artificial Sequence
<220> FEATURE:
<223> OTHER INFORMATION: Primer

<400> SEQUENCE: 325
ttggacaagg cagccaaa                                                 18
```

<210> SEQ ID NO 326
<211> LENGTH: 18
<212> TYPE: DNA
<213> ORGANISM: Artificial Sequence
<220> FEATURE:
<223> OTHER INFORMATION: Primer

<400> SEQUENCE: 326
gttgtgaggg aggagtca                                          18

<210> SEQ ID NO 327
<211> LENGTH: 25
<212> TYPE: DNA
<213> ORGANISM: Artificial Sequence
<220> FEATURE:
<223> OTHER INFORMATION: Primer

<400> SEQUENCE: 327
ccctcattta ataccctagt aactt                                  25

<210> SEQ ID NO 328
<211> LENGTH: 20
<212> TYPE: DNA
<213> ORGANISM: Artificial Sequence
<220> FEATURE:
<223> OTHER INFORMATION: Primer

<400> SEQUENCE: 328
ctgcaaggcc taggcttaat                                        20

<210> SEQ ID NO 329
<211> LENGTH: 22
<212> TYPE: DNA
<213> ORGANISM: Artificial Sequence
<220> FEATURE:
<223> OTHER INFORMATION: Primer

<400> SEQUENCE: 329
tttggctatt ctgggtctct tt                                     22

<210> SEQ ID NO 330
<211> LENGTH: 20
<212> TYPE: DNA
<213> ORGANISM: Artificial Sequence
<220> FEATURE:
<223> OTHER INFORMATION: Primer

<400> SEQUENCE: 330
ggcaacatgc atttggactt                                        20

<210> SEQ ID NO 331
<211> LENGTH: 18
<212> TYPE: DNA
<213> ORGANISM: Artificial Sequence
<220> FEATURE:
<223> OTHER INFORMATION: Primer

<400> SEQUENCE: 331
tgctggcatc actgttgt                                          18

<210> SEQ ID NO 332
<211> LENGTH: 20
<212> TYPE: DNA
<213> ORGANISM: Artificial Sequence
<220> FEATURE:

<223> OTHER INFORMATION: Primer

<400> SEQUENCE: 332
atggagggcc atttgaagaa                                       20

<210> SEQ ID NO 333
<211> LENGTH: 21
<212> TYPE: DNA
<213> ORGANISM: Artificial Sequence
<220> FEATURE:
<223> OTHER INFORMATION: Primer

<400> SEQUENCE: 333
cctccctctc tctccataga c                                     21

<210> SEQ ID NO 334
<211> LENGTH: 22
<212> TYPE: DNA
<213> ORGANISM: Artificial Sequence
<220> FEATURE:
<223> OTHER INFORMATION: Primer

<400> SEQUENCE: 334
gctcaccttc ctttcacaca ta                                    22

<210> SEQ ID NO 335
<211> LENGTH: 20
<212> TYPE: DNA
<213> ORGANISM: Artificial Sequence
<220> FEATURE:
<223> OTHER INFORMATION: Primer

<400> SEQUENCE: 335
aaaggcagct aatgcagtct                                       20

<210> SEQ ID NO 336
<211> LENGTH: 24
<212> TYPE: DNA
<213> ORGANISM: Artificial Sequence
<220> FEATURE:
<223> OTHER INFORMATION: Primer

<400> SEQUENCE: 336
tacatcaccc aactttgaca agta                                  24

<210> SEQ ID NO 337
<211> LENGTH: 24
<212> TYPE: DNA
<213> ORGANISM: Artificial Sequence
<220> FEATURE:
<223> OTHER INFORMATION: Primer

<400> SEQUENCE: 337
tttattaagc accttctcaa tgcc                                  24

<210> SEQ ID NO 338
<211> LENGTH: 22
<212> TYPE: DNA
<213> ORGANISM: Artificial Sequence
<220> FEATURE:
<223> OTHER INFORMATION: Primer

<400> SEQUENCE: 338
gggacacata aggacttgta cg                                    22

```
<210> SEQ ID NO 339
<211> LENGTH: 20
<212> TYPE: DNA
<213> ORGANISM: Artificial Sequence
<220> FEATURE:
<223> OTHER INFORMATION: Primer

<400> SEQUENCE: 339
tgtgtctggc ttctttgagg                                                   20

<210> SEQ ID NO 340
<211> LENGTH: 22
<212> TYPE: DNA
<213> ORGANISM: Artificial Sequence
<220> FEATURE:
<223> OTHER INFORMATION: Primer

<400> SEQUENCE: 340
aattagttga gaggtgcaag gt                                                22

<210> SEQ ID NO 341
<211> LENGTH: 20
<212> TYPE: DNA
<213> ORGANISM: Artificial Sequence
<220> FEATURE:
<223> OTHER INFORMATION: Primer

<400> SEQUENCE: 341
tctccttcta ctgccatcct                                                   20

<210> SEQ ID NO 342
<211> LENGTH: 20
<212> TYPE: DNA
<213> ORGANISM: Artificial Sequence
<220> FEATURE:
<223> OTHER INFORMATION: Primer

<400> SEQUENCE: 342
acctggttgc ctatgttgac                                                   20

<210> SEQ ID NO 343
<211> LENGTH: 20
<212> TYPE: DNA
<213> ORGANISM: Artificial Sequence
<220> FEATURE:
<223> OTHER INFORMATION: Primer

<400> SEQUENCE: 343
tcagtgggaa aggacagtct                                                   20

<210> SEQ ID NO 344
<211> LENGTH: 21
<212> TYPE: DNA
<213> ORGANISM: Artificial Sequence
<220> FEATURE:
<223> OTHER INFORMATION: Primer

<400> SEQUENCE: 344
gcctagcagt gggtgtataa t                                                 21

<210> SEQ ID NO 345
<211> LENGTH: 22
<212> TYPE: DNA
<213> ORGANISM: Artificial Sequence
<220> FEATURE:
<223> OTHER INFORMATION: Primer
```

<400> SEQUENCE: 345
gagtgttgct tgagttctgt tt    22

<210> SEQ ID NO 346
<211> LENGTH: 21
<212> TYPE: DNA
<213> ORGANISM: Artificial Sequence
<220> FEATURE:
<223> OTHER INFORMATION: Primer

<400> SEQUENCE: 346
tcccgaagtg ctaggattag a    21

<210> SEQ ID NO 347
<211> LENGTH: 22
<212> TYPE: DNA
<213> ORGANISM: Artificial Sequence
<220> FEATURE:
<223> OTHER INFORMATION: Primer

<400> SEQUENCE: 347
tgtgcggtat gtatgtgtat gt    22

<210> SEQ ID NO 348
<211> LENGTH: 21
<212> TYPE: DNA
<213> ORGANISM: Artificial Sequence
<220> FEATURE:
<223> OTHER INFORMATION: Primer

<400> SEQUENCE: 348
ctcctcccac cacacaatta c    21

<210> SEQ ID NO 349
<211> LENGTH: 19
<212> TYPE: DNA
<213> ORGANISM: Artificial Sequence
<220> FEATURE:
<223> OTHER INFORMATION: Primer

<400> SEQUENCE: 349
ggaaggtggt ggcttgatt    19

<210> SEQ ID NO 350
<211> LENGTH: 22
<212> TYPE: DNA
<213> ORGANISM: Artificial Sequence
<220> FEATURE:
<223> OTHER INFORMATION: Primer

<400> SEQUENCE: 350
gttggccttc tcctcagtat ag    22

<210> SEQ ID NO 351
<211> LENGTH: 18
<212> TYPE: DNA
<213> ORGANISM: Artificial Sequence
<220> FEATURE:
<223> OTHER INFORMATION: Primer

<400> SEQUENCE: 351
ggccttgggc atcaacta    18

<210> SEQ ID NO 352
<211> LENGTH: 22

<212> TYPE: DNA
<213> ORGANISM: Artificial Sequence
<220> FEATURE:
<223> OTHER INFORMATION: Primer

<400> SEQUENCE: 352
ctcaattagg aggcagctta ga        22

<210> SEQ ID NO 353
<211> LENGTH: 21
<212> TYPE: DNA
<213> ORGANISM: Artificial Sequence
<220> FEATURE:
<223> OTHER INFORMATION: Primer

<400> SEQUENCE: 353
ggaggtggct aagcactata a         21

<210> SEQ ID NO 354
<211> LENGTH: 20
<212> TYPE: DNA
<213> ORGANISM: Artificial Sequence
<220> FEATURE:
<223> OTHER INFORMATION: Primer

<400> SEQUENCE: 354
tgaaccagag aaggctgcta           20

<210> SEQ ID NO 355
<211> LENGTH: 22
<212> TYPE: DNA
<213> ORGANISM: Artificial Sequence
<220> FEATURE:
<223> OTHER INFORMATION: Primer

<400> SEQUENCE: 355
ggccttggaa gatgaacaga at        22

<210> SEQ ID NO 356
<211> LENGTH: 18
<212> TYPE: DNA
<213> ORGANISM: Artificial Sequence
<220> FEATURE:
<223> OTHER INFORMATION: Primer

<400> SEQUENCE: 356
gtggtgaagc ccacactt             18

<210> SEQ ID NO 357
<211> LENGTH: 20
<212> TYPE: DNA
<213> ORGANISM: Artificial Sequence
<220> FEATURE:
<223> OTHER INFORMATION: Primer

<400> SEQUENCE: 357
cagccaagct ttgggaaatc           20

<210> SEQ ID NO 358
<211> LENGTH: 18
<212> TYPE: DNA
<213> ORGANISM: Artificial Sequence
<220> FEATURE:
<223> OTHER INFORMATION: Primer

<400> SEQUENCE: 358
ggagggacgg agcttcta                                              18

<210> SEQ ID NO 359
<211> LENGTH: 18
<212> TYPE: DNA
<213> ORGANISM: Artificial Sequence
<220> FEATURE:
<223> OTHER INFORMATION: Primer

<400> SEQUENCE: 359
agcctccagc catatcct                                              18

<210> SEQ ID NO 360
<211> LENGTH: 20
<212> TYPE: DNA
<213> ORGANISM: Artificial Sequence
<220> FEATURE:
<223> OTHER INFORMATION: Primer

<400> SEQUENCE: 360
gaaacctcca gggtctttct                                            20

<210> SEQ ID NO 361
<211> LENGTH: 18
<212> TYPE: DNA
<213> ORGANISM: Artificial Sequence
<220> FEATURE:
<223> OTHER INFORMATION: Primer

<400> SEQUENCE: 361
tggagccatt gcagactt                                              18

<210> SEQ ID NO 362
<211> LENGTH: 20
<212> TYPE: DNA
<213> ORGANISM: Artificial Sequence
<220> FEATURE:
<223> OTHER INFORMATION: Primer

<400> SEQUENCE: 362
catgccggaa gatgacaaca                                            20

<210> SEQ ID NO 363
<211> LENGTH: 20
<212> TYPE: DNA
<213> ORGANISM: Artificial Sequence
<220> FEATURE:
<223> OTHER INFORMATION: Primer

<400> SEQUENCE: 363
aaacccattg agccactcag                                            20

<210> SEQ ID NO 364
<211> LENGTH: 18
<212> TYPE: DNA
<213> ORGANISM: Artificial Sequence
<220> FEATURE:
<223> OTHER INFORMATION: Primer

<400> SEQUENCE: 364
tagatgagcc tccggcaa                                              18

<210> SEQ ID NO 365
<211> LENGTH: 18
<212> TYPE: DNA
<213> ORGANISM: Artificial Sequence
<220> FEATURE:
<223> OTHER INFORMATION: Primer

<400> SEQUENCE: 365
ttggcacctc agcctagt                                                    18

<210> SEQ ID NO 366
<211> LENGTH: 20
<212> TYPE: DNA
<213> ORGANISM: Artificial Sequence
<220> FEATURE:
<223> OTHER INFORMATION: Primer

<400> SEQUENCE: 366
ggaaagccaa gggtagaaca                                                  20

<210> SEQ ID NO 367
<211> LENGTH: 21
<212> TYPE: DNA
<213> ORGANISM: Artificial Sequence
<220> FEATURE:
<223> OTHER INFORMATION: Primer

<400> SEQUENCE: 367
gtggtcccaa taacaggtgt a                                                21

<210> SEQ ID NO 368
<211> LENGTH: 21
<212> TYPE: DNA
<213> ORGANISM: Artificial Sequence
<220> FEATURE:
<223> OTHER INFORMATION: Primer

<400> SEQUENCE: 368
catcaccctg cctgtatctt t                                                21

<210> SEQ ID NO 369
<211> LENGTH: 22
<212> TYPE: DNA
<213> ORGANISM: Artificial Sequence
<220> FEATURE:
<223> OTHER INFORMATION: Primer

<400> SEQUENCE: 369
gggagtaacc agtgatgaga tg                                               22

<210> SEQ ID NO 370
<211> LENGTH: 22
<212> TYPE: DNA
<213> ORGANISM: Artificial Sequence
<220> FEATURE:
<223> OTHER INFORMATION: Primer

<400> SEQUENCE: 370
atagggagga atatcggcta gg                                               22

<210> SEQ ID NO 371
<211> LENGTH: 22
<212> TYPE: DNA
<213> ORGANISM: Artificial Sequence
<220> FEATURE:
<223> OTHER INFORMATION: Primer

<400> SEQUENCE: 371
ctggagctag ggcataagat tc                                               22

<210> SEQ ID NO 372
<211> LENGTH: 20
<212> TYPE: DNA
<213> ORGANISM: Artificial Sequence
<220> FEATURE:
<223> OTHER INFORMATION: Primer

<400> SEQUENCE: 372
agctggatga gtttggctac                                                 20

<210> SEQ ID NO 373
<211> LENGTH: 21
<212> TYPE: DNA
<213> ORGANISM: Artificial Sequence
<220> FEATURE:
<223> OTHER INFORMATION: Primer

<400> SEQUENCE: 373
gggcctgtga ttctctgtaa a                                               21

<210> SEQ ID NO 374
<211> LENGTH: 19
<212> TYPE: DNA
<213> ORGANISM: Artificial Sequence
<220> FEATURE:
<223> OTHER INFORMATION: Primer

<400> SEQUENCE: 374
tagttaggag cacgtggga                                                  19

<210> SEQ ID NO 375
<211> LENGTH: 21
<212> TYPE: DNA
<213> ORGANISM: Artificial Sequence
<220> FEATURE:
<223> OTHER INFORMATION: Primer

<400> SEQUENCE: 375
ggcttatgtg catccttctc t                                               21

<210> SEQ ID NO 376
<211> LENGTH: 20
<212> TYPE: DNA
<213> ORGANISM: Artificial Sequence
<220> FEATURE:
<223> OTHER INFORMATION: Primer

<400> SEQUENCE: 376
ggacccagag caaatctagt                                                 20

<210> SEQ ID NO 377
<211> LENGTH: 21
<212> TYPE: DNA
<213> ORGANISM: Artificial Sequence
<220> FEATURE:
<223> OTHER INFORMATION: Primer

<400> SEQUENCE: 377
agggtttgga tgagtctaag g                                               21

<210> SEQ ID NO 378
<211> LENGTH: 19
<212> TYPE: DNA
<213> ORGANISM: Artificial Sequence
<220> FEATURE:
<223> OTHER INFORMATION: Primer

<400> SEQUENCE: 378
ggagactgag tcgggaaca                                              19

<210> SEQ ID NO 379
<211> LENGTH: 23
<212> TYPE: DNA
<213> ORGANISM: Artificial Sequence
<220> FEATURE:
<223> OTHER INFORMATION: Primer

<400> SEQUENCE: 379
tctctgacac tgctatcttc tct                                         23

<210> SEQ ID NO 380
<211> LENGTH: 22
<212> TYPE: DNA
<213> ORGANISM: Artificial Sequence
<220> FEATURE:
<223> OTHER INFORMATION: Primer

<400> SEQUENCE: 380
gtctgaggaa agagacctga tg                                          22

<210> SEQ ID NO 381
<211> LENGTH: 20
<212> TYPE: DNA
<213> ORGANISM: Artificial Sequence
<220> FEATURE:
<223> OTHER INFORMATION: Primer

<400> SEQUENCE: 381
gctaaagtgc cttgctgaag                                             20

<210> SEQ ID NO 382
<211> LENGTH: 20
<212> TYPE: DNA
<213> ORGANISM: Artificial Sequence
<220> FEATURE:
<223> OTHER INFORMATION: Primer

<400> SEQUENCE: 382
cttgtccttg gtgggcattt                                             20

<210> SEQ ID NO 383
<211> LENGTH: 18
<212> TYPE: DNA
<213> ORGANISM: Artificial Sequence
<220> FEATURE:
<223> OTHER INFORMATION: Primer

<400> SEQUENCE: 383
tgtcagagca caggctga                                               18

<210> SEQ ID NO 384
<211> LENGTH: 19
<212> TYPE: DNA
<213> ORGANISM: Artificial Sequence
<220> FEATURE:
<223> OTHER INFORMATION: Primer

<400> SEQUENCE: 384
cccagagctg ctgtgaatg                                              19

<210> SEQ ID NO 385

```
<211> LENGTH: 22
<212> TYPE: DNA
<213> ORGANISM: Artificial Sequence
<220> FEATURE:
<223> OTHER INFORMATION: Primer

<400> SEQUENCE: 385
cttgagaagt ggccttcttt ga                                              22

<210> SEQ ID NO 386
<211> LENGTH: 22
<212> TYPE: DNA
<213> ORGANISM: Artificial Sequence
<220> FEATURE:
<223> OTHER INFORMATION: Primer

<400> SEQUENCE: 386
gatccttctg atggcccaaa ta                                              22

<210> SEQ ID NO 387
<211> LENGTH: 22
<212> TYPE: DNA
<213> ORGANISM: Artificial Sequence
<220> FEATURE:
<223> OTHER INFORMATION: Primer

<400> SEQUENCE: 387
ggaagggtct tcatcagcta ag                                              22

<210> SEQ ID NO 388
<211> LENGTH: 20
<212> TYPE: DNA
<213> ORGANISM: Artificial Sequence
<220> FEATURE:
<223> OTHER INFORMATION: Primer

<400> SEQUENCE: 388
gagaggcaga gcttactgtg                                                 20

<210> SEQ ID NO 389
<211> LENGTH: 24
<212> TYPE: DNA
<213> ORGANISM: Artificial Sequence
<220> FEATURE:
<223> OTHER INFORMATION: Primer

<400> SEQUENCE: 389
ggttatctga ggaagacaga gatg                                            24

<210> SEQ ID NO 390
<211> LENGTH: 22
<212> TYPE: DNA
<213> ORGANISM: Artificial Sequence
<220> FEATURE:
<223> OTHER INFORMATION: Primer

<400> SEQUENCE: 390
ctggaaccac agacatgaac ta                                              22

<210> SEQ ID NO 391
<211> LENGTH: 23
<212> TYPE: DNA
<213> ORGANISM: Artificial Sequence
<220> FEATURE:
<223> OTHER INFORMATION: Primer

<400> SEQUENCE: 391
```
ccaggactct gataattcca aca                                          23

<210> SEQ ID NO 392
<211> LENGTH: 21
<212> TYPE: DNA
<213> ORGANISM: Artificial Sequence
<220> FEATURE:
<223> OTHER INFORMATION: Primer

<400> SEQUENCE: 392
ctgaggtggg taaagggaat g                                            21

<210> SEQ ID NO 393
<211> LENGTH: 18
<212> TYPE: DNA
<213> ORGANISM: Artificial Sequence
<220> FEATURE:
<223> OTHER INFORMATION: Primer

<400> SEQUENCE: 393
attgaggctc agggaggt                                                18

<210> SEQ ID NO 394
<211> LENGTH: 22
<212> TYPE: DNA
<213> ORGANISM: Artificial Sequence
<220> FEATURE:
<223> OTHER INFORMATION: Primer

<400> SEQUENCE: 394
agcttactga gcaagtggga ag                                           22

<210> SEQ ID NO 395
<211> LENGTH: 20
<212> TYPE: DNA
<213> ORGANISM: Artificial Sequence
<220> FEATURE:
<223> OTHER INFORMATION: Primer

<400> SEQUENCE: 395
taaacagagg cagggagggt                                              20

<210> SEQ ID NO 396
<211> LENGTH: 22
<212> TYPE: DNA
<213> ORGANISM: Artificial Sequence
<220> FEATURE:
<223> OTHER INFORMATION: Primer

<400> SEQUENCE: 396
ctccttgcct cttctctcat tt                                           22

<210> SEQ ID NO 397
<211> LENGTH: 21
<212> TYPE: DNA
<213> ORGANISM: Artificial Sequence
<220> FEATURE:
<223> OTHER INFORMATION: Primer

<400> SEQUENCE: 397
cagtcaatct ttccgtgttg c                                            21

<210> SEQ ID NO 398
<211> LENGTH: 22
<212> TYPE: DNA

```
<213> ORGANISM: Artificial Sequence
<220> FEATURE:
<223> OTHER INFORMATION: Primer

<400> SEQUENCE: 398
tctctcccag agagtagtta cc                                            22

<210> SEQ ID NO 399
<211> LENGTH: 20
<212> TYPE: DNA
<213> ORGANISM: Artificial Sequence
<220> FEATURE:
<223> OTHER INFORMATION: Primer

<400> SEQUENCE: 399
gtgtggagtt tggcctcata                                               20

<210> SEQ ID NO 400
<211> LENGTH: 17
<212> TYPE: DNA
<213> ORGANISM: Artificial Sequence
<220> FEATURE:
<223> OTHER INFORMATION: Primer

<400> SEQUENCE: 400
cccagtcaac gctaggc                                                  17

<210> SEQ ID NO 401
<211> LENGTH: 20
<212> TYPE: DNA
<213> ORGANISM: Artificial Sequence
<220> FEATURE:
<223> OTHER INFORMATION: Primer

<400> SEQUENCE: 401
tgagagagat gtcgggagag                                               20

<210> SEQ ID NO 402
<211> LENGTH: 20
<212> TYPE: DNA
<213> ORGANISM: Artificial Sequence
<220> FEATURE:
<223> OTHER INFORMATION: Primer

<400> SEQUENCE: 402
ctttgctctg tccagcacta                                               20

<210> SEQ ID NO 403
<211> LENGTH: 22
<212> TYPE: DNA
<213> ORGANISM: Artificial Sequence
<220> FEATURE:
<223> OTHER INFORMATION: Primer

<400> SEQUENCE: 403
ccttgcacta catcagtcta gc                                            22

<210> SEQ ID NO 404
<211> LENGTH: 21
<212> TYPE: DNA
<213> ORGANISM: Artificial Sequence
<220> FEATURE:
<223> OTHER INFORMATION: Primer

<400> SEQUENCE: 404
gattctgttc tgtgcccttc t                                             21
```

```
<210> SEQ ID NO 405
<211> LENGTH: 21
<212> TYPE: DNA
<213> ORGANISM: Artificial Sequence
<220> FEATURE:
<223> OTHER INFORMATION: Primer

<400> SEQUENCE: 405
cctgcaccat gcttcctata c                                              21

<210> SEQ ID NO 406
<211> LENGTH: 19
<212> TYPE: DNA
<213> ORGANISM: Artificial Sequence
<220> FEATURE:
<223> OTHER INFORMATION: Primer

<400> SEQUENCE: 406
agagcagcca tggatcttg                                                 19

<210> SEQ ID NO 407
<211> LENGTH: 21
<212> TYPE: DNA
<213> ORGANISM: Artificial Sequence
<220> FEATURE:
<223> OTHER INFORMATION: Primer

<400> SEQUENCE: 407
catttctcca cctccaagac a                                              21
```